(12) United States Patent
Vásquez Velásquez et al.

(10) Patent No.: US 11,390,622 B2
(45) Date of Patent: Jul. 19, 2022

(54) PYRIMIDO-ISOQUINOLIN-QUINONE DERIVATIVE COMPOUNDS, AND PHARMACEUTICALLY ACCEPTABLE SALTS, ISOMERS AND TAUTOMERS THEREOF; PHARMACEUTICAL COMPOSITION; PREPARATION METHOD; AND USE THEREOF IN THE TREATMENT OF DISEASES CAUSED BY BACTERIA AND MULTIDRUG-RESISTANT BACTERIA

(71) Applicant: Universidad de Chile, Santiago (CL)

(72) Inventors: David Reinaldo Vásquez Velásquez, Santiago (CL); Juan Andrés Andrades Lagos, Santiago (CL); Javier Andrés Campanini Salinas, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 0 days.

(21) Appl. No.: 16/067,033

(22) PCT Filed: Dec. 29, 2016

(86) PCT No.: PCT/CL2016/050080
§ 371 (c)(1),
(2) Date: Jun. 28, 2018

(87) PCT Pub. No.: WO2017/113031
PCT Pub. Date: Jul. 6, 2017

(65) Prior Publication Data
US 2019/0367505 A1 Dec. 5, 2019

(30) Foreign Application Priority Data
Dec. 30, 2015 (CL) .................................. 3780-2015

(51) Int. Cl.
*C07D 471/04* (2006.01)
*A61P 31/04* (2006.01)

(52) U.S. Cl.
CPC ............ *C07D 471/04* (2013.01); *A61P 31/04* (2018.01)

(58) Field of Classification Search
CPC .................................................. C07D 471/04
See application file for complete search history.

(56) References Cited

FOREIGN PATENT DOCUMENTS

| WO | WO 02/102793 A2 | 12/2002 |
| WO | WO 2005/026104 A1 | 3/2005 |
| WO | WO 2005/049605 A1 | 6/2005 |

OTHER PUBLICATIONS

Vasquez et al., Bioorganic & Med. Chem. Letters 19(2009) 5060-5062.*
Valderrama et al., Bioorganic & Med. Chem. 16(2008) 10172-10181.*
Valderrama et al., Tet. Let. 49(2008) 703-706.*
Vasquez et al., European J'nal of Med. Chem. 45(2010) pp. 5234-5242.*
Vasquez et al. Invest New Drugs (2012) 30:1003-1011.*
Vasquez, D. Diserio, "Sintesis y Evaluation Antitumoral de Azaanalogos de anguciclinon . . . " de Doctor en Quimica, Pontificia Universidad Catolica de Chile, Chile, Oct. 2009.
Applicants have not included entire D1 article due to size. It may be downloaded at: http://repositorio.conicyt.cl/bitstream/handle/10533/179654/VASQUEZ_DAVID_0810D.pdf.
Vasquez, D. et al, "Aminopyrimidoisoquinolinequinone (APIQ) redox cycling is potentiated by ascorbate . . . ", Invest New Drugs, Apr. 5, 2011 ,vol. 30.
Vasquez, D. et al, "Synthesis and antitumor evaluation of . . . ", Bioorganic & Medicinal Chemistry Letters, Jul. 10, 2009, vol. 19.
Vasquez, D. et al, "Studies on Quiriones. Part 46. Synthesis and In Vitro Antitumor Evaluation . . . ", European Journal of Medicinal Chemistry, Aug. 21, 2010, vol. 45.
Valderrama, J. et al, "Studies on Quiriones. Part 44: Novel Agucyclinone N-heterocyclic Analogues . . . ", Bioorganic & Medicinal Chemistry, Nov. 5, 2008, vol. 16.
Valderrama, J. et al, "Design and synthesis of angucyclinone AB-pyrido [2,3-d]pyrimidine analogues", Tetrahedron Letters, Nov. 21, 2007, vol. 49.
International Search Report from counterpart PCT application No. PCT/CL2016/050080 dated Apr. 28, 2017.

(Continued)

*Primary Examiner* — Paul V Ward
(74) *Attorney, Agent, or Firm* — Procopio, Cory, Hargreaves & Savitch LLP

(57) ABSTRACT

The present invention provides pyrimidine-isoquinolin-quinone derivatives of formula I, their salts, isomers, pharmaceutically acceptable tautomers; pharmaceutical composition; preparation procedure; and their use in the treatment of bacterial and resistant bacterial diseases, such as methiicillin-resistant *Staphylococcus aureus* (MRSA), intermediate vancomycin-resistant *Staphylococcus aureus* (VISA), vancomycin-resistant *Staphylococcus aureus* (VRSA), vancomycin-resistant *Enterococcus* spp. (VRE), *Enterococcus faecalis*, Emerging *Staphylococcus aureus* with resistance to linezolid and/or bacterial strains not susceptible to daptomycin.

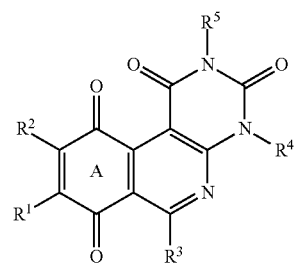

Where the radicals $R^1$, $R^2$, $R^3$, $R^4$ and $R^5$ are as defined in the work specifications of the present invention.

14 Claims, 3 Drawing Sheets

(56) References Cited

OTHER PUBLICATIONS

Kaliappan Krishna P et al: "Angucyclinone antibiotics: total syntheses of YM-181741, (+)-ochromycinone, (+)-rubiginone B2, (−)-tetrangomycin, and MM-47755.", The Journal of Organic Chemistry Aug. 3, 2007, vol. 72, No. 16, Aug. 3, 2007 (Aug. 3, 2007), pp. 6116-6126, ISSN: 0022-3263.

* cited by examiner

PYRIMIDO-ISOQUINOLIN-QUINONE DERIVATIVE COMPOUNDS, AND PHARMACEUTICALLY ACCEPTABLE SALTS, ISOMERS AND TAUTOMERS THEREOF; PHARMACEUTICAL COMPOSITION; PREPARATION METHOD; AND USE THEREOF IN THE TREATMENT OF DISEASES CAUSED BY BACTERIA AND MULTIDRUG-RESISTANT BACTERIA

SCOPE OF THE INVENTION

The present invention refers to antibacterial compounds derived from a pyrimido-isoquinoline-quinones nucleus, processes for their preparation, and methods for their use.

BACKGROUND OF THE INVENTION

Prior Art

Before the 20th century, medicine did not have the tools to combat infectious diseases, as not even one of the main etiologies of these ailments, bacteria, had been discovered. Before the discovery of antibiotics, a simple infection could result in death for many people. Indeed, infant mortality was very high, as was maternal mortality before and after childbirth. In the 17th century, half of Europe's population died of bacterial infections [1]. Life expectancy in 1930 was 35 to 40 years; today, this number has increased considerably [2], and it is largely due to the availability of antibiotics.

The discovery of antibiotics is momentous in the history of medicine. Its beginnings are linked to a great researcher in microbiology, Paul Ehrlich, whose ideas at the time were revolutionary. He sought to create a so-called "magic bullet" to kill microorganisms inside the body without harming the person (thus the "magic" bit). This idea emerged in the beginning of the 20th century, when there was only a recent awareness of the existence of microorganisms. More than 606 experiments were conducted before the "magic bullet" called Salvarsan was born. In 1910, Salvarsan became the first product capable of killing bacteria within the human body and was used to combat syphilis and yaws, both bacterial diseases. In 1914, a more efficient product than Salvarsan was created: Neosalvarsan. A new chapter would later begin with the advent of sulfonamides, resulting from Domagk's research [3].

In 1929, Alexander Fleming realized that a fungus called *Penicillium notatum* inhibited the growth of bacteria. Nevertheless, the researcher was not capable of completing his discovery, failing to demonstrate the efficiency of this fungus as a "magic bullet". This product received the name Penicillin. In 1940 it was consolidated as the first antibiotic thanks to the work of Chain and Florey, who was finally able to isolate and confirm the effects of this agent [4]. This is why penicillin, first discovered in 1929, became an antibiotic in 1940, when it was formally introduced into human medical treatments. The Second World War saw the construction of the most advanced research laboratory for penicillin and sulphas, as their generally perceived benefits spurred a significant increase in their production [3].

The advent of cephalosporins was also a major advance in antibiotic therapy. Near a sewage outlet on the Sardinian coast, the Italian Giuseppe Brotzu of the University of Cagliari isolated the newly discovered beta-lactam from "*Cephalosporium acremonium*", the first source of these drugs. The subsequent discovery of the active nucleus of cephalosporin C and the possibility of adding side chains made it possible to develop new semi-synthetic compounds with much greater antibacterial activity.

Macrolides, effective against Gram-positives, an alternative in penicillin-allergic patients, began with erythromycin; this "orally effective" antibiotic is produced by "*S. Erythreus*", a strain derived from the soils of the Philippine archipelago [5]. Other types of antibiotics started to emerge thereafter, until our current medical arsenal was developed.

Initially, the term antibiotic was only used to refer to organic compounds of biological origin, which could be obtained from bacterial cultures (*Bacillus, Streptomyces*) or fungi (*Penicillium, Cephalosporium*) and that are toxic to other microorganisms. At present, this term is also used to refer to synthetic compounds, i.e. produced exclusively by chemical synthesis, or semi-synthetic compounds, derived from a natural antibiotic produced by a microorganism and whose chemical structure is modified to improve its pharmacokinetic properties, spectrum, or even, to decrease its toxicity [6].

According to the Spanish Royal Academy, an antibiotic is a chemical substance produced by a living being or manufactured through synthesis, capable of halting the development of certain pathogenic microorganisms, either because of its bacteriostatic action, or because of its bactericidal action, killing them [7].

Almost parallel to the discovery and use of antibiotics, bacterial resistance became a reality. A resistant strain of bacteria is defined as one that is capable of multiplying in the presence of higher concentrations than those reached with therapeutic doses [8].

Bacteria can develop resistance to antibiotics by spontaneous mutation or by gene exchange between strains and bacterial species [9]. Alexander Fleming was the first to warn of the potential significance of bacterial resistance[10]. Alarming results soon followed, with one hospital in the United Kingdom reporting that 14% of *Staphylococcus aureus* infections were resistant to penicillin in 1946. By 1950, that proportion had risen to 59 percent. In the 1990s, the resistance rate of *S. aureus* to penicillin had reached levels above 80% in both hospitals and the community [11]. Antimicrobial resistance is primarily referred to in the clinical setting as measures for infection control and the selective pressure of antimicrobial agents on a pathogen. Antimicrobial resistance is a long-standing problem and is now a public health issue [8]. A concrete example of this is that multidrug-resistant tuberculosis is now reported in 64 countries and there are 440,000 new cases each year, causing at least 150,000 deaths.

Other multi-resistant infections of hospital origin are caused by pathogens such as methicillin-resistant *Staphylococcus aureus* (MRSA) or *Enterococcus* spp. vancomycin resistant (VRE).

Methicillin-resistant *Staphylococcus aureus* or MRSA is a mutant of *Staphylococcus aureus* bacteria that has become resistant to several antibiotics, first penicillin in 1947, and then methicillin. While an otherwise healthy individual is usually not severely affected by MRSA, its presence and subsequent infection can be life-threatening for hospital patients with severe injuries or a weakened immune system.

MRSA is mainly acquired at hospitals. Its most serious manifestations are sepsis, cellulitis and nosocomial pneumonia, a disease that can be fatal and is acquired mainly by patients with assisted or mechanical breathing.

MRSA, like VRE, has responded to pharmacological treatment with linezolid to curb infection. VRE, on the other hand, in order to become a vancomycin-resistant bacterium, must typically obtain new DNA in the form of plasmids or transposons encoding genes that confer resistance to vancomycin. This acquired resistance is distinct and different from the natural vancomycin resistance of certain enterococcal species, including *E. gallinarum* and *E. casseliflavus*.

Vancomycin resistance to *E. faecalis* and *E. faecium* with clinical isolates of the strains was first documented in the United States in the 1980s. Mechanistically acquired vancomycin resistance is classified into six different types of resistance for *Enterococcus* spp: Van-A, Van-B, Van-C, Van-D, Van-E and Van-G [9]. Van-A VRE is resistant to both vancomycin and teicoplanin antibiotics, Van-B VRE is resistant to vancomycin but susceptible to teicoplanin, and Van-C is only partially resistant to vancomycin, and susceptible to teicoplanin.

Biochemically speaking, the resistance mechanism to vancomycin for *Enterococcus* involves an alteration of the peptidoglycan synthesis pathway. The resulting D-alanyl-D-lactate decreases the interaction between vancomycin and peptide through the loss of a hydrogen bridge (four, as opposed to five for D-alanyl D-alanine). The variation in D-alanyl-D-serine causes a six-fold loss of affinity between vancomycin and the peptide, preventing the antibiotic from performing its function.

The use of cephalosporins that could aid VRE colonization and infection is generally considered a risk factor, and their restriction is associated with a decrease in VRE infections and their transmission in hospitals. Bacteria such as *Lactobacillus rhamnosus* GG (LGG), a strain of *L. rhamnosus*, have been used to treat VRE infections. Linezolid is normally used to treat VRE.

On the other hand, the resistance mechanism of MRSA involves the synthesis of a new penicillin binding protein (PBP), called PBP 2a (or PBP) with low affinity for β-lactamic drugs. This is encoded by a new gene called mec A and retains its transpeptidase action in the bacterial wall synthesis even when the other PBPs of *S. aureus* are inhibited by β-lactamic drugs.

Other multi-resistant bacterial infections are mediated by *Staphylococcus aureus* with intermediate vancomycin resistance (VISA), emerging strains with resistance to *Staphylococcus aureus* linezolid, or emerging strains with resistance to *Enterococcus faecalis* linezolid with resistance and/or strains that are not susceptible to daptomycin.

Antimicrobial resistance is also starting to affect even the latest generation of oral cephalosporins and their prevalence is increasing worldwide. Some treatments are becoming more complex, such as gonorrhea, and intractable gonococcal infections could increase their morbidity and mortality rates, which would reverse progress in the control of this sexually transmitted infection. In addition, resistance through hydrolytic enzymes, such as Metalobetalactamase NDM-1, has appeared in several Gram-negative bacilli. This can render several potent antibiotics ineffective, such as carbapenemic-derived compounds, which are often used as a last resort defense against multi-resistant bacterial strains [12].

The causes that have facilitated this hostile context and, in turn, provide favorable conditions for the emergence and spread of resistant microorganisms are mainly over-prescription (when an antibiotic is not required for prevention or in doses above their therapeutic level) and under-prescription (doses under their therapeutic level); non-observance of recommended doses; lack of regulation in sales [13]; inappropriate and irrational use of antibiotics, especially in livestock farming [14, 15]; poor practices in the prevention and control of infections and finally, poor adherence to antibiotic treatments by patients, which is in turn caused by poor education on the subject. The impact of antimicrobial resistance is an enormous public health issue, as it increases the duration of infections and the risk of death, endangering the control of infectious diseases by reducing the effectiveness of treatments. In other words, it threatens to take us back to the time before the discovery of antimicrobials.

Despite all this, fewer and fewer new antibiotics are being created [13], further complicating the situation. Bacteria resistance to antibiotics is a predictable consequence of genetic variation; administering an antibiotic exerts selective pressure on bacteria so that they are forced to adapt by survival [16]. Consequently, the mechanisms through which bacterial resistance operates are diverse, including the following: enzymatic destruction or inactivation of the antibiotic, modification of the pharmacological target, restriction of the antibiotic's entry into the cell and the active expulsion of the antibiotic before it acts [17]. Finally, the pressure of a given antibiotic on an environment favors that populations of bacteria with a resistant characteristic multiply and prevail in the environment. Once resistance is acquired, it can be passed vertically from mother to daughter bacteria, creating clones with such resistance, or horizontally to other bacteria by transformation, transduction, transposition or conjugation mechanisms [16].

Examples of types of bacteria that are representative of the resistance generation process (ESKAPE pathogens, with current treatment but with a rapid loss of effectiveness of the same treatments) and of bacteria that do not currently have antibiotic treatment are: *Eschericha coli, Pseudomonas aeruginosa, Staphylococcus aureus, Enterococcus faecalis, Enterobacter* Spp., *Klebsiella* Spp. and *Acinetobacter baumannii*, among other new ones that appear year after year.

Currently available antibiotics have traditional targets and whose general aim is to synthesize the bacterial cell wall, protein synthesis or DNA replication, sometimes allowing antibiotics that are not structurally related to each other to share common objectives. Mutations in these common objectives are precisely the ones that occur most frequently in bacteria resistant to multiple antibiotics [18]. It is therefore essential to develop new antibiotics that can avoid currently known resistance and/or attack new targets. As for this last point, there are three parameters to consider when selecting these targets in order to avoid bacterial resistance:

1. The antimicrobial target must be essential for the survival of the bacterium, so rendering this unit non-functional is highly likely to result in the death of the microorganism.
2. The target must be preserved over time, i.e. with a low mutagenicity rate, making it more complex for the bacteria to develop changes that can lead to the avoidance of the antimicrobial agent.
3. The unit to be attacked must be a common structure in multiple bacterial types, thus covering a broad spectrum.

In light of these parameters, an antibacterial biological target is the electron transport chain (CTe), where ubiquinone (UBQ) is essential for its functioning. It allows the flow of electrons from complex I to complex III and from complex II to complex III [19], so a functional blockage of this unit could result in a drop in ATP generation and progressive damage to bacterial viability [20].

Chemically, ubiquinone corresponds to 2,3-dimethoxy-5-methyl-6-polyisoprenyl-1,4-benzoquinone [21], so it is inferred that quinonic compounds may interfere with the electron transport chain by emulating UBQ.

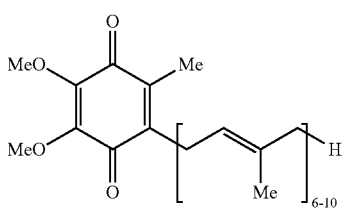

General structure of ubiquinone

It should also be noted that quinoid molecules have interesting electrochemical properties, which can be reversibly reduced first to a semiquinone and then to a hydroquinone due to their ability to accept electrons [21]. This is because they are compounds with the capacity to capture and generate free radicals, which can in turn generate an inadequate redox medium for bacterial survival [22].

It is interesting to note that there is a balance between the three quinoid species (quinone, semiquinone and hydroquinone), with a prevalence of the most stable, as shown below:

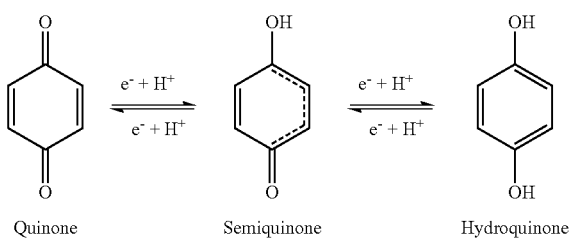

Quinone     Semiquinone     Hydroquinone

Under this light, it could be speculated that if another molecule, similar to UBQ, is introduced into the electron transport chain system, with the capacity to accept electrons and in turn also to efficiently transfer them (not to the III complex, but to another acceptor found in the system, such as molecular oxygen ($O_2$)), it could induce the generation of reactive oxygen species (ROS). This, in addition to naturally occurring ROS in the bacterial electron transport chain, can lead to progressive damage to supporting structures, substrates, proteins, enzymes or genetic material of the bacterium, making them lose their viability and causing death [22, 23, since it is widely documented that oxygen-reactive species play a key role in the formation of apoptosis [24].

Nevertheless, since both bacterial and human cells use the electron transport chain (CTe) to obtain energy in the form of ATP, toxicity problems could surface. That said, there are morphological differences between human and bacterial cells that could provide bacterial selectivity because, in the case of the latter, the electron transport chain is found in the plasma membrane. In humans, however, it is found in the inner membrane of the mitochondria [19]. Therefore, by varying the lipophilicity of an antibiotic molecule whose target is the electron transport chain, it can, in turn, be manipulated to become trapped in the first barrier it encounters. In bacteria, this barrier is the place where the electron transport chain is located. In human cells, on the other hand, it would fall short as it would have to cross more barriers to reach the mitochondria.

Considering that ubiquinone is essential for the functioning of CTe and that it in turn complies with the three aforementioned parameters of an efficient antibiotic target, it is inferred that using this unit as a target or antibacterial target, through molecules that imitate it, could be a good solution to combat resistant strains.

Quinones are a second chemical group of compounds that are in the preclinical and clinical research stage due to their great diversity of biological properties, as antiparasitic, antibacterial, anticancer and antifungal agents [25].

There are certain quinones that possess excellent antibiotic properties, among which we can highlight the following:

(a) 7-Methyljuglone, this compound has been shown to have therapeutic potential, in particular against *Mycobacterium tuberculosis* [26].

(b) Lapachol and its equivalents have been used in the treatment of ringworm, diarrhea, gonorrhea, parasitic infections and as antifungal agents [27, 28].

(c) Plumbagina shows activity against *Staphylococcus aureus* [29].

(d) Juglone and 7-methyljuglone are active against *Streptococcus mutans* and *S. sanguis* responsible for dental cavities, and against *Porphyromonas gingivalis* and *Prevotella*, intermediate causes of gingivitis [30].

(e) 5-amino-8-hydroxy-1,4-naphthoquinone is active against *S. aureus, S. intermedius* and *S. epidermidis* [31].

(f) 5,8-dihydroxy-1,4-naphthoquinone is active against mycobacterial species[32].

(g) Sulphur derivatives of naphthoquinone with p-anisidyl substitution show activity against *Streptococcus faecalis* and *Klebsiella pneumoniae* and compounds with o-anisidyl, phenyl and methyl substitutions have antimicrobial activity against *Escherichia coli* [32].

(h) and (i) 8-hydroxy-2-(1-hydroxyethyl)naphthalene[2,3-b]furan-(1-hydroxyethyl)naphthalene[2,3-b]furan-(1) 4,9-dione, a cyclic analogue of lapachol, has been reported as an antibacterial agent, showing activity against *Helicobacter pilori, Staphylococcus, Enterococcus, Bacillus* and *Clostridium* [33, 34].

The structures of the aforementioned drugs are shown below:

a)

b)

c)

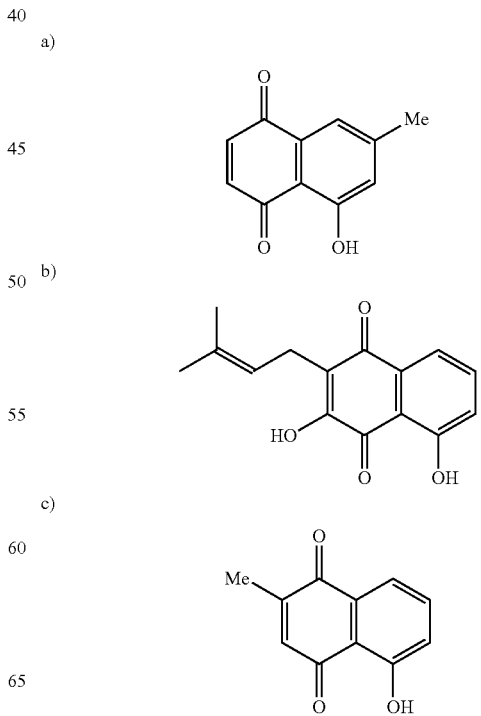

-continued d) 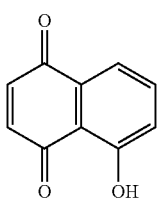

e) 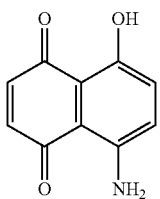

f) 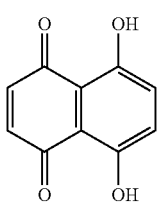

g) 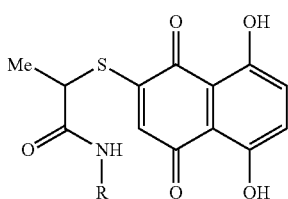

R = p-anisil
R = o-anisil
R = Fenil
R = Metil h) 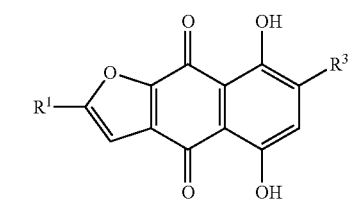

$R^1$ = —CH$_2$CH(OH); $R^2$ = H; $R^3$ = OH
$R^1$ = CH$_3$; $R^2$ = OH; $R^3$ = H
$R^1$ = CH$_3$; $R^2$ = H; $R^3$ = H

-continued i) 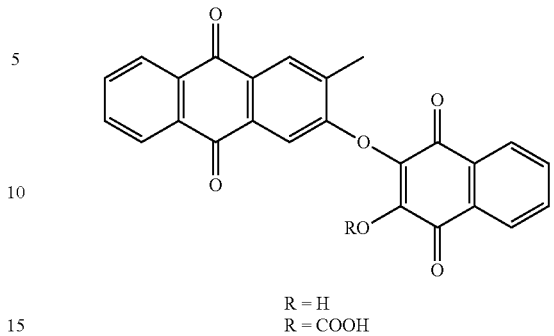

R = H
R = COOH

Other antibacterial agents described in the prior art are those presented in patents WO02/102793, WO2005/049605, WO2005/026104 which describe antibiotic compounds derived from pyridopyrimidines.

According to the Center for Disease Control and Prevention, the spread of resistant strains over the last 30 years has been steadily increasing worldwide, as can be seen in FIG. 2/3.

DESCRIPTION OF THE INVENTION

The present invention refers to quinonic derivative compounds of formula I, their isomers, their tautomers and/or their pharmaceutically acceptable salts, which are useful in the treatment of bacterial infections:

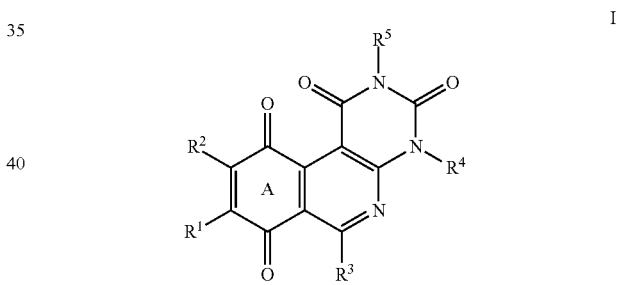

I where:
$R^1$ is —H, —NH$_2$, —OH, —SH, —NH—$R^6$, —N—$(R^6)_2$, —O—$R^6$,

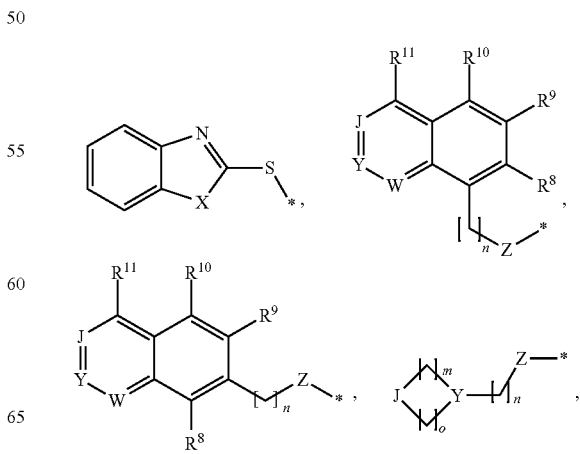

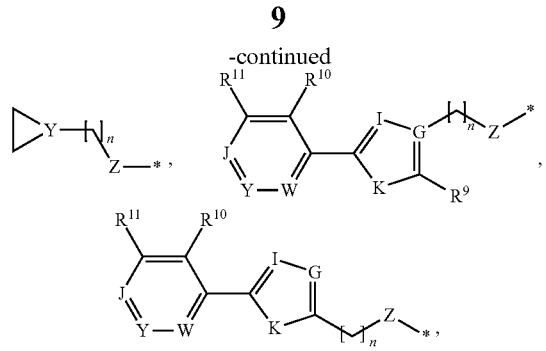

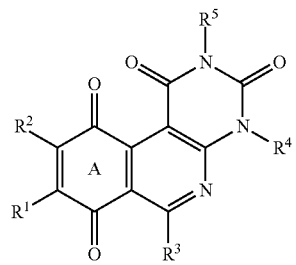

—S—R⁶, —SO—R⁶, —SO₂—R⁶, -alkyl C₁-C₁₅, —Si—R⁶, —SiO—R⁶, —NH—(CH₂)ₙ—R⁶, —N((CH₂)ₙ—R⁶), —O—(CH₂)ₙ—R⁶, —S—(CH₂)ₙ—R⁶, —Si—(CH₂)ₙ—R⁶;

where R⁶ is a C₁-C₁₅ alkyl group, a C₁-C₁₅ substituted alkyl group, phenyl, substituted-phenyl, substituted-aryl, substituted-aryl, heterocycle, substituted-heterocycle, heteroaryl, substituted-heteroaryl, where substitutions of the C₁-C₁₅ alkyl groups, aryl, phenyl, heterocycle and heteroaryl are:

C₁-C₁₅CO—Z-alkyl, C₁-C₁₅—Z—CO-alkyl, —H, -tert-butyl, -iso-propyl, —C₁-C₁₅ alkyl, —CF₃, halogen of the Cl, Br, F and I groups, —NH₂, —NO₂, —NH—R⁷, —N(R⁷)₂, —COOH, —COO—R⁷—OCO—R⁷, —O—R⁷, —CN, —S—R⁷, —S—CF₃ and substituted phenyl with —H, —C₁-C₁₅ alkyl, halogen of the Cl, Br, F and I group, —NH₂, —NO₂, —NH—R⁷, —N(R⁷)₂, —COOH, —COO—R⁷—OCO—R⁷, —O—R⁷, —CN, —S—R⁷, —S—CF; where R⁷ is a —H, C₁-C₁₅ alkyl —OH group;

where X is O, N or S;
where n=0-14;
where m=0-14;
where o=1-14;
where K, Z, P, G, I, Y, J and W are independently: O, N, SO₂, SO, S, C or Si; R² is —H, —NH₂, —OH, —SH, —NH—R⁶, —N—(R⁶)₂, —O—R⁶, —S—R⁶ and halogen of the Cl, Br, F and I group;
R³ is H, C₁-C₁₅ alkyl, —NH₂, —OH, —SH, —NH—R⁶, —N—(R⁶)₂, —O—R⁶, —S—R⁶;
where heterocycle is defined as a monocyclic ring, containing approximately 3 to 7 atoms in the ring, with 1 to 5 heteroatoms selected from N, O, and S, in the ring;
where heteroaryl is defined as a cyclic or polycyclic aromatic ring system with 3 to 7 atoms in the ring, with 1 to 4 heteroatoms selected between N, O, and S;
where aryl means a cyclic or polycyclic aromatic ring with 5 to 12 carbon atoms;
where R⁴ and R⁵ are H, a C₁-C₁₅ alkyl group;
where R⁸, R⁹, R¹⁰ and R¹¹ independently correspond to: —H, —C₁-C₁₅ alky, C₁-C₁₅ substituted alkyl with R⁷, halogen of the Cl, Br, F and I group, —NH₂, —NO₂, —NH—R⁷, —N(R⁷)₂, —COOH, —COO—R⁷—OCO—R⁷, —O—R⁷, —CN, —S—R⁷, —S—CF, -tert-butyl, -iso-propyl and —CF₃.

DETAILED DESCRIPTION OF THE INVENTION

The present invention refers to the use of antibacterial agents derived from the pyrimido-isoquinoline-quinone nucleus. The compounds used in accordance with the present invention are comprised by the following structural formula I:

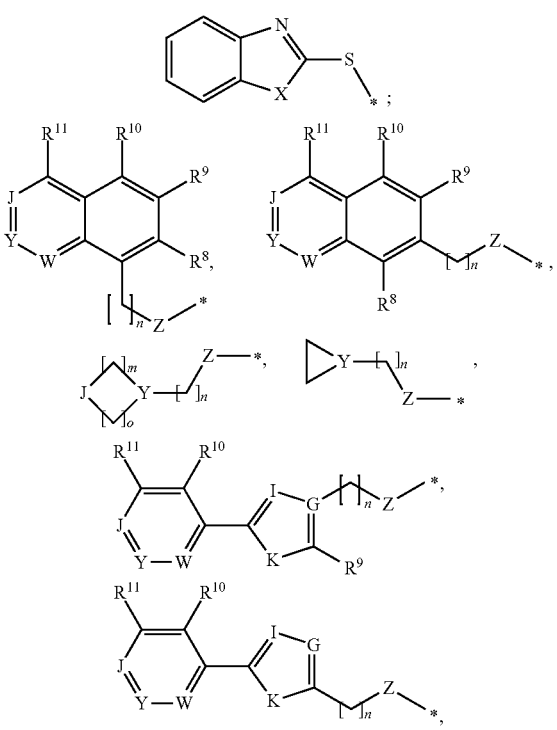

where:
R¹ es —H, —NH₂, —OH, —SH, —NH—R⁶, —N—(R⁶)₂, —O—R⁶, —S—R⁶, —C₁-C₁₅ alkyl, SO—R⁶, —SO₂—R⁶, —Si—R⁶, —SiO—R⁶, —NH—(CH₂)ₙ—R⁶, —N((CH₂)ₙ—R⁶)₂—O—(CH₂)ₙ—R⁶, —S—(CH₂)ₙ—R⁶, —Si—(CH₂)ₙ—R⁶;

where R⁶ is a C₁-C₁₅ alkyl group, a C₁-C₁₅ substituted alkyl group, phenyl, substituted phenyl, aryl, substituted aryl, heterocycle, substituted heterocycle, heteroaryl, hetero-substituted aryl, where the substitutions of the alkyl C₁-C₁₅, aryl, phenyl, heterocycle and heteroaryl groups are:

CO—Z-alkyl C₁-C₁₅, —Z—CO-alkyl' C₁-C₁₅, —H, -tert-butyl, -iso-³propyl, -alkyl C₁-C₁₅, —CF₃, halogen of the Cl, Br, F and I group, —NH₂, —NO₂, —NH—R⁷, —N(R⁷)₂, —COOH, —COO—R⁷—OCO—R⁷, —, —O—R⁷, —CN, —S—R⁷, —S—CF₃ and substituted phenyl with —H, -alkyl C₁-C₁₅, halogen of the Cl, Br, F and I group, —NH₂, —NO₂, —NH—R⁷, —N(R⁷)₂, —COOH, —COO—R⁷—OCO—R⁷, —O—R⁷, —CN, —S—R⁷, —S—CF; where R⁷ is an —H, alkyl C₁-C₁₅, —OH group;

where X is O, N or S;
where n=0-14;
where m=0-14;
where o=1-14;

where K, Z, P, G, I, Y, J y W are separately: O, N, $SO_2$, SO, S, C or Si;

$R^2$ is —H, —$NH_2$, —OH, —SH, —NH—$R^6$, —N—$(R^6)_2$, —O—$R^6$, —S—$R^6$ and halogen of the Cl, Br, F and I group;

$R^3$ is H, alkyl $C_1$-$C_{15}$, —$NH_2$, —OH, —SH, —NH—$R^6$, —N—$(R^6)_2$, —O—$R^6$, S—$R^6$;

where heterocycle is defined as a monocyclic ring, containing approximately 3 to 7 atoms in the ring, with 1 to 5 heteroatoms selected from N, O, and S, in the ring;

where heteroaryl is defined as a cyclic or polycyclic aromatic ring system of 3 to 7 atoms and the ring, with 1 to 4 heteroatoms selected between N, O, and S;

where aryl means a cyclic or polycyclic aromatic ring with 6 to 12 carbon atoms;

where $R^4$ and $R^5$ are H, a $C_1$-$C_{15}$ alkyl group;

where $R^8$, $R^9$, $R^{10}$ and $R^{11}$ separately correspond to: —H, —$C_1$-$C_{15}$ alkyl, $C_1$-$C_{15}$ substituted alkyl with $R^7$, halogen of the Cl, Br, F and I group, —$NH_2$, —$NO_2$, —NH—$R^7$, —$N(R^7)_2$, —COOH, —COO—$R^7$—OCO—$R^7$, —O—$R^7$, —CN, —S—$R^7$, —S—CF, -tert-butyl, -iso-propyl y —$CF_3$.

A second preferred group of the compounds in the present invention includes compounds containing formula I, where $R^1$ is —NH—$(CH_2)_n$—$R^6$, —O—$(CH_2)_n$—$R^6$, —S—$(CH_2)_n$—$R^6$;

where $R^6$ is a substituted phenyl group, where substitutions of the phenyl group are independently: —Z—CO-alkyl $C_1$-$C_{15}$, —CO—Z—$^{13}C_1$-$C_{15}$ alkyl, —H, -tert-butyl-iso-propyl, -alkyl $C_1$-$C_{15}$, —$CF_3$, halogen of the Cl, Br, F and I group, —$NH_2$, —$NO_2$, —NH—$R^7$, —$N(R^7)_2$, —COOH, —COO—$R^7$—OCO—$R^7$, —O—$R^7$, —CN, —S—$R^7$, —S—CF y substituted phenyl con —H, -alkyl $C_1$-$C_{15}$, halogen of the Cl, Br, F and I group, —$NH_2$, —$NO_2$, —NH—$R^7$, —$N(R^7)_2$, —COOH, —COO—$R^7$—OCO—$R^7$, —O—$R^7$, —CN, —S—$R^7$, —S—$CF_3$;

where $R^7$ is an —H, $C_1$-$C_{15}$ alkyl, —OH group;

where n=0-2;

where z is independently: O, N, $SO_2$, SO, S, C or Si;

$R^2$ is H;

$R^3$ is H and $C_1$-$C_{15}$ alkyl, where $R^4$ and $R^5$ are H, a $C_1$-$C_{15}$ alkyl group.

A third preferred group of the compounds in the present invention includes compounds containing formula I, where:

$R^1$ is —NH—$(CH_2)_n$—$R^6$, —O—$(CH_2)_n$—$R^6$, —S—$(CH_2)_n$—$R^6$;

where $R^6$ is a $C_1$-$C_{15}$ alkyl group or a substituted phenyl group, where the substitutions of the phenyl group are independently: —H, -alkyl $C_1$-$C_{15}$ y halogen of the Cl, Br, F and I group;

where n=0-2;

$R^2$ is —H, —NH—$R^6$, —N—$(R^6)_2$, —O—$R^6$, —S—$R^6$;

$R^3$ is H, $C_1$-$C_{15}$ alkyl;

where $R^4$ and $R^5$ are H, a $C_1$-$C_5$ alkyl group;

where the $R^6$ substitutions of the phenyl group are in the ortho and para positions.

A fourth preferred group of the compounds of the present invention includes compounds containing formula I, where $R^1$ is

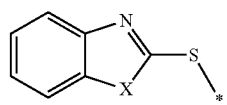

where X is O, N or S;

$R^2$ is —H;

$R^3$ is H, $C_1$-$C_{15}$ alkyl;

where $R^4$ and $R^5$ are H, a $C_1$-$C_{15}$ alkyl group.

A fifth preferred group of the compounds of the present invention includes compounds containing formula I, where $R^1$ are

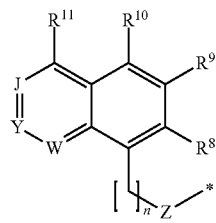 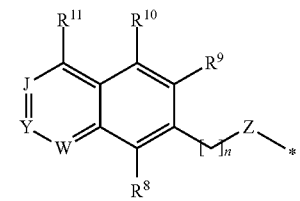

where n=0-8;

where w is independently: O, N, $SO_2$, SO, S, C or Si;

where y, z and j are C or N;

$R^2$ is —H;

$R^3$ is H, $C_1$-$C_{15}$ alkyl;

where $R^4$ and $R^5$ are H, a $C_1$-$C_{15}$ alkyl group;

where $R^8$, $R^9$, $R^{10}$ and $R^{11}$ independently correspond to: —H, —$C_1$-$C_{15}$ alkyl, $C_1$-$C_{15}$ substituted alkyl with $R^7$, halogen of the Cl, Br, F and I group, —$NH_2$, —$NO_2$, —NH—$R^7$, —$N(R^7)_2$, —COOH, —COO—$R^7$, —OCO—$R^7$, —O—$R^7$, —CN, —S—$R^7$, —S—CF, -tert-butyl, -iso-propyl y —$CF_3$;

where $R^7$ is a —H, $C_1$-$C_{15}$ alkyl, —OH group.

A sixth preferred group of the compounds of the present invention includes compounds containing formula I, where

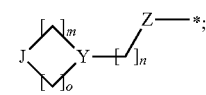

$R^1$ is where n=0-8;

where m=0-6;

where o=1-6;

where Z, J are independently: O, N, $SO_2$, SO, S, C or Si;

where Y is C or N;

$R^2$ is —H;

$R^3$ is H, alkyl $C_1$-$C_{15}$;

where $R^4$ y $R^5$ son —H, un alkyl group $C_1$-$C_{15}$;

A seventh preferred group of the compounds of the present invention includes compounds containing formula I, where $R^1$ is;

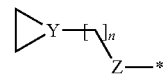

where n=0-8;

where Z is independently: O, N, $SO_2$, SO, S, C or Si;

where Y is C or N;

$R^2$ is —H;

$R^3$ is H, $C_1$-$C_{15}$ alkyl;

where $R^4$ and $R^5$ are H, a $C_1$-$C_{15}$ alkyl group.

An eighth preferred group of the compounds of the present invention includes compounds containing formula I, where
R$^1$ are

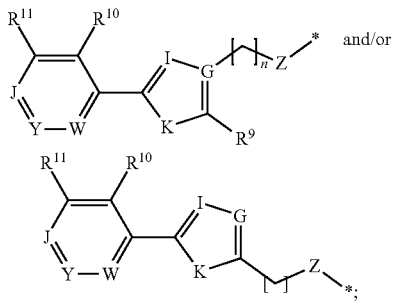

where n=0-8;
where K, Z are independently: O, N, SO$_2$, SO, S, C or Si;
where G, I, Y, J and W are independently: N or C;
R$^2$ is —H;
R$^3$ is —H, C$_1$-C$_{15}$ alkyl;
where R$^4$ and R$^5$ are H, a C$_1$-C$_{15}$ alkyl group;
where R$^9$, R$^{10}$ and R$^{11}$ independently correspond to: —H, —C$_1$-C$_{15}$ alkyl, C$_1$-C$_{15}$ substituted alkyl with R$^7$, halogen of the Cl, Br, F and I group, —NH$_2$, —NO$_2$, —NH—R$^7$, —N(R$^7$)$_2$, —COOH, —COO—, R$^7$—OCO—R$^7$, —O—R$^7$, —CN, —S—R$^7$, —S—CF$_3$, -tert-butyl, -iso-propyl and —CF$_3$; where R$^7$ is a —H, C$_1$-C$_{15}$ alkyl, —OH group.

The term "halogen" as used in this document refers to fluorine, chlorine, bromine or iodine, unless otherwise indicated.

The term "alkyl" as used in this document refers to a linear, cyclic or branched hydrocarbon residue, preferably an alkyl group of 1 to 15 carbon atoms, unless otherwise indicated.

The term "cycloalkyl" as used in this document refers to a cyclic alkyl, e.g. cyclopropyl, unless otherwise indicated.

The term "aryl" as used in this document refers to a monocyclic or bicyclic aromatic group, in which each ring of the individual or fused ring system contains 6-12, preferably 6-10 cyclic atoms [sic], e.g., including, but not always limited to, phenyl, naphthyl, biphenyl and indenyl.

The term "heterocycloalkyl" or "heterocycle" as used in this document refers to a cyclic alkyl, e.g., monocyclic or bicyclic alkyl, containing one or more heteroatoms, preferably one to four heteroatoms, selected from O, N and S, unless otherwise indicated.

Examples of monoheterocycloalkyl include, but are not limited to, piperidinil, morpholinil, thiamorpholinil, pyrrolidinil, imidazolidinil, tetrahydrofuranil, piperazinil, and similar groups of the above.

Where "heterocycle", which falls within "heterocycloalkyls", is defined as a monocyclic ring, containing approximately between 3 to 7 atoms in the ring, with 1 to 5 selected heteroatoms between N, O, and S, in the ring.

The term "heteroaryl" as used in this document refers to an aromatic group, e.g., monocyclic or bicyclic group, containing one to four selected heteroatoms of O, N, and S, and one or more carbons as members of the ring are substituted with C=O, unless otherwise indicated.

Examples of monocyclic heteroaryl include but are not limited to thiazolyl, oxazolyl, thiazolyl, thiophenyl, furanyl, pyrolysis, imidazolyl, isooxazolyl, pyrazolyl, triazolyl, thiadiazolyl, tetrazolyl, oxadiazolyl, pyridinyl, pyridazinyl, pyrimidoinyl, pyrazinyl and similar groups of the above.

Examples of bicyclic heteroaryl include, but are not limited to, indolyl, benzothiophenyl, benzimidazolyl, benzimidazolyl, benzoxazolyl, benzthiazolyl, benzothiazolyl, benztriazolyl, quinolinyl, isoquinolineyl, furinyl, furopyridinyl, oxychromene, dioxoisoisoindoline, and similar groups of the above.

Where in a specific definition, "heteroaryl" is defined as a cyclic or polycyclic aromatic ring system of 3 to 7 atoms in the ring, which has between 1 to 4 selected heteroatoms between N, O, and S.

The compounds of the present invention may also form a pharmaceutically acceptable salt. Such salt may be, but is not limited to, a pharmaceutically acceptable non-toxic addition salt containing acid. For example, salt may include addition salts with acids formed from inorganic acids such as hydrochloric acid, sulfuric acid, nitric acid, phosphoric acid, hydrobromic acid, hydrofluoric acid, and others; organic carbonic acids such as tartaric acid, formic acid, citric acid, acetic acid, trichloroacetic acid, trifluoroacetic acid, gluconic acid, benzoic acid, lactic acid, fumaric acid, maleic acid, and others; and sulfonic acids such as methanesulfonic acid, benzensulfonic acid, p-toluensulfonic acid, naphthalenesulfonic acid, and others.

In addition, the compound of the present invention may have an asymmetrical carbon center, and thus may be present in the form of an R or S isomer, racemic compounds, a diastereomeric mixture, or individual diastereomer. Such entire isomers and mixtures are included within the scope of the present invention.

The solvates and hydrates of the compound of formula (I) are also covered within the scope of the present invention.

The abovementioned compounds of the present invention may be prepared by methods that are known in the art or according to the following working examples. The following compounds are especially representative of the compounds of the present invention:

6-Ethyl-2,4-dimethylpyrimido[4,5-c]isoquinoline 1,3,7,10(2H, 4H)-tetraone
6-Ethyl-2,4-dimethyl-8-(phenythio)pyrimido[4,5-c]isoquinoline-1,3,7,10(2H,4H)-tetraone
6-Ethyl-2,4-dimethyl-8-(o-tolylthio)pyrimido[4,5-c]isoquinoline-1,3,7,10(2H,4H)-tetraone
6-ethyl-8-((2-methoxyphenyl)thio)-2,4-dimethylpyrimido[4,5-c]isoquinoline-1,3,7,10(2H,4H)-tetraone
6-ethyl-8-((2-fluorophenyl)thio)-2,4-dimethylpyrimido[4,5-c]isoquinoline-1,3,7,10(2H,4H)-tetraone
8-((2-chlorophenyl)thio)-6-ethyl-2,4-dimethylpyrimido[4,5-c]isoquinoline-1,3,7,10(2H,4H)-tetraone
8-((2-bromophenyl)thio)-6-ethyl-2,4-dimethylpyrimido[4,5-c]isoquinoline-1,3,7,10(2H,4H)-tetraone
6-Ethyl-2,4-dimethyl-8-(m-tolylthio)pyrimido[4,5-c]isoquinoline 1,3,7,10(2H,4H)-tetraone
6-ethyl-8-((3-methoxyphenyl)thio)-2,4-dimethylpyrimido[4,5-c]isoquinoline-1,3,7,10(2H,4H)-tetraone
6-ethyl-8-((3-fluorophenyl)thio)-2,4-dimethylpyrimido[4,5c]isoquinoline-1,3,7,10(2H,4H)-tetraone
8-((3-chlorophenyl)thio)-6-ethyl-2,4-dimethylpyrimido[4,5-c]isoquinoline-1,3,7,10(2H,4H)-tetraone
8-((3-bromophenyl)thio)-6-ethyl-2,4-dimethylpyrimido[4,5-c]isoquinoline-1,3,7,10(2H,4H)-tetraone
6-ethyl-2,4-dimethyl-8-(p-tolylthio)pyrimido[4,5-c]isoquinoline 1,3,7,10(2H,4H)-tetraone
6-ethyl-8-((4-methoxyphenyl)thio)-2,4-dimethylpyrimido[4,5-c]isoquinoline-1,3,7,10(2H,4H)-tetraone 6-ethyl-8-((4-fluorophenyl)thio)-2,4-dimethylpyrimido[4,5-c]isoquinoline-1,3,7,10(2H,4H)-tetraone
8-((4-chlorophenyl)thio)-6-ethyl-2,4-dimethylpyrimido[4,5-c]isoquinoline-1,3,7,10(2H,4H)-tetraone
8-((4-bromophenyl)thio)-6-ethyl-2,4-dimethylpyrimido[4,5-c]isoquinoline-1,3,7,10(2H,4H)-tetraone
6-ethyl-8-((4-hydroxyphenyl)thio)-2,4-dimethylpyrimido[4,5-c]isoquinoline-1,3,7,10(2H,4H)-tetraone
6-ethyl-8-((4-nitrophenyl)thio)-2,4-dimethylpyrimido[4,5-c]isoquinoline-1,3,7,10(2H,4H)-tetraone
8-((4-aminophenyl)thio)-6-ethyl-2,4-dimethylpyrimido[4,5-c]isoquinoline-1,3,7,10(2H,4H)-tetraone
8-((2,6-dimethoxyphenyl)thio)-6-ethyl-2,4-dimethylpyrimido[4,5-c]isoquinoline-1,3,7,10(2H,4H)-tetraone
8-((5-bromine-2-methoxyphenyl)thio)-6-ethyl-2,4-dimethylpyrimido[4,5-c]isoquinoline-1,3,7,10(2H,4H)-tetraone
8-((3,5-dichlorophenyl)thio)-6-ethyl-2,4-dimethylpyrimido[4,5-c]isoquinoline-1,3,7,10(2H,4H)-tetraone
8-(benzylthio)-6-ethyl-2,4-dimethylpyrimido[4,5-c]isoquinoline-1,3,7,10(2H,4H)-tetraone
8-((4-chlorobenzyl)thio)-6-ethyl-2,4-dimethylpyrimido[4,5-c]isoquinoline-1,3,7,10(2H,4H)-tetraone
6-ethyl-2,4-dimethyl-8-(phenylethylthio)pyrimido[4,5-c]isoquinoline-1,3,7,10(2H,4H)-tetraone
8-(benzo[d]oxazole-2-ylthio)-6-ethyl-2,4-dimethylpyrimido[4,5-c]isoquinoline-1,3,7,10(2H,4H)-tetraone
8-((2-bromo-4-chlorophenyl)thio)-6-ethyl-2,4-dimethylpyrimido[4,5-c]isoquinoline-1,3,7,10(2H,4H)-tetraone
8-((4-aminophenyl)amino)-6-ethyl-2,4-dimethylpyrimido[4,5-c]isoquinoline-1,3,7,10(2H,4H)-tetraone
6-ethyl-2,4-dimethyl-8-(phenylamino)pyrimido[4,5-c]isoquinoline-1,3,7,10(2H,4H)-tetraone
6-ethyl-8-((4-fluorophenyl)amino)-2,4-dimethylpyrimido[4,5-c]isoquinoline-1,3,7,10(2H,4H)-tetraone
8-((4-chlorophenyl)amino)-6-ethyl-2,4-dimethylpyrimido[4,5-c]isoquinoline-1,3,7,10(2H,4H)-tetraone
8-((4-bromophenyl)amino)-6-ethyl-2,4-dimethylpyrimido[4,5-c]isoquinoline-1,3,7,10(2H,4H)-tetraone
Methyl 4-((6-ethyl-2,4-dimethyl-1,3,7,10-tetraoxo-1,2,3,4,7,10-hexahydropyrimido[4,5-c]isoquinoline-8-yl)amino) benzoate.

The effective treatment dosage of pyrimido-isoquinoline-quinones derivatives represented by formula I, their hydrates, solvates or salts accepted for pharmaceutical use, can be determined by considering the specific compounds used, the method of administration, the individual, the disease, etc. However, 5-40 mg/kg body weight per day is the preferred dosage range of the pyrimido-isoquinoline-quinones derivative compound represented by formula I, taking into account that the compounds of the present invention have a high percentage of binding to albumin. The daily dose may be given once a day (once) or several times a day when properly divided into an effective daily dose. Depending on the formulation, oral administration, parenteral administration (injection) or local administration is possible. The pharmaceutical composition of the present invention may be formulated for oral administration such as tablets, powders, dry syrups, chewable tablets, granules, capsules, soft capsules, pills, drinks, sublingual tabs, etc. The composition of the invention as tablet formulations may be administered to an individual by any method or route that delivers the effective dose of the tablet with bioavailability, which may be oral. In addition, the method or route of administration may be determined according to the characteristics, stages of the target disease or other conditions. When the invention is made into tablets, these may also include excipients accepted for pharmaceutical use. The content and characteristics of the excipient can be determined by the solubility and chemical properties of the tablet chosen, the route of administration and normal pharmaceutical practice.

Pharmaceutical compositions may be prepared by combining a therapeutically effective amount of at least one compound in accordance with this invention, or a pharmaceutically acceptable acid-imbued addition salt thereof, as an active ingredient, together with conventional pharmaceutical excipients and/or additives, and by preparing unit dose forms suitable for use as an antibiotic.

In the present invention, pharmaceutically acceptable additives may include a diluent, a binder, a disintegrant, and the like.

Some examples of diluents may include microcrystalline cellulose, lactose, mannitol, calcium phosphate, and similar; some examples of binders may include povidone, hydroxypropyl cellulose (HPC), hydroxypropyl methyl cellulose (HPMC), polyvinyl alcohol (PVA), sodium carboxymethyl cellulose, and similar; and some examples of disintegrants may include crospovidone, sodium croscarmellose, sodium starch glycolate, and the like.

Other additives or vehicles for oral formulations include cellulose, calcium silicate, corn starch, sucrose, dextrose, stearic acid, magnesium stearate, calcium stearate, gelatin, talc, surfactants, suspension agents, emulsifiers and others.

The diluent can be used in an amount ranging from 20 to 95% by weight, the binder can be used in an amount ranging from 1 to 10% by weight, and the disintegrant can be used in an amount ranging from 1 to 30% by weight, based on the total weight of the composition.

For parenteral formulations such as intramuscular, intravenous, subcutaneous administration, additives or vehicles such as water, saline, glucose solution, glucose solution analogues, alcohols, glycols, ethers (e.g. polyethylene glycol 400), oils, fatty acids, fatty acid esters, glycerides, surfactants, suspension agents, emulsifiers, and others, physiological saline solutions may be used as a the preferred primary carrier.

The pH of these solutions should preferably be kept between 6.5 and 7.2 with an adequate buffer system. Formulations may also contain pharmaceutically acceptable conventional preservatives, stabilizers and surfactants.

The preferred preservatives that may be used in the pharmaceutical compositions of the present invention include, but are not limited to, benzyl alcohol, propyl paraben, methylparaben, benzalkonium chloride, chlorobutanol, thimerosal, phenylmercuric acetate and phenylmecuric nitrate. A preferred surfactant is, for example, Tween 80, but they are not limited to this alone. Similarly, various preferred vehicles may be used in the preparations of the present invention. These vehicles include, but are not limited to, propylene glycol solutions of sodium hydroxide, polyvinyl alcohol, povidone, methyl hydroxypropyl cellulose, poloxamers, carboxymethyl cellulose, hydroxyethyl cellulose and purified water.

Tonicity adjusters can be added as needed or considered convenient. These include, but are not limited to, salts, particularly sodium chloride, potassium chloride, mannitol and glycerin, or any other appropriate and acceptable tonicity adjusters.

Various buffers and mediums may be used to adjust the pH as long as the resulting preparation is ophthalmically acceptable. Consequently, buffers include acetate buffers, citrate buffers, phosphate buffers and borate buffers. Acids or bases can be used to adjust the pH of these formulations as needed.

Similarly, an antioxidant acceptable for use in the present invention includes, but is not limited to, sodium metabisulphite, sodium thiosulphate, acetylcysteine, hydroxyanisole butylated and hydroxytoluene butylated.

Other excipient components both in liquid solution and oral composition, which may be included in the preparations, are chelating agents. Among the chelating agents to be used are calcium and disodium ethylenediaminetetraacetate 5 (CaNa2EDTA), triethylenetetramine hexaacetic acid (TTHA), dihydroxyethyl ethylenediamine diacetic acid, hydroxyethyl ethylenediaminetriacetic acid (HEDTA), oxalate and its derivatives, 1,2-bis(diphenylphosphino)ethylene (DPPE), dimercaprol (BAL), diethylenetriamine pentaacetic acid (DTPA). Ethylenediaminetetraacetic acid (EDTA) is preferred, but other chelating agents may also be used instead of or in conjunction with this agent.

In this invention EDTA has a twofold function. On the one hand it is a chelating agent that tends to trap metallic particles. On the other hand, although EDTA has not been recognized as an antimicrobial agent, it is generally considered to be a "booster" of the activity of other antimicrobial agents (Brown and Richards 1965). As such, the literature has documented a synergistic or reinforcing effect common to the action of preservatives, antibiotics, and cationic surfactants, e.g., quaternary ammonium compounds (Weiser et al. 1969; Sheikh and Parker 1972; Hart 1984; Vaara 1992; Hart 1984).

Mechanistically, one of the recognized modes of EDTA action is the disruption of the lipopolysaccharide structure in the outer membrane of Gram-negative bacteria. As a result, the disruption of the membrane becomes more permeable to other agents, thus the boosting action. In addition, a combination of EDTA and lysozyme to degrade the peptidoglycan layer may result in the production of 10 spheroplasts, in which the cell wall is completely stripped away (MacGregor and Elliker 1958; Haque and Russell 1974 a, b).

One of the tests performed and covered by the present development is the combination of the agents described in formula I with EDTA, where the scope of action of this antibiotic is extended to Gram (−) bacteria. The above is demonstrated in Table IV in the experimental tests.

The ingredients are generally used in the following quantities for the various pharmaceutical compositions, without being restricted to them, and the same active ingredient may be used in other compositions:

| Raw materials | Amount (% weight/weight) |
| --- | --- |
| TABLET | |
| Granulated active ingredient | 80.0-95.0 |
| Dextrose | 0-1.0 |
| Microcrystalline cellulose (Avicel pH 10.1) | 0-3.0 |
| Starches | 0-2.0 |
| Talc | 0-1.0 |
| CAPSULES | |
| Active ingredient | 95.0-99.0 |
| Lactose | c.s.p. |
| Magnesium stearate | 5-1 |
| EMULSIONS (o/w) | |
| Active ingredient | 1.0-5.0 |
| Stearic acid | 7.0-9.0 |
| White Petrolatum | 1.0-3.0 |
| Mineral oil | 1.0-3.0 |
| Triethanolamine | c.s.p |
| Propylene Glycol | 4.0-6.0 |
| Methylparaben | 0.1-0.3 |
| Propylparaben | 0.1-0.3 |
| Sterile Distilled Water | c.s.p |
| WHITE OINTMENT | |
| Active ingredient | 8.0-12.0 |
| Mineral oil | 38.0-42.0 |
| While Petrolatum | 38.0-42.0 |
| INJECTABLE | |
| Active ingredient | 1.0-10.0 |
| Sodium Chloride | 0,9 |
| Lactic acid | 0.1-5.0 |
| Edetate Disodium | 0.1-5.0 |
| Water for Injection | c.s.p. |

This invention is further illustrated by the following non-limiting examples:

Example 1

General Procedure to Obtain 6-ethyl-2,4-dimethylpyrimido[4,5-c]isoquinoline-1,3,7,10(2H,4H)-tetraone (Intermediate Compound 1)

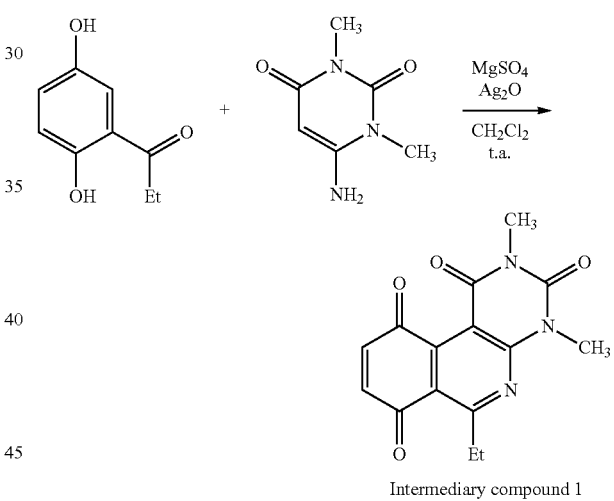

Intermediary compound 1

A solution of 1-(2,5-dihydroxyphenyl)-propan-1-one (166.6 mg, 1 mmol), 6-amino-1,3-dimethylpyrimido-2,4 (1H, 3H)-dione (201.7 mg, 1.3 mmol), MgSO4 (300.0 mg, 3 mmol), Ag2O (927.0 mg, 3 mmol) in CH2Cl2 (20 ml) is kept under agitation for 2 hours. The progress of the reaction is monitored by thin layer chromatography at 30, 60, 90 and 120 minutes. The reaction crude is vacuum filtered with filter paper and Buchner funneled celite using CH2Cl2 to entrain the product. The solution obtained from the filtration evaporates until dry. The resulting solid is purified with 30 g of Silica gel (0.040-0.063 mm) using dichloromethane: ethyl acetate=9:1 as the mobile phase. A yellow solid of 244.7 mg, 0.65 mmol is obtained with an 80% yield.

Melting point 167.6-167.9° C. HRMS (M+): m/z calculated C15H13N3O4=299.09061; found=299.09070. IR (KBr):1667.28 cm-1° C.═O (quinone); 1720.35 cm-1° C.═O (uracil). $^1$H RMN (CDCl3, 400 MHz): δ 1.41 (t, $^3$J=7.3 Hz, 3H, 6-CH$_2$CH$_3$), 3.70 (dd, $^3$J=7.2 Hz, 2H, 6-CH$_2$CH$_3$), 3.47 (s, 3H, 4-NCH3), 3.77 (s, 3H, 2-NCH3), 6.88 (d, $^3J$=10.3 Hz, $^1$H, 8-H), 7.18 (d, $^3J$=10.3 Hz, $^1$H, 9-H). $^{13}$C RMN (CDCl3, 100 MHz): δ 12.0 (6-CH$_2$CH$_3$), 29.0 (4-NCH3), 30.1 (2-NCH3), 31.5 (6-CH$_2$CH$_3$), 105.3 (10b), 121.2 (6a), 138.6 (9-C), 138.7 (8), 146.9 (10a), 150.9 (3), 152.6 (1), 158.7 (4a), 170.3 (6), 183.7 (7), 185.2 (10).

Example 2

Obtaining 6-ethyl-2,4-dimethyl-8-(phenythio)pyrimido[4,5-c]isoquinoline-1,3,7,10(2H,4H)-tetraone (2)

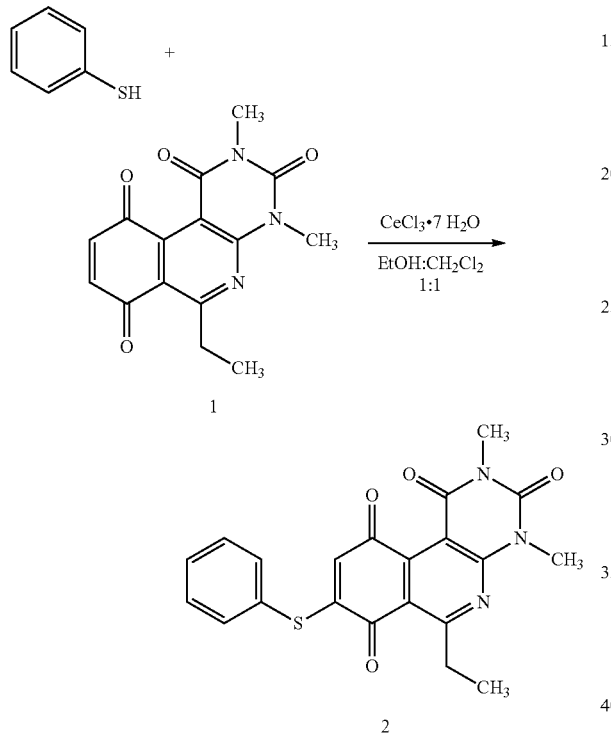

A solution of 6-ethyl-2,4-dimethylpyrimido[4,5-c]isoquinoline-1,3,7,10(2H,4H)-tetraone (1) (452.02 mg, 2.0 mmol), heptahydrated cerium (III) trichloride (0.5% mole of 1) in a mixture of CH2Cl2:MetOH=1:1 (10 ml), is added a solution of thiophenol (83.20 mg, 1.0 mmol) dissolved in CH2Cl2:MetOH=1:1 (30 ml) by dripping from a side key burette at a rate of approximately 1 ml/30 min for 16 hours. The crude reaction is purified with 50 g of Silica gel (0.040-0.063 mm) using dichloromethane:petroleum ether:ethyl acetate=9:8:1 as the mobile phase. An orange-colored solid of 196 mg, 0.48 mmol is obtained, with a 67% yield.

Melting point 179.4-180.0° C. HRMS (M+): m/z calculated C21H17N3O4S[M+]=407.09398; found=407.09400. IR (KBr): 1660.18, 1688.50 cm-1° C.═O (quinone); 1723.89 cm-1° C.═O (uracil). $^1$H RMN (CDCl3, 400 MHz): δ 1.38 (t, $^3J$=7.3 Hz, 3H, 6-CH$_2$CH$_3$), 3.42 (c, $^3J$=7.3 Hz, 2H, 6-CH$_2$CH$_3$), 3.45 (s, 3H, 4-NCH3), 3.76 (s, 3H, 2-NCH3), 6.18 (s, $^1$H, 9-H), 7.53 (m, 5H, 8-SC6H5). 13C RMN (CDCl3, 100 MHz): δ 12.1 (6-CH$_2$CH$_3$), 29.6 (4-NCH3), 30.1 (2-NCH3), 31.9 (6-CH$_2$CH$_3$), 105.8 (10a), 121.0 (6a), 127.6 (1'), 128.3 (9), 130.9 (3' and 5'), 131.1 (4'), 136.1 (2' and 6'), 147.0 (10b), 151.5 (3), 153.1 (1), 157.1 (8), 158.8 (4a), 171.0 (6), 181.2 (10), 181.7 (7).

Example 3

Obtaining 6-ethyl-2,4-dimethyl-8-(o-tolylthio)pyrimido[4,5-c]isoquinoline-1,3,7,10(2H,4H)-tetraone (3)

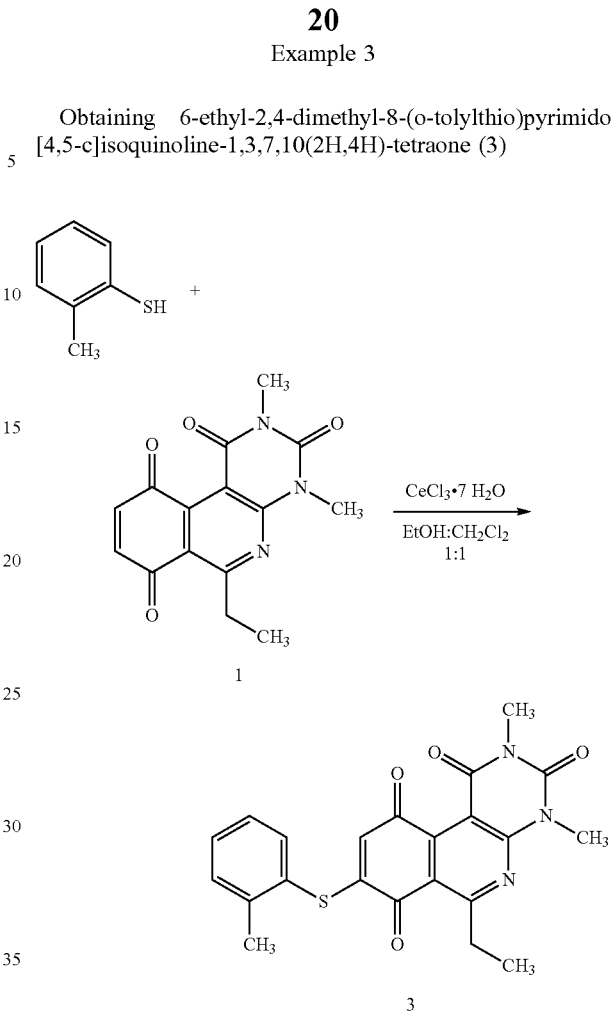

A solution of 6-ethyl-2,4-dimethylpyrimido[4,5-c]isoquinoline-1,3,7,10(2H,4H)-tetraone (1) (436.98 mg, 2.0 mmol), heptahydrated cerium (III) trichloride (0.5% mole of 1) in a mixture of CH2Cl2:MetOH=1:1 (10 ml), is added a solution of 2-methylthiophenol (90.67 mg, 1.0 mmol) dissolved in CH2Cl2:MetOH=1:1 (30 ml) by dripping from a side key burette at a rate of approximately 1 ml/30 min for 16 hours. The reaction crude is purified with 50 g of Silica gel (0.040-0.063 (mm) using dichloromethane:petroleum ether:ethyl acetate=9:10:1 as the mobile phase. An orange-colored solid of 210 mg, 0.50 mmol is obtained, with a 72% yield.

Melting point 206.0-210.9° C. HRMS (M+): m/z calculated C22H19N3O4S[M+]=421.10963; found=421.10957. IR (KBr): 1660.18, 1688.50 cm-1° C.═O (quinone); 1730.97 cm-1° C.═O (uracile).

1H RMN (CDCl3, 400 MHz): δ 1.38 (t, $^3J$=7.2 Hz, 3H, 6-CH$_2$CH$_3$), 2.43 (s, 3H, 2'-CH$_3$), 3.42 (c, $^3J$=7.3 Hz, 2H, 6-CH$_2$CH$_3$), 3.43 (s, 3H, 4-NCH3), 3.76 (s, 3H, 2-NCH3), 6.02 (s, $^1$H, 9-H), 7.32 (d, $^3J$=7.1 Hz, $^1$H, 4'), 7.42 (t, $^3J$=8.1 Hz, 2H, 5' and 3'), 7.50 (d, $^3J$=7.5 Hz, $^1$H, 6'). $^{13}$C RMN (CDCl3, 100 MHz): δ 12.1 (6-CH$_2$CH$_3$), 20.5 (2'-CH$_3$), 28.9 (4-NCH3), 30.8 (2-NCH3), 31.7 (6-CH$_2$CH$_3$), 105.7 (10a), 120.9 (6a), 126.5 (1'), 127.6 (9), 128.1 (4'), 131.5 (5'), 131.8 (3'), 136.9 (6'), 142.2 (2'), 147.5 (10b), 151.2 (3), 152.9 (1), 155.6 (8), 158.6 (4a), 170.9 (6), 181.1 (7), 181.4 (10).

Example 4

Obtaining 6-ethyl-8-(2-methoxyphenylthio)-2,4-dimethyl pyrimido[4,5-c]isoquinoline-1,3,7,10(2H,4H)-tetraone (4)

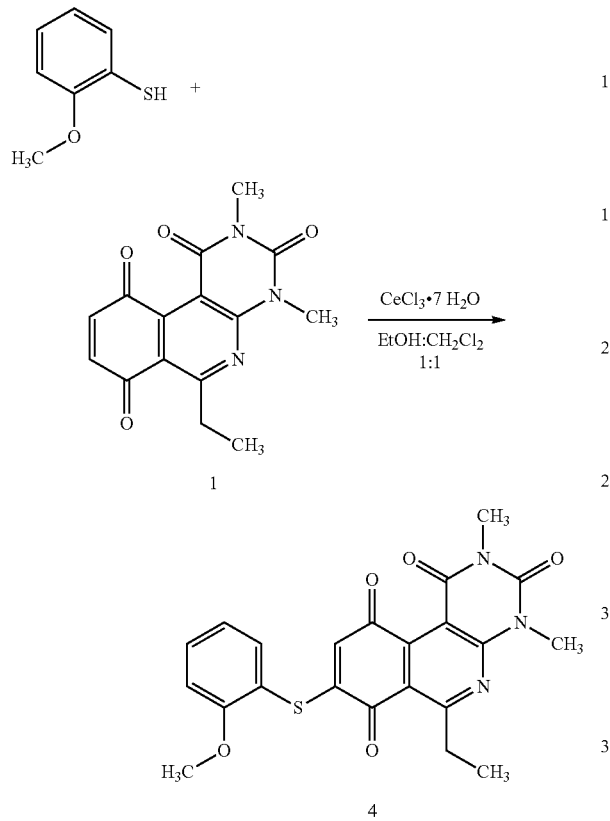

A solution of 6-ethyl-2,4-dimethylpyrimido[4,5-c]isoquinoline-1,3,7,10(2H,4H)-tetraone (1) (420.99 mg, 2.0 mmol), heptahydrated cerium(III) trichloride (0.5% mole of 1) in a mixture of CH2Cl2:MetOH=1:1 (10 ml), is added a solution of 2-methoxythiophenol (90.67 mg, 1.0 mmol) dissolved in CH2Cl2:MetOH=1:1 (30 ml) by dripping from a side key burette at a rate of approximately 1 ml/30 min for 16 hours. The reaction crude is purified with 80 g of Silica gel (0.040-0.063 (mm) using dichloromethane:petroleum ether: ethyl acetate=9:6:1 as the mobile phase. An orange-colored solid of 211 mg, 0.48 mmol is obtained, with a 72% yield.

Melting point 172.3(d)° C. HRMS (M+): m/z calculated $C_{22}H_{19}N_3O_5S$ [M+]=437.10454; found=437.10450. IR (KBr): 1660.18, 1688.50 cm$^{-1}$ C.=O (quinone); 1727.43 cm$^{-1}$ C.=O (uracile). $^1$H RMN (CDCl$_3$, 400 MHz): δ 1.40 (t, $^3$J=7.3 Hz, 3H, 6-CH$_2$CH$_3$), 3.45 (c, $^3$J=7.2 Hz, 2H, 6-CH$_2$CH$_3$), 3.46 (s, 3H, 4-NCH$_3$), 3.78 (s, 3H, 2'-OCH$_3$), 3.89 (s, 3H, 2-NCH$_3$), 6.13 (s, $^1$H, 9-H), 7.08 (t, $^3$J=8.8 Hz, 2H, 5' y 3'), 7.54 (dd, $^3$J=7.1 Hz, 2H, 4' and 6'). $^{13}$CRMN (CDCl$_3$, 100 MHz): δ 12.2 (6-CH$_2$CH$_3$), 29.0 (4-NCH$_3$), 30.2 (2-NCH$_3$), 31.6 (6-CH$_2$CH$_3$), 56.2 (2'-OCH$_3$), 105.5 (10a), 112.1 (3'), 114.6 (6a), 120.9 (1'), 122.1 (5'), 127.6 (9), 133.1 (4'), 137.6 (6'), 147.4 (2'), 151.2 (10b), 152.8 (3), 154.8 (1), 158.6 (8), 160.1 (4a), 170.7 (6), 181.2 (10), 181.4 (7).

Example 5

Obtaining 6-ethyl-8-((2-fluorophenyl)thio)-2,4-dimethyl pyrimido[4,5-c]isoquinoline-1,3,7,10(2H, 4H)-tetraone

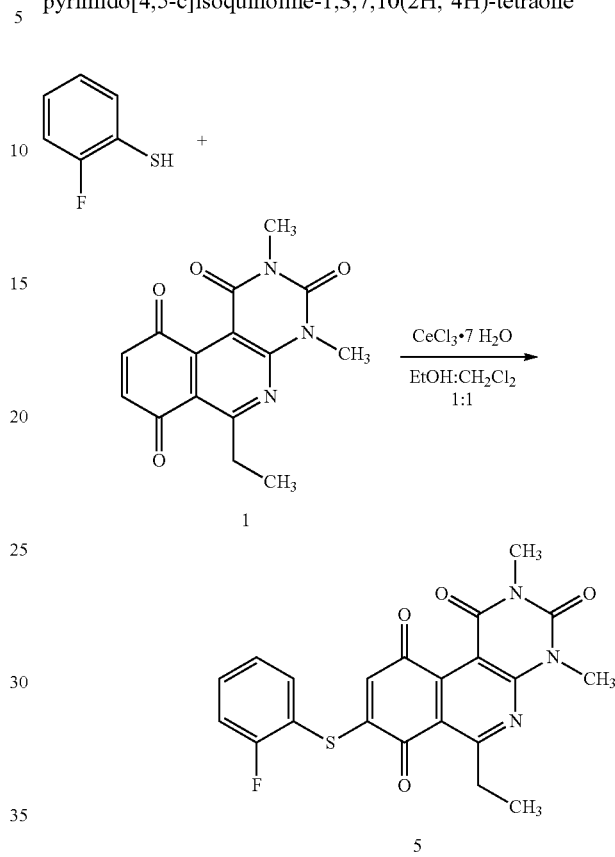

A solution of 6-ethyl-2,4-dimethylpyrimido[4,5-c]isoquinoline-1,3,7,10(2H,4H)-tetraone (1) (432.91 mg, 2.0 mmol), heptahydrated cerium (III) trichloride (0.5% mole of 1) in a mixture of CH2Cl2:MetOH=1:1 (10 ml), is added a solution of 2-fluorothiophenol (92.6 mg, 1.0 mmol) dissolved in CH2Cl2:MetOH=1:1 (30 ml) by dripping from a side key burette at a rate of approximately 1 ml/30 min for 16 hours. The reaction crude is purified with 80 g of Silica gel (0.040-0.063 (mm) using dichloromethane:petroleum ether: ethyl acetate=9:14:2 as the mobile phase. An orange-colored solid of 255 mg, 0.60 mmol is obtained, with an 87% yield.

Melting point 218.4(d)° C. HRMS (M+): m/z calculated $C_{21}H_{16}FN_3O_4S$ [M+]=425.08455; found=425.08460. IR (KBr): 1660.18, 1684.96 cm$^{-1}$ C.=O (quinone); 1727.43 cm$^{-1}$ C.=O (uracile). $^1$H RMN (CDCl$_3$, 400 MHz): δ 1.38 (t, $^3$J=7.3 Hz, 3H, 6-CH$_2$CH$_3$), 3.43 (c, $^3$J=7.2 Hz, 2H, 6-CH$_2$CH$_3$), 3.44 (s, 3H, 4-NCH$_3$), 3.76 (s, 3H, 2-NCH$_3$), 6.13 (s, $^1$H, 9-H), 7.29 (dd, $^3$J=8.2 Hz, 2H, 5' and 3'), 7.52 (t, $^3$J=6.7 Hz, 2H, 4' and 6'). $^{13}$C RMN (CDCl$_3$, 100 MHz): δ 12.5 (6-CH$_2$CH$_3$), 29.5 (4-NCH$_3$), 30.6 (2-NCH$_3$), 32.1 (6-CH$_2$CH$_3$), 105.7(10a), 114.9 (d, $^3$J=18.6 Hz, 1'), 117.6 (d, $^3$J=22.3 Hz, 3'), 120.9 (6a), 126.3 (d, $^3$J=3.9 Hz, 5'), 128.4 (9), 133.9 (d, $^3$J=8.1 Hz, 4'), 137.9 (6'), 147.6 (10b), 151.5 (3), 153.2 (1), 154.4 (8), 158.8 (4a), 163.1 (d, $^3$J=251.5 Hz, 2'), 171.2 (6), 181.1 (10), 181.6 (7).

Example 6

Obtaining 8-((2-chlorophenyl)thio)-6-ethyl-2,4-dimethylpyrimido[4,5-c]isoquinoline-1,3,7,10(2H,4H)-tetraone (6)

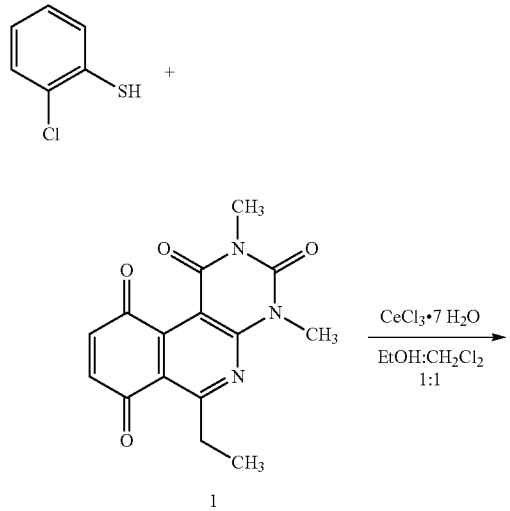

Example 7

Obtaining 8-((2-bromophenyl)thio)-6-ethyl-2,4-dimethylpyrimido[4,5-c]isoquinoline-1,3,7,10(2H,4H)-tetraone (7)

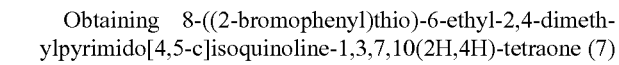

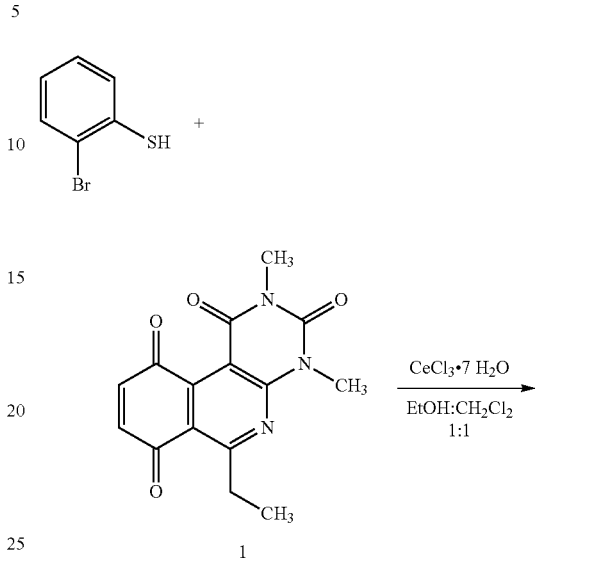

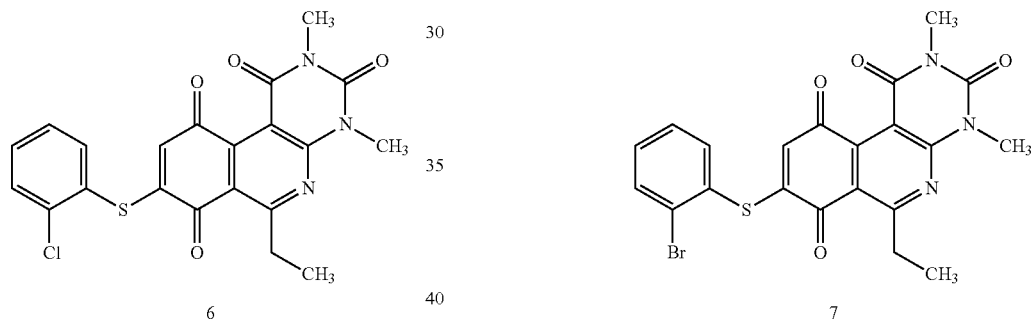

A solution of 6-ethyl-2,4-dimethylpyrimido[4,5-c]isoquinoline-1,3,7,10(2H,4H)-tetraone (1) (416.78 mg, 2.0 mmol), heptahydrated cerium(II) trichloride (0.5% mole of 1) in a mixture of CH2Cl2:MetOH=1:1 (10 ml), is added a solution of 2-chlorothiophenol (100.70 mg, 1.0 mmol) dissolved in CH2Cl2:MetOH=1:1 (30 ml) by dripping from a side key burette at a rate of approximately 1 ml/30 min for 16 hours. The reaction crude is purified with 60 g of Silica gel (0.040-0.063 mm) using dichloromethane:petroleum ether: ethyl acetate=9:14:2 as the mobile phase. An orange-colored solid of 240 mg, 0.54 mmol is obtained, with an 82% yield.

Melting point 220.8 (d)° C. HRMS (M+): m/z calculated $C_{21}H_{16}ClN_3O_4S$ [M+]=441.05500; found=441.05521. IR (KBr): 1660.18, 1677.88 cm$^{-1}$C=O (quinone); 1720.35 cm$^{-1}$C=O (uracil). $^1$H RMN (CDCl$_3$, 400 MHz): δ 1.38 (t, $^3$J=7.3 Hz, 3H, 6-CH$_2$CH$_3$), 3.43 (c, $^3$J=7.2 Hz, 2H, 6-CH$_2$CH$_3$), 3.44 (s, 3H, 4-NCH$_3$), 3.76 (s, 3H, 2-NCH$_3$), 6.07 (s, $^1$H, 9-H), 7.41 (t, $^3$J=7.5 Hz, $^1$H, 5'), 7.50 (t, $^3$J=7.7 Hz, $^1$H, 4'), 7.64 (m, 2H, 3' and 6'). $^{13}$C RMN (CDCl$_3$, 100 MHz): δ 12.1 (6-CH$_2$CH$_3$), 29.1 (4-NCH$_3$), 30.2 (2-NCH$_3$), 32.7 (6-CH$_2$CH$_3$), 105.9 (10a), 120.9 (6a ), 126.9 (1'), 128.3 (9), 128.9(5'), 131.6 (3'), 132.9 (4'), 138.4 (6'), 140.3 (2'), 147.6 (10b), 151.5 (3), 153.2 (1), 154.2 (8), 158.8 (4a), 171.2 (6), 181.1 (10), 181.6 (7).

A solution of 6-ethyl-2,4-dimethylpyrimido[4,5-c]isoquinoline-1,3,7,10(2H,4H)-tetraone (1) (378.69 mg, 2.0 mmol), heptahydrated cerium(III) trichloride (0.5% mole of 1) in a mixture of CH2Cl2:MetOH=1:1 (10 ml), is added a solution of 2-bromoothiophenol (119.62 mg, 1.0 mmol) dissolved in CH2Cl2:MetOH=1:1 (30 ml) by dripping from a side key burette at a rate of approximately 1 ml/30 min for 16 hours. The reaction crude is purified with 65 g of Silica gel (0.040-0.063 mm) using dichloromethane:petroleum ether: ethyl acetate=9:12:1 as the mobile phase. An orange-colored solid of 241 mg, 0.49 mmol is obtained, with an 82% yield.

Melting point 208.3 (d)° C. HRMS (M+): m/z calculated $C_{21}H_{16}BrN_3O_4S$ [M+]=485.00449; found=485.00455. IR (KBr): 1660.18, 1688.50 cm$^{-1}$° C.=O (quinone); 1730.97 cm$^{-1}$° C.=O(uracile). $^1$H RMN (CDCl$_3$, 400 MHz): δ 1.37 (t, $^3$J=7.3 Hz, 3H, 6-CH$_2$CH$_3$), 3.41 (c, $^3$J=7.2 Hz, 2H, 6-CH$_2$CH$_3$), 3.42 (s, 3H, 4-NCH$_3$), 3.76 (s, 3H, 2-NCH$_3$), 6.06 (s, $^1$H, 9-H), 7.41 (dt, $^3$J=7.9 Hz, 2H, 5' and 4'), 7.64 (d, $^3$J=8.8 Hz, $^1$H, 6'), 7.79 (d, $^3$J=7.8 Hz, $^1$H, 3'). $^{13}$C RMN (CDCl$_3$, 100 MHz): δ 12.1 (6-CH$_2$CH$_3$), 29.1 (4-NCH$_3$), 30.1 (2-NCH$_3$), 31.7 (6-CH$_2$CH$_3$), 105.6 (10a), 120.7 (6a ), 127.9 (9), 128.9 (1'), 129.3 (5'), 130.8 (2'), 132.5 (4'), 134.7 (3'), 138.0 (6'), 147.3 (10b), 151.2 (3), 152.9 (1), 154.1 (8), 158.5 (4a), 170.9 (6), 180.7 (10), 181.2(7).

Example 8

Obtaining 6-ethyl-2,4-dimethyl-8-(m-tolylthio)pyrimido[4,5c]isoquinoline-1,3,7,10(2H,4H)-tetraone (8)

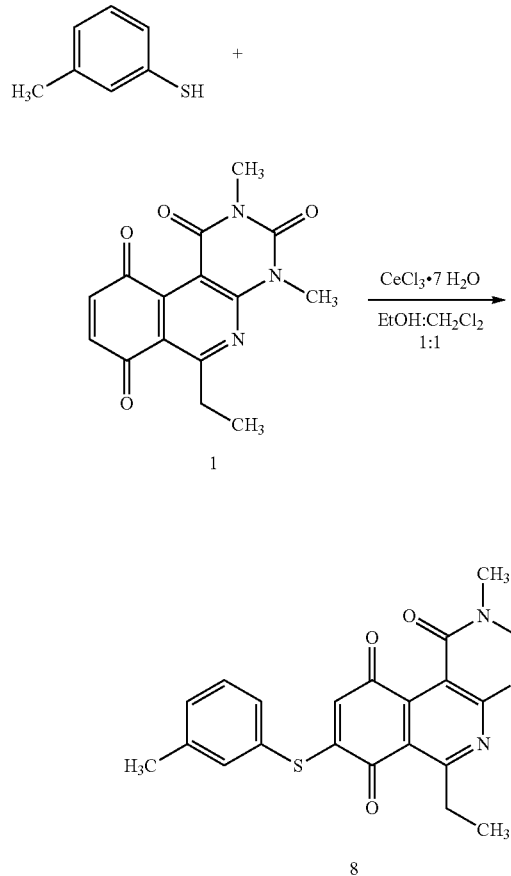

A solution of 6-ethyl-2,4-dimethylpyrimido[4,5-c]isoquinoline-1,3,7,10(2H,4H)-tetraone (1) (452.02 mg, 2.0 mmol) and heptahydrated cerium(III) trichloride (0.5% mole of 1) in a mixture of CH2Cl2:MetOH=1:1 (10 ml), is added a solution of 3-methylthiophenol (83.20 mg, 1.0 mmol) dissolved in CH2Cl2:MetOH=1:1 (30 ml) by dripping from a burette at a rate of approximately 1 ml/30 min for 16 hours. The reaction crude is purified with 50-90 g of 0.063-0.2 mm Silica gel using a suitable proportion of petroleum ether, dichloromethane and ethyl acetate as the mobile phase. An orange-colored solid of 199 mg, 0.47 mmol is obtained, with a 47% yield.

Melting point 162.0-163.0° C. HRMS (M+): m/z calculated $C_{22}H_{19}N_3O_4S$ [M+]=421.10963; found=421.10960. IR (KBr): 1561 cm$^{-1}$ ° C.=O (quinone); 1661, 1682 cm$^{-1}$ ° C.=O (uracile). $^1$H RMN (CDCl3, 400 MHz): δ 1.37 (t, $^3$J=7.2 Hz, 3H, 6-CH2CH3), 2.41 (s, 3H, 3'-CH3), 3.40(c, $^3$J=7.2 Hz, 2H, 6-CH2CH3), 3.44 (s, 3H, 4-NCH3), 3.76 (s, 3H, 2-NCH3), 6.19 (s, $^1$H, 9-H), 7.33 (m, 3H, 2', 5' y 6'), 7.42-7.37 (m, $^1$H, 4'). $^{13}$C RMN (CDCl3, 100 MHz): δ 12.2 (6-CH2CH3), 21.3 (3'-CH3), 29.1 (4-NCH3), 30.2 (2-NCH3), 31.7(6-CH2CH3), 105.5 (10a), 120.6 (6a ), 126.9 (1'), 127.9 (9), 130.3 (4'), 131.6 (5'), 132.7 (6'), 136.1 (2'), 140.6 (3'), 147.4 (10b), 151.1 (3), 152.8 (1), 156.9 (8), 158.5 (4a), 170.8 (6), 180.9 (7), 181.4 (10).

Example 9

Obtaining 6-ethyl-8-(3-methoxythiophenyl)-2,4-dimethylpyrimido[4,5-c]isoquinoline-1,3,7,10(2H,4H)-tetraone (9)

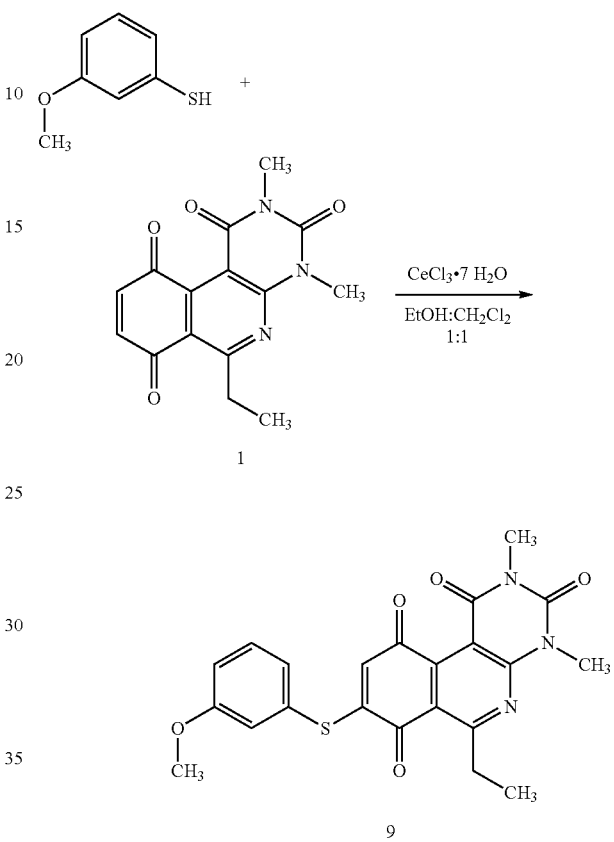

A solution of 6-ethyl-2,4-dimethylpyrimido[4,5-c]isoquinoline 1,3,7,10(2H,4H)-tetraone (1) (598.56 mg, 2.0 mmol) and heptahydrated cerium(III) trichloride (0.5% mole of 1) in a mixture of CH2Cl2:MetOH=1:1 (10 ml), is added a solution of 3-methoxythiophenol (140.20 mg, 1.0 mmol) dissolved in CH2Cl2:MetOH=1:1 (30 ml) by dripping from a burette at a rate of approximately 1 ml/30 min for 16 hours. The reaction crude is purified with 50-90 g of 0.063-0.2 mm Silica gel using an appropriate proportion of petroleum ether, dichloromethane and ethyl acetate as the mobile phase. An orange-colored solid of 288.7 mg, 0.66 mmol is obtained, with a 66% yield.

Melting point 179.5-180.5° C. HRMS (M+): m/z calculated $C_{22}H_{19}N_3O_5S$ [M+]=437.10454; found=437.10449. IR (KBr): 1560, 1579 cm$^{-1}$ ° C.=O (quinone); 1670 cm$^{-1}$ ° C.=O (uracile). $^1$H RMN (CDCl3, 400 MHz): δ 1.37 (t, $^3$J=7.2 Hz, 3H, 6-CH2CH3), 3.40(c, $^2$J=7.2 Hz, 2H, 6-CH2CH3), 3.44 (s, 3H, 4-NCH3), 3.76 (s, 3H, 3'-OCH3), 3.85 (s, 3H, 2-NCH3), 6.23 (s, 1H, 9-H), 7.07-7.02 (m, 2H, 2' and 6'), 7.12 (m 1H, 4'), 7.42 (t, $^3$J=7.7 Hz, 1H, 5'). $^{13}$C RMN (CDCl3, 100 MHz): δ 12.2 (6-CH2CH3), 29.1 (4-NCH3), 30.2 (2 NCH3), 31.7 (6-CH2CH3), 55.5 (3'-OCH3), 105.5 (10a), 116.7 (4'), 120.6 (6a ), 120.7 (2'), 127.7 (6'), 128.0 (1'), 128.1 (9), 131.1 (5'), 147.3 (10b), 151.5(3) 152.8 (1), 156.06 (8), 158.4 (4a), 160.8 (3'), 170.7 (6), 180.8 (7), 181.4 (10).

Example 10

Obtaining 6-ethyl-8-(3-fluorothiophenyl)-2,4-dimethylpyrimido[4,5-c]isoquinoline-1,3,7,10(2H,4H)-tetraone (10)

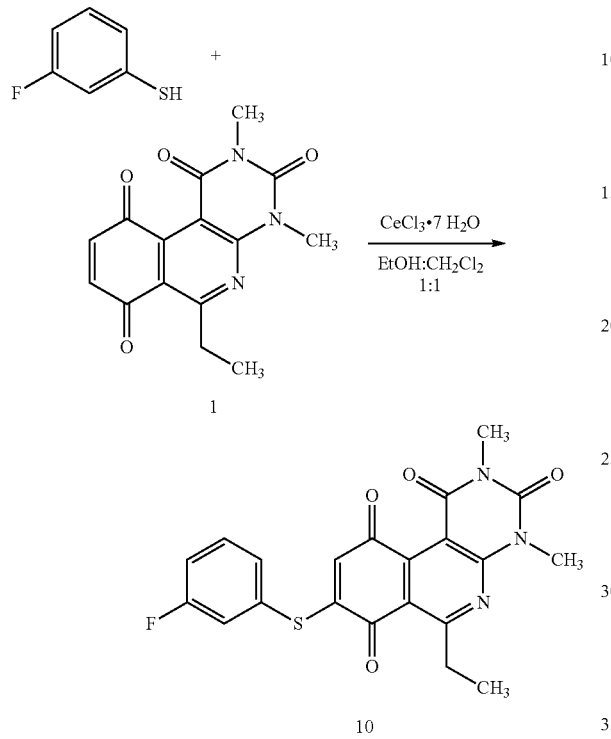

A solution of 6-ethyl-2,4-dimethylpyrimido[4,5-c]isoquinoline-1,3,7,10(2H,4H)-tetraone (1) (589.56 mg, 2.0 mmol) and heptahydrated cerium(III) trichloride (0.5% mole of 1) in a mixture of CH2Cl2:MetOH=1:1 (10 ml), is added a solution of 3-fluorophenol (128.17 mg, 1.0 mmol) dissolved in CH2Cl2:MetOH=1:1 (30 ml) by dripping from a burette at a rate of approximately 1 ml/30 min for 16 hours. The reaction crude is purified with 50-90 g of 0.063-0.2 mm Silica gel using an appropriate proportion of petroleum ether, dichloromethane and ethyl acetate as the mobile phase. An orange-colored solid of 302.1 mg, 0.71 mmol is obtained, with a 71% yield.

Melting point 170-171° C. HRMS (M+): m/z calculated $C_{21}H_{16}FN_3O_4S$ [M+]=425.08455; found=425.08457. IR (KBr): 1563 cm$^{-1o}$ C.=O (quinone); 1667, 1683 cm$^{-1o}$ C.=O en 1 y 3 (uracile). $^1$H RMN (CDCl$_3$, 400 MHz): δ 1.37 (t, $^3$J=7.3 Hz, 3H, 6-CH$_2$CH$_3$), 3.42 (c, $^3$J=7.2 Hz, 2H, 6-CH$_2$CH$_3$), 3.44 (s, 3H, 4-NCH$_3$), 3.76 (s, 3H, 2-NCH$_3$), 6.21 (s, 1H, 9-H), 7.26 (d, $^3$J=8.4 Hz, 2H, 4' and 6'), 7.35 (d, J=7.6 Hz, 1H, 2'), 7.51 (c, J=7.5 Hz, 1H, 5'). $^{13}$C RMN (CDCl$_3$, 100 MHz): δ 12.4 (6-CH$_2$CH$_3$), 29.4 (4-NCH$_3$), 30.5 (2-NCH$_3$), 32.1 (6-CH$_2$CH$_3$), 105.8 (10a), 118.16 (d, 1C, $^1$J=20.9 Hz, 3'), 120.8 (6a ), 122.66 (d, 1C $^1$J=22.1 Hz, 2') 128.4 (9), 129.25 (d, 1C $^1$J=7.6 Hz, 1'), 131.76 (dd, 1C $^1$J=34.4, 5.7 Hz, 4') 147.5 (10b), 151.4 (3), 153.1 (1), 156.1 (8), 158.7 (4a), 162.3 (6?), 164.8 (5') 171.2 (6), 180.9 (7), 181.6 (10).

Example 11

Obtaining 8-(3-chlorothiophenyl)-6-ethyl-2,4-dimethylpyrimido[4,5-c]isoquinoline-1,3,7,10(2H,4H)-tetraone (11)

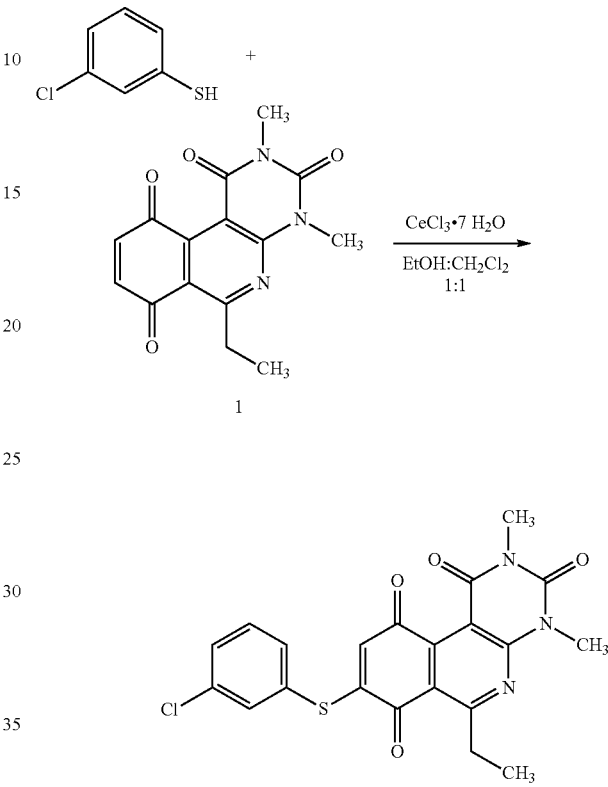

A solution of 6-ethyl-2,4-dimethylpyrimido[4,5-c]isoquinoline-1,3,7,10(2H, 4H)-tetraone (1) (598.6 mg, 2.0 mmol) and heptahydrated cerium(III) trichloride (0.5% mole of 1) in a mixture of CH2Cl2:MetOH=1:1 (10 ml), is added a solution of 3-chlorothiophenol (144.62 mg, 1.0 mmol) dissolved in CH2Cl2:MetOH=1:1 (30 ml) by dripping from a burette at a rate of approximately 1 ml/30 min for 16 hours. The reaction crude is purified with 50-90 g of 0.063-0.2 mm Silica gel using a suitable proportion of petroleum ether, dichloromethane and ethyl acetate as the mobile phase. An orange-colored solid of 256.3 mg, 0.58 mmol is obtained, with a 58% yield.

Melting point 156.1-157.1° C. HRMS (M+): m/z calculated $C_{21}H_{16}ClN_3O_4S$ [M+]=441.05500; found=441.05514. IR (KBr): 1558 cm$^{-1o}$ C.=O (quinone); 1662, 1681 cm$^{-1o}$ C.=O (uracile). 1H RMN (CDCl$_3$, 400 MHz): δ 1.37 (t, $^3$J=7.3 Hz, 3H, 6-CH$_2$CH$_3$), 3.41 (c, $^2$J=7.2 Hz, 2H, 6-CH$_2$CH$_3$), 3.44 (s, 3H, 4-NCH$_3$), 3.76 (s, 3H, 2-NCH$_3$), 6.21 (s, 1H, 9-H), 7.47 (c, $^2$J=Hz, 2H, 6' and 5'), 7.52 (d, $^2$J=7.1 Hz, 1H, 4') 7.55 (s, 1H, 2'). $^{13}$C RMN (CDCl$_3$, 100 MHz): δ 12.1 (6-CH$_2$CH$_3$), 29.1 (4-NCH$_3$), 30.2 (2-NCH$_3$), 31.8(6-CH$_2$CH$_3$), 105.5 (10a), 120.4 (6a ), 128.1 (9), 129.1 (3') 131.1 (6') 131.5 (4'), 133.9 (5'), 135.4 (2'), 136(3') 147.2 (10b), 151.1 (3), 152.8 (1), 155.8 (8), 158.4 (4a), 170.9 (6), 180.5 (7), 181.3 (10).

Example 12

Obtaining 8-(3-bromothiophenyl)-6-ethyl-2,4-dimethylpyrimido[4,5-c]isoquinoline-1,3,7,10(2, 4H)-tetraone (12)

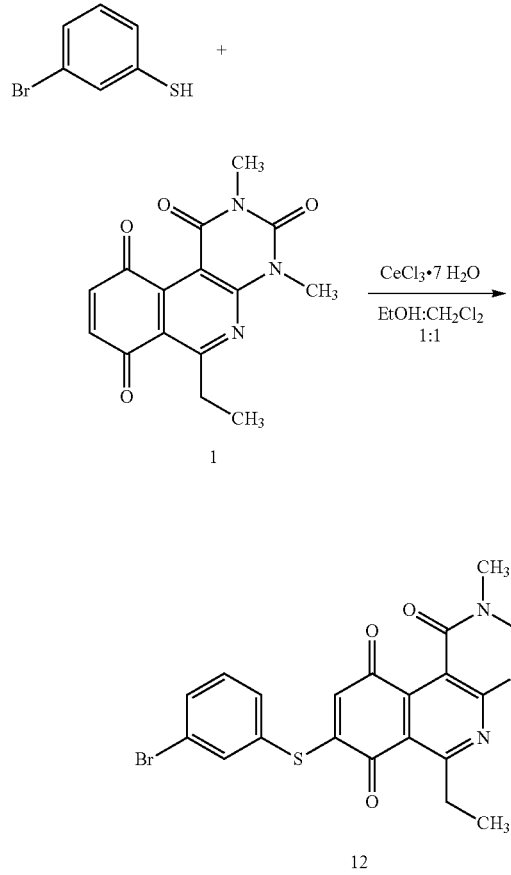

A solution of 6-ethyl-2,4-dimethylpyrimido[4,5-c]isoquinoline-1,3,7,10(2H,4H)-tetraone (1) (598.6 mg, 2.0 mmol) and heptahydrated cerium (III) trichloride (0.5% mole of 1) in a mixture of CH2Cl2:MetOH-1:1 (10 ml), is added a solution of 3-bromothiophenol (189.07 mg, 1.0 mmol) dissolved in CH2Cl2:MetOH-1:1 (30 ml) by dripping from a burette at a rate of approximately 1 ml/30 min for 16 hours. The reaction crude is purified with 50-90 g of 0.063-0.2 mm Silica gel using an appropriate proportion of petroleum ether, dichloromethane and ethyl acetate as the mobile phase. An orange-colored solid of 398.8 mg, 0.82 mmol is obtained, with an 82% yield.

Melting point 138.3-139.3° C. HRMS (M+): m/z calculated $C_{21}H_{16}BrN_3O_4S$ [M+]=485.00449; found=485.00453. IR (KBr): 1559 cm$^{-1}$° C.=O (quinone); 1668 cm$^{-1}$° C.=O (uracile). $^1$H RMN (CDCl$_3$, 400 MHz): δ 1.3 (t, $^3J$=7.3 Hz, 3H, 6-CH$_2$CH$_3$), 3.43-3.38 (c, $^2J$=Hz, 2H, 6-CH$_2$CH$_3$), 3.44 (s, 3H, 4-NCH$_3$), 3.76 (s, 3H, 2-NCH$_3$), 6.21 (s, 1H, 9-H), 7.47 (c, $^2J$=Hz, 2H, 4' and 5'), 7.52 (d, J=7.1 Hz, 1H, 6') 7.55 (s, 1H, 2'). $^{13}$C RMN (CDCl$_3$, 100 MHz): δ 12.5 (6-CH$_2$CH3), 29.4 (4-NCH$_3$), 30.5 (2-NCH$_3$), 32.1 (6-CH$_2$CH$_3$), 105.8 (10a), 120.7 (6a ), 124.2 (1'), 128.5 (9), 129.7 (3'), 132.0 (5'), 134.3 (6'), 134.6 (4'), 138.5 (2'), 147.5 (10b) 151.4 (3), 153.1 (1), 156.1 (8) 158.7 (4a), 171.2 (6), 180.8 (7), 181.6 (10).

Example 13

Obtaining 6-ethyl-2,4-dimethyl-8-(p-tolylthio)pyrimido [4,5-c]isoquinoline-1,3,7,10(2H,4H)-tetraone (13)

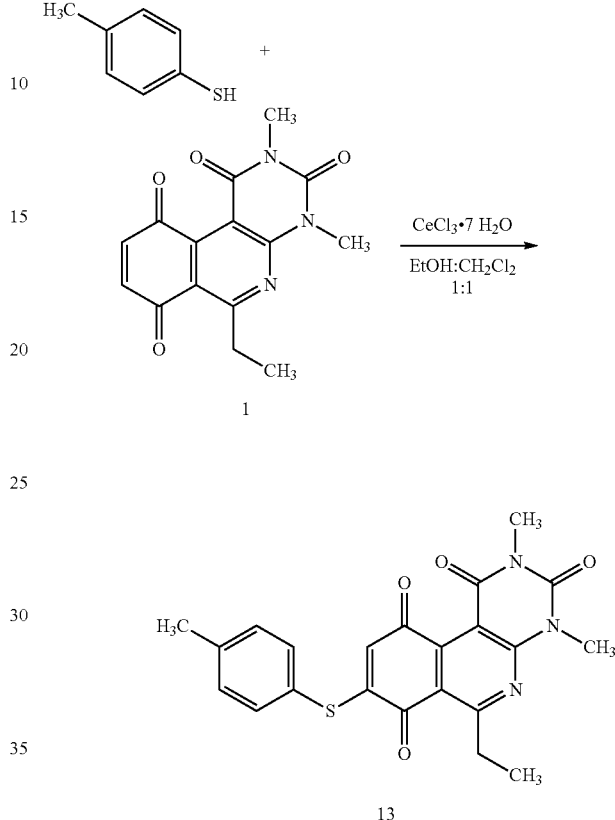

A solution of 6-ethyl-2,4-dimethylpyrimido[4,5-c]isoquinoline-1,3,7,10(2H,4H)-tetraone (1) (300.13 mg, 2.1 mmol), heptahydrated cerium (III) trichloride (5% mole of 1) in a mixture of CH2Cl2:MetOH=3.5:5 (8 ml), is added a solution of 4-methylthiophenol (60.8 mg, 1.0 mmol) dissolved in CH2Cl2:MetOH=3.5:5 (34 ml) by dripping from a side key burette at a rate of approximately 1 ml/30 min for 14 hours. The reaction crude is purified with 50 g of silica gel (0.040-0.063 mm) using petroleum ether:dichloromethane: ethyl acetate=1.5:0.5:0.5 as the mobile phase. An orange-colored solid of 174.5 mg, 0.41 mmol is obtained, with an 87.5% yield.

Melting point 191.0-192.3° C. HRMS (M+): m/z calculated $C_{22}H_{19}N_3O_4S$ [M+]=421.10963; found=421.10954. IR (KBr): 1662.34, 1687.48 cm$^{-1}$° C.=O (quinone); 1725.98 cm$^{-1}$° C.=O (uracile). $^1$H RMN (CDCl$_3$, 400 MHz): δ 1.37 (t, $^3J$=7.3 Hz, 3H, 6-CH$_2$CH$_3$), 2.42 (s, 3H, 4'-CH$_3$), 3.42 (c, $^3J$=7.3 Hz, 2H, 6-CH$_2$CH$_3$), 3.43 (s, 3H, 4-NCH$_3$), 3.75 (s, 3H, 2-NCH$_3$), 6.17 (s, 1H, 9-H), 7.31 (d, $^3J$=8.0 Hz, 2H, 3' y 5'), 7.40 (d, $^3J$=8.0 Hz, 2H, 2' y 6'). $^{13}$C RMN (CDCl$_3$, 100 MHz): δ 12.3 (6-CH$_2$CH$_3$), 21.5 (4'-CH$_3$), 29.2 (4-NCH$_3$), 30.3 (2-NCH$_3$), 31.8 (6-CH$_2$CH$_3$), 105.5(10b), 120.7 (7a), 123.6 (1'), 127.9 (9), 131.4 (2C, 3' y 5'), 135.7 (2C, 2' y 6'), 141.4 (4'), 147.5 (10a), 151.2 (3), 152.8 (1), 157.2(8), 158.8 (4a), 171.1 (6), 181.3 (7), 181.8 (10).

Example 14

Obtaining 6-ethyl-8-(4-methoxythiophenyl)-2,4-dimethylpyrimido[4,5-c]isoquinoline-1,3,7,10(2H,4H)-tetraone (14)

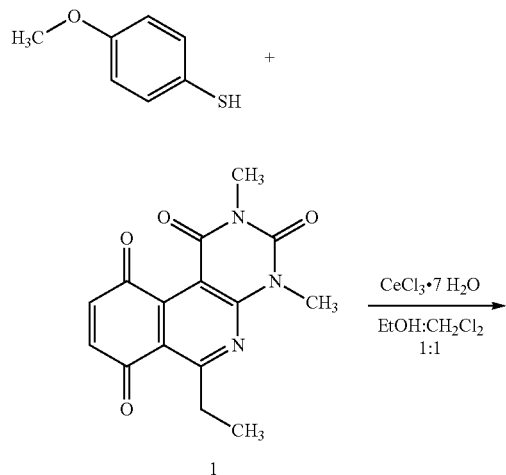

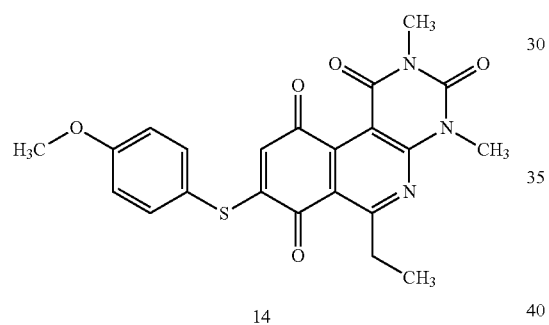

A solution of 6-ethyl-2,4-dimethylpyrimido[4,5-c]isoquinoline-5 1,3,7,10(2H,4H)-tetraone (1) (429.4 mg, 2.1 mmol), heptahydrated cerium(III) trichloride (0.5% mole of 1) in a mixture of CH2Cl2:MetOH=3.5:5 (8 ml), is added a solution of 4-methoxythiophenol (95.03 mg, 1.0 mmol) by dripping in CH2Cl2:MetOH=3.5:5 (34 ml) from a side key burette at a rate of approximately 1 ml/30 min this for 14 hours. The reaction crude is purified with 60 g of silica gel (0.040-0.063 mm) using petroleum ether:dichloromethane: ethyl acetate=1.5:1.5:0.5 as the mobile phase. A reddish-colored solid of 163 mg, 0.37 mmol is obtained, with an 82% yield.

Melting point 198.9-201.5° C. HRMS (M+): m/z calculated $C_{22}H_{19}N_3O_5S$ [M+]=437.10454; found=437.10454. IR (KBr): 1662.34, 1689.34 cm$^{-1o}$ C.=O (quinone); 1725.98 cm$^{-1o}$ C.=O (uracile). $^1$H RMN (CDCl$_3$, 400 MHz): δ 1.36 (t, $^3$J=7.3 Hz, 3H, 6-CH$_2$CH$_3$), 3.41 (c, $^3$J=7.2 Hz, 2H, 6-CH$_2$CH$_3$), 3.43 (s, 3H, 4-NCH$_3$), 3.75 (s, 3H, 4'-OCH$_3$), 3.86 (s, 3H, 2-NCH$_3$), 6.15 (s, 1H, 9-H), 7.23 (dd, $^{3,4}$J=165.7, 8.7 Hz, 4H). $^{13}$C RMN (CDCl$_3$, 100 MHz): δ 12.3 (6-CH$_2$CH$_3$), 29.2 (4-NCH$_3$), 30.3 (2-NCH$_3$), 31.8 (6-CH$_2$CH$_3$), 55.7 (4'-OCH$_3$), 105.5 (10b), 116.5, 117.3 (1'), 120.7 (6a ), 127.9 (9), 137.6, 147.5 (10a), 151.2 (3), 152.8 (1), 157.6 (8), 158.5 (4a), 161.7 (4'), 171.1 (6), 181.4 (7), 181.8 (10).

Example 15

Obtaining 6-ethyl-8-(4-fluorothiophenyl)-2,4-dimethylpyrimido[4,5-c]isoquinoline-1,3,7,10(2H, 4H)-tetraone (15)

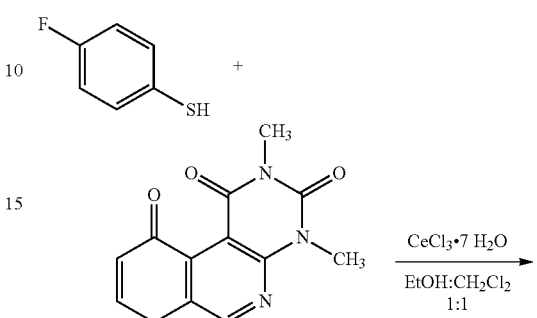

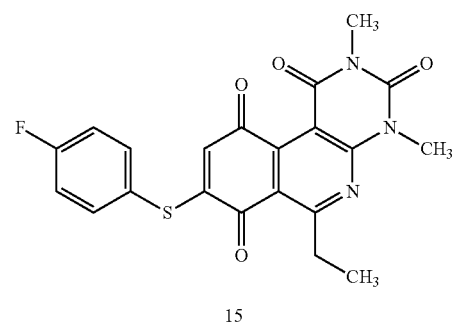

A solution of 6-ethyl-2,4-dimethylpyrimido[4,5-c]isoquinoline-1,3,7,10(2H,4H)-tetraone (1) (424.42 mg, 2.1 mmol), heptahydrated cerium(III) trichloride (0.5% mole of 1) in a mixture of CH2Cl2:MetOH=3.5:5 (8 ml), is added a solution of 4-fluoroethiophenol (128.17 mg, 1.0 mmol) dissolved in CH2Cl2:MetOH-3.5:5 (34 ml) by dripping from a side key burette at a rate of approximately 1 ml/30 min for 14 hours. The reaction crude is purified with 65 g of silica gel (0.040-0.063 mm) using petroleum ether:dichloromethane: ethyl acetate=3.0:0.5:0.5 as the mobile phase. An orange-colored solid of 122.1 mg, 0.28 mmol is obtained, with a 61.1% yield.

Melting point 194.9-195.4° C. HRMS (M+): m/z calculated $C_{21}H_{16}FN_3O_4S$ [M+]=425.08455; found=425.08462. IR (KBr): 1660.41, 1675.84 cm$^{-1o}$ C.=O (quinone); 1720.19 cm$^{-1o}$ C.=O (uracile). $^1$H RMN (CDCl$_3$, 400 MHz): δ 1.37 (t, $^3$J=7.3 Hz, 3H, 6-CH$_2$CH$_3$), 3.42 (c, $^3$J=7.2 Hz, 2H, 6-CH$_2$CH$_3$), 3.44 (s, 3H, 4-NCH$_3$), 3.76 (s, 3H, 2-NCH$_3$), 6.15 (s, 1H, 9-H), 7.22 (d, $^3$J=8.4 Hz, 2H, 2' and 6'), 7.52 (d, $^3$J=8.4 Hz, 2H, 3' y 5'). $^{13}$C RMN (CDCl$_3$, 100 MHz): δ 12.53 (6-CH$_2$CH$_3$), 29.47 (4-NCH$_3$), 30.60 (2-NCH$_3$), 32.13 (6-CH$_2$CH$_3$), 105.83 (10b), 118.24 (d, 2C, $^2$J=22 Hz, 3' y 5'), 120.87 (6a ), 122.85 (1'), 128.29 (9), 138.29 (d, 2C, $^3$J=8 Hz, 2' y 6'), 147.6 (10a), 151.45 (3), 153.16 (1), 156.88 (8), 158.8 (4a), 164.63 (d, 1C, $^1$J=251 Hz, 4'), 171.21 (6), 181.9 (7), 181.68 (10).

Example 16

Obtaining 8-(4-chlorothiophenyl)-6-ethyl-2,4-dimethylpyrimido[4,5-c]isoquinoline-1,3,7,10(2H, 4H)-tetraone (16)

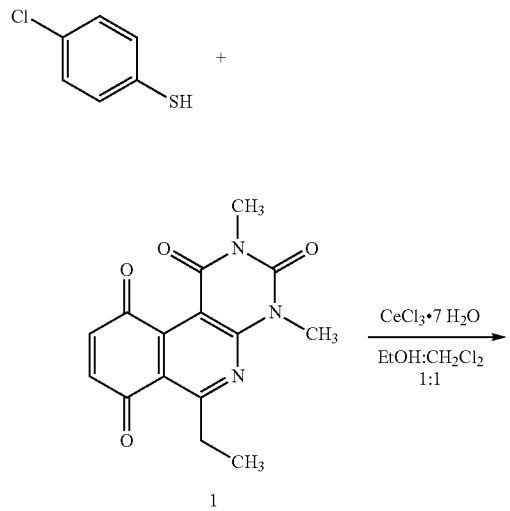

16

A solution of 6-ethyl-2,4-dimethylpyrimido[4,5-c]isoquinoline-1,3,7,10(2H,4H)-tetraone (1) (424.42 mg, 2.1 mmol), heptahydrated cerium(III) trichloride (0.5% mole of 1) in a mixture of CH2Cl2:MetOH=3.5:5 (8 ml), is added a solution of 4-Chloroethiophenol (98.80 mg, 1.0 mmol) dissolved in CH2Cl2:MetOH=3.5:5 (34 ml) by dripping from a side key burette at a rate of approximately 1 ml/30 min for approximately 14 hours. The reaction crude is purified with 60 g of silica gel (0.040-0.063 mm) using petroleum ether:dichloromethane:ethyl acetate=1.5:0.5:0.5:0.5 as the mobile phase. An orange-colored solid of 221.5 mg, 0.5 mmol is obtained, with a 75% yield.

Melting point 196.5-198.3° C. HRMS (M+): m/z calculated $C_{21}H_{16}ClN_3O_4S$ [M+]=441.05500; found=441.05491. IR (KBr): 1656.55, 1675.84 cm$^{-1°}$ C.=O (quinone); 1722.12 cm$^{-1°}$ C.=O (uracile). $^1$H RMN (CDCl$_3$, 400 MHz): δ 1.36 (t, $^3$J=7.3 Hz, 3H, 6-CH$_2$CH$_3$), 3.41 (c, $^3$J=7.2 Hz, 2H, 6-CH$_2$CH$_3$), 3.44 (s, 3H, 4-NCH$_3$), 3.76 (s, 3H, 2-NCH$_3$), 6.17 (s, 1H, 9-H), 7.49 (m, 4H, 2' 3' 5' and 6'-H). $^{13}$C RMN (CDCl$_3$, 100 MHz): δ 12.2 (6-CH$_2$CH$_3$), 29.2 (4-NCH$_3$), 30.3 (2-NCH$_3$), 31.9 (6-CH$_2$CH$_3$), 105.6 (10b), 120.6 (6a ), 125.8, 128.1 (9), 130.88, 137.09, 137.54, 147.3 (10a), 151.2 (3), 152.9 (1), 156.2 (8), 158.5 (4a), 170.9 (6), 180.7 (7), 181.3 (10).

Example 17

Obtaining 8-(4-bromothiophenyl)-6-ethyl-2,4-dimethylpyrimido[4,5-c]isoquinoline-1,3,7,10(2H,4H)-tetraone (17)

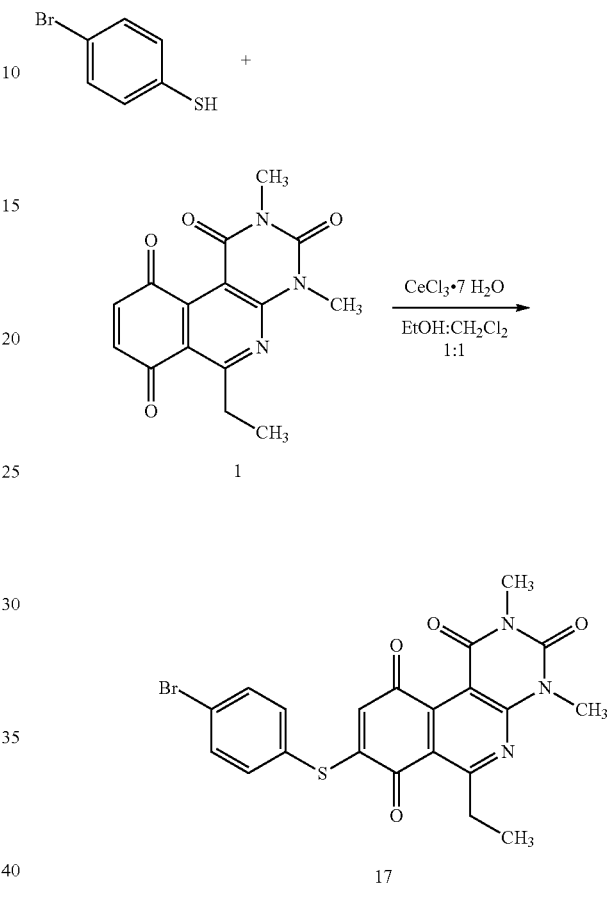

17

A 6-ethyl-2,4-dimethylpyrimido[4,5-c]isoquinoline 1,3,7,10(2H,4H)-tetraone (1) (424.42 mg, 2.1 mmol), heptahydrated cerium trichloride (0.5% mole of 1) in a mixture of CH2Cl2:MetOH=3.5:5 (8 ml), is added a solution of 4-bromothiophenol (98.80 mg, 1.0 mmol) dissolved in CH2Cl2:MetOH=3.5:5 (34 ml) by dripping from a side key burette at a rate of approximately 1 ml/30 min this for 14 hours. The reaction crude is purified with 75 g of silica gel (0.040-0.063 mm) using a 4.0:0.5:0.5 mobile phase of petroleum ether:dichloromethane:ethyl acetate. An orange-colored solid of 201.7 mg, 0.41 mmol is obtained, with a 68.1% yield.

Melting point 197.9-198.7° C. HRMS (M+): m/z calculated $C_{21}H_{16}BrN_3O_4S$ [M+]=485.00449; found=485.00438. IR (KBr): 1656.55, 1677.77 cm$^{-1°}$ C.=O (quinone); 1722.12 cm$^{-1°}$ C.=O (uracile). $^1$H RMN (CDCl$_3$, 400 MHz): δ 1.36 (t, $^3$J=7.3 Hz, 3H, 6-CH$_2$CH$_3$), 3.41 (c, $^3$J=7.2 Hz, 2H, 6-CH$_2$CH3), 3.44 (s, 3H, 4-NCH$_3$), 3.75 (s, 3H, 2-NCH$_3$), 6.18 (s, 1H, 9-H), 7.41 (d, $^3$J=8.4 Hz, 2H, 2' y 6'), 7.66 (d, $^3$J=8.4 Hz, 2H, 3' y 5'). $^{13}$C RMN (CDCl$_3$, 100 MHz): δ 12.2 (6-CH$_2$CH$_3$), 29.2 (4-NCH$_3$), 30.3 (2-NCH$_3$), 31.9 (6-CH$_2$CH$_3$), 105.5 (10b), 120.5 (6a ), 125.8 (4'), 126.4 (1'), 128.1 (9), 133.9 (2C, 3' y 5'), 137.3 (2C, 2' and 6'), 147.3 (10a), 151.2 (3), 152.9 (1), 156.0 (8), 158.5 (4a), 170.9 (6), 180.7 (7), 181.4 (10).

Example 18

Obtaining 6-ethyl-8-(4-hydroxythiophenyl)-2,4-dimethylpyrimido[4,5-c]isoquinoline-1,3,7,10(2H,4H)-tetraone (18)

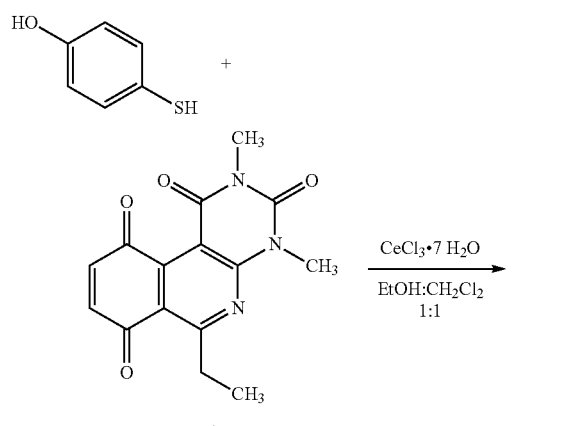

A solution of 6-ethyl-2,4-dimethylpyrimido[4,5-c]isoquinoline-1,3,7,10(2H,4H)-tetraone (1) (311.05 mg, 0.85 mmol), heptahydrated cerium(III) trichloride (0.5% mole of 1) in a mixture of CH2Cl2:EtOH=1:1 (10 ml), is added a solution of 4-hydroxythiophenol (52.80 mg, 0.41 mmol) dissolved in CH2Cl2:EtOH=1:1 (35 ml) by dripping from a side key burette at a rate of approximately 1 ml/30 min for 16 hours. The reaction crude is purified with 60 g of Silica gel (0.040-0.063 mm) using dichloromethane: ethyl acetate=9:0.8 as the mobile phase. An orange-colored solid of 127.2 mg, 0.3 mmol is obtained, with a 72% yield.

Example 19

Obtaining 6-ethyl-2,4-dimethyl-8-(4-nitrothiophenyl)pyrimido[4,5-c]isoquinoline-1,3,7,10(2H,4H)-tetraone (19)

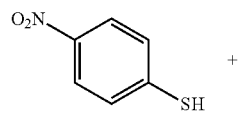

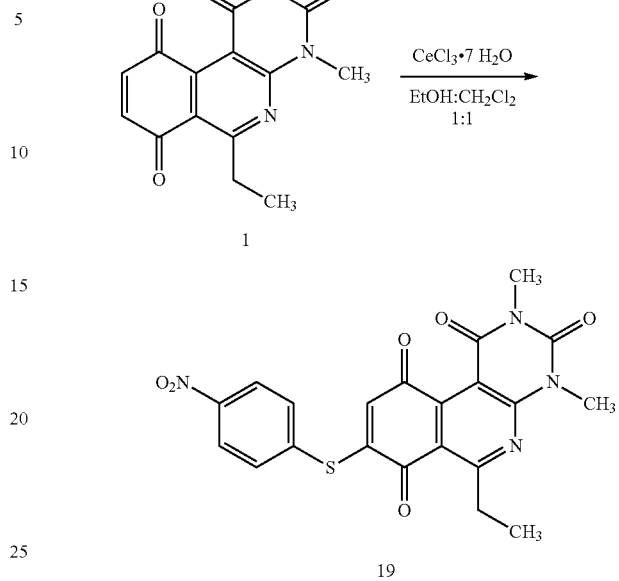

A solution of 6-ethyl-2,4-dimethylpyrimido[4,5-c]isoquinoline-1,3,7,10(2H,4H)-tetraone (1) (300.00 mg, 1.0 mmol), heptahydrated cerium(III) trichloride (0.5% mole of 1) in a mixture of CH2Cl2:EtOH=1:1 (10 ml), is added a solution of 4-nitrothiophenol (77.80 mg, 0.5 mmol) dissolved in CH2Cl2:EtOH=1:1 (35 ml) by dripping from a side key burette at a rate of approximately 1 ml/30 min for 16 hours. The reaction crude is purified with 60 g of Silica gel (0.040-0.063 mm) using dichloromethane:ethyl acetate:petroleum ether=15:1:3 as the mobile phase. An orange-colored solid of 220.5 mg, 0.49 mmol is obtained, with a 96% yield.

1H RMN (DMSOd6, 400 MHz): δ 1.36(t, 3J=7.3 Hz, 3H, 6-CH$_2$CH$_3$), 3.40(c, $^3$J=7.3 Hz, 2H, 6-CH$_2$CH3), 3.42 (s, 3H, 4-NCH$_3$), 3.75 (s, 3H, 2-NCH$_3$), 6.24 (s, 1H, 9-H), 7.76 (d, 2H, 2'-H y 6'-H), 8.34 (d, 2H1, 3'-H y 5'-H).

Example 20

Obtaining 8-(4-aminothiophenyl)-6-ethyl-2,4-dimethylpyrimido[4,5-c]isoquinoline-1,3,7,10(2H,4H)-tetraone (20)

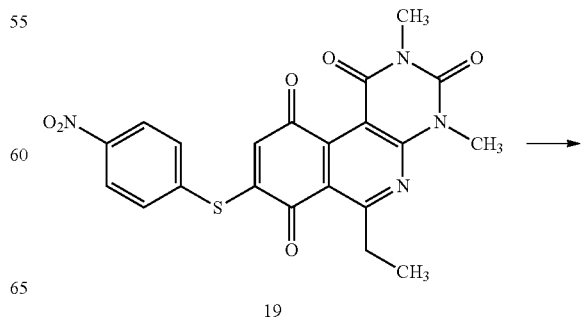

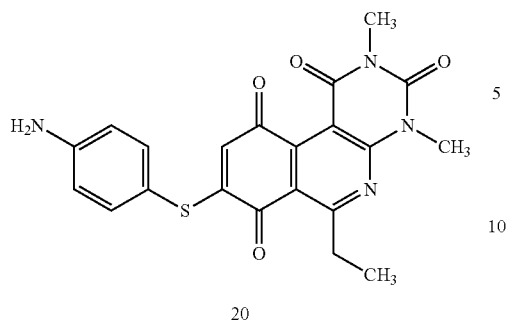

20

A solution of 6-ethyl-2,4-dimethyl-8-(4-nitrothiophenyl)pyrimido[4,5-c]isoquinoline-1,3,7,10(2H,4H)-tetraone 19 (100.00 mg, 0.33 mmol), is added to a solution of water:acetic acid:methanol=1:1:1 (30 mL) containing FeO (368 mg, 6.6 mmol) and agitated for 3 hours at 50° C. Then, 100 mL of water is added and neutralized with NaHCO3 and then extracted using dichloromethane (30 mL×3), after which the organic phase is dried with anhydrous NaSO4, filtered and vacuum dried. Finally, the reaction crude is purified with 60 g of silica. gel (0.040-0.063 mm) using dichloromethane:ethyl acetate:=9:1.5 as the mobile phase. A brown-colored solid of 30.5 mg, 0.07 mmol is obtained, with a 32.1% yield.

Example 21

Obtaining 8-(2,6-dimethoxythiophenyl)-6-ethyl-2,4-dimethylpyrimido[4,5-c]isoquinoline-1,3,7,10(2H,4H)-tetraone (21)

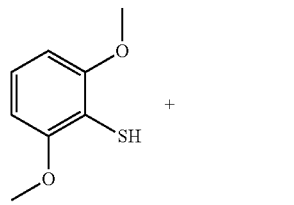

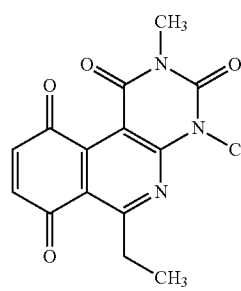

1

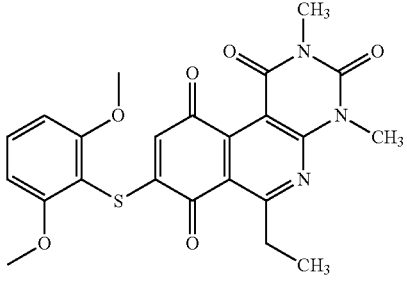

21

A solution of 6-ethyl-2,4-dimethylpyrimido[4,5-c]isoquinoline-1,3,7,10(2H,4H)-tetraone (1) (106.3 mg, 0.36 mmol), heptahydrated cerium(III) trichloride (0.5% mole of 1) in a mixture of CH2Cl2:EtOH=1:1 (10 ml), a solution of 2,6-dimethoxythiophenol (30.20 mg, 0.18 mmol) dissolved in CH2Cl2:EtOH=1:1 (35 ml) is added by dripping from a side key burette at a rate of approximately 1 ml/30 min for 16 hours. The reaction crude is purified with 60 g of Silica gel (0.040-0.063 mm) using dichloromethane:ethyl acetate:petroleum ether=9:1:3 as the mobile phase. A red-colored solid of 52.5 mg, 0.11 mmol is obtained, with a 63% yield.

Example 22

Obtaining 8-(5-bromine-2-methoxyphenylthio)-6-ethyl-2,4-dimethylpyrimido[4,5-c]isoquinoline-1,3,7,10(2H,4H)-tetraone (22)

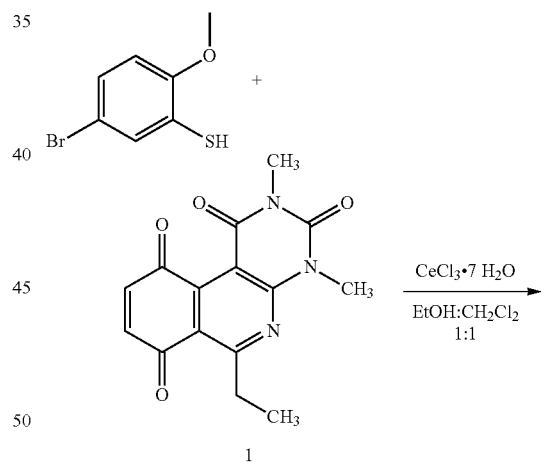

1

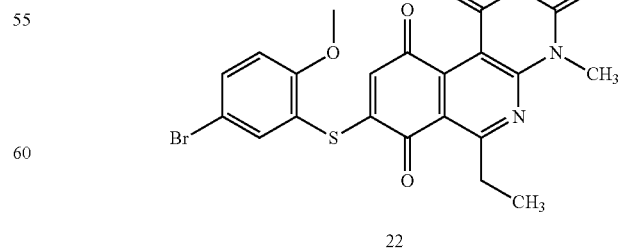

22

A solution of 6-ethyl-2,4-dimethylpyrimido[4,5-c]isoquinoline-1,3,7,10(2H,4H)-tetraone (1) (109.2 mg, 0.36 mmol), heptahydrated cerium(III) trichloride (0.5% mole of 1) in a mixture of CH2Cl2:EtOH=1:1 (10 ml), a solution of 5-bromine-2-methoxythiophenol (39.97 mg, 0.18 mmol) dissolved in CH2Cl2:EtOH=1:1 (35 ml) is added by dripping from a side key burette at a rate of approximately 1 ml/30 min for 16 hours. The reaction crude is purified with 60 g of Silica gel (0.040-0.063 mm) using dichloromethane:ethyl acetate:petroleum ether=20:1:4 as the mobile phase. An orange-colored solid of 71.8 mg, 0.14 mmol is obtained, with a 76% yield.

Example 23

Obtaining 8-(3,5-dichloroethiophenyl)-6-ethyl-2,4-dimethylpyrimido[4,5-c]isoquinoline-1,3,7,10(2H,4H)-tetraone (23)

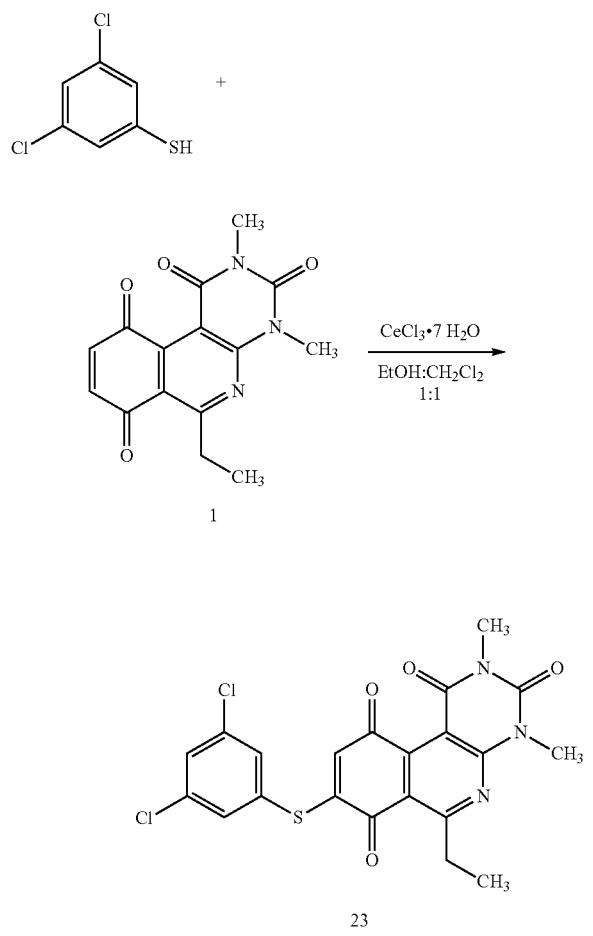

A solution of 6-ethyl-2,4-dimethylpyrimido[4,5-c]isoquinoline-1,3,7,10(2H,4H)-tetraone (1) (104.4 mg, 0.35 mmol), heptahydrated cerium (III) trichloride (0.5% mole of 1) in a mixture of CH2Cl2:EtOH-1:1 (10 ml), is added a solution of 3,5-dichlorothiophenol (31.6 mg, 0.18 mmol) dissolved in CH2Cl2:EtOH=1:1 (35 ml) by dripping from a side key burette at a rate of approximately 1 ml/30 min for 16 hours. The reaction crude is purified with 60 g of Silica gel (0.040-0.063 (mm) using dichloromethane:ethyl acetate:petroleum ether=20:1:7 as the mobile phase. A yellow-colored solid of 58.2 mg, 0.12 mmol is obtained, with a 69% yield.

Example 24

Obtaining 8-(benzylthio)-6-ethyl-2,4-dimethylpyrimido[4,5-o]isoquinoline-1,3,7,10(2H,4H)-tetraone (24)

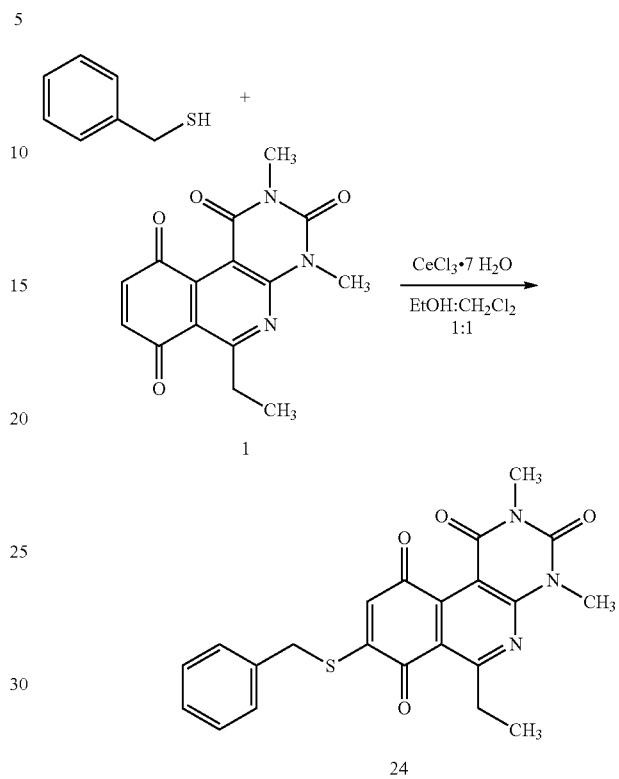

A solution of 6-ethyl-2,4-dimethylpyrimido[4,5-c]isoquinoline-1,3,7,10(2H,4H)-tetraone (1) (101.2 mg, 0.34 mmol), heptahydrated cerium(III) trichloride (0.5% mole of 1) in a mixture of CH2Cl2:EtOH=1:1 (10 ml), is added a solution of benzyl mercaptan (20.99 mg, 0.17 mmol) dissolved in CH2Cl2:EtOH=1:1 (35 ml) by dripping from a side key burette at a rate of approximately 1 ml/30 min for 16 hours. The reaction crude is purified with 60 g of Silica gel (0.040-0.063 mm) using dichloromethane:ethyl acetate:petroleum ether=9:1:3 as the mobile phase. A yellowish-orange solid of 47.3 mg, 0.11 mmol is obtained, with a 66% yield.

Example 25

Obtaining 8-(4-chlorobenzylthio)-6-ethyl-2,4-dimethylpyrimido[4,5-c]isoquinolin-1,3,7,10(2H,4H)-tetraone (25)

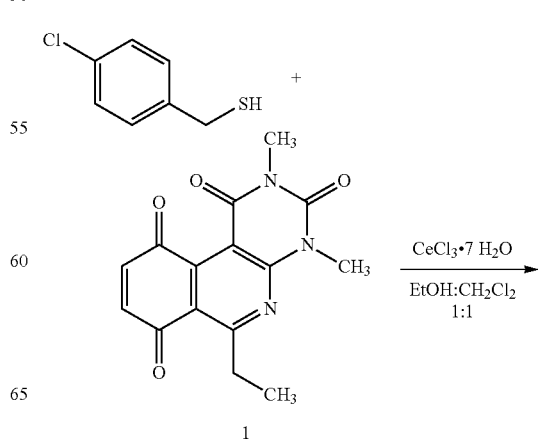

-continued

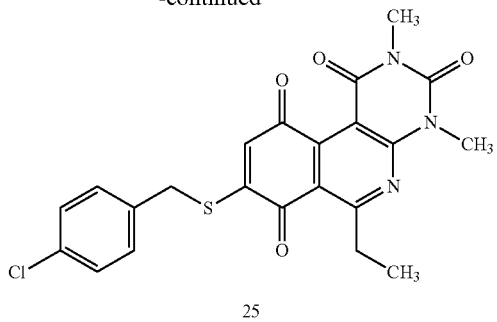

25

A solution of 6-ethyl-2,4-dimethylpyrimido[4,5-c]isoquinoline-1,3,7,10(2H,4H)-tetraone (1) (229.0 mg, 0.77 mmol), heptahydrated cerium(III) trichloride (0.5% mole of 1) in a mixture of CH2Cl2:EtOH=1:1 (10 ml), is added a solution of 4-nitrothiophenol (63.30 mg, 0.40 mmol) dissolved in CH2Cl2:EtOH=1:1 (35 ml) by dripping from a side key burette at a rate of approximately 1 ml/30 min for 16 hours. The reaction crude is purified with 60 g of Silica gel (0.040-0.063 mm) using dichloromethane:ethyl acetate:petroleum ether: 10:1:5 as the mobile phase. An orange-colored solid of 111.2 mg, 0.24 mmol is obtained, with a 32% yield.

Example 26

Obtaining 6-ethyl-2,4-dimethyl-8-(phenylethylthio)pyrimido[4,5-c]isoquinoline-1,3,7,10(2H,4H)-tetraone (26)

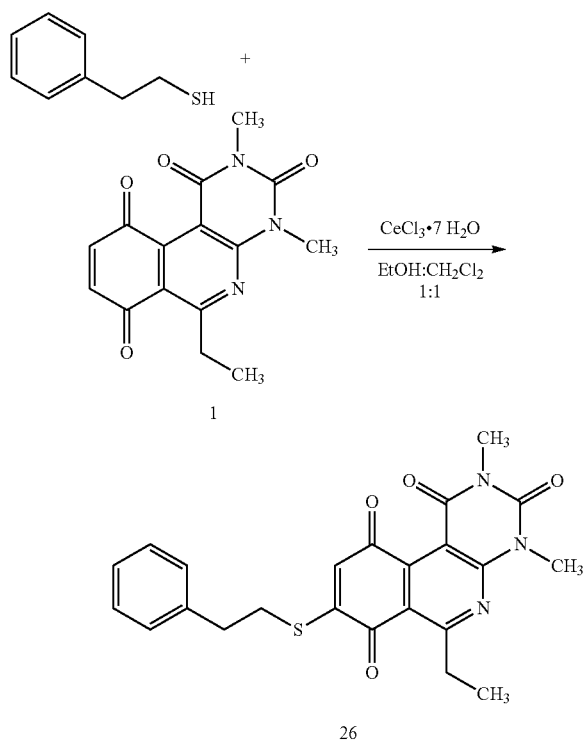

A solution of 6-ethyl-2,4-dimethylpyrimido[4,5-c]isoquinoline-1,3,7,10(2H,4H)-tetraone (1) (203.4 mg, 0.68 mmol), heptahydrated cerium(III) trichloride (0.5% mole of 1) in a mixture of CH2Cl2:EtOH=1:1 (10 ml), is added a solution of phenylethyl mercaptan (47.0 mg, 0.34 mmol) dissolved in CH2Cl2:EtOH=1:1 (35 ml) by dripping from a side key burette at a rate of approximately 1 ml/30 min for 16 hours. The reaction crude is purified with 60 g of Silica gel (0.040-0.063 mm) using dichloromethane:ethyl acetate:petroleum ether=10:1:6 as the mobile phase. A yellowish-orange solid of 117.2 mg, 0.27 mmol is obtained, with a 79% yield.

Example 27

Obtaining 8-(benzothiazole-2-ylthio)-6-ethyl-2,4-dimethylpyrimido[4,5-c]isoquinoline-1,3,7,10(2H,4H)-tetraone (27)

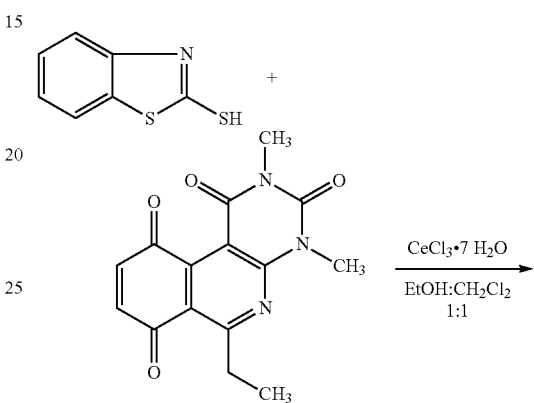

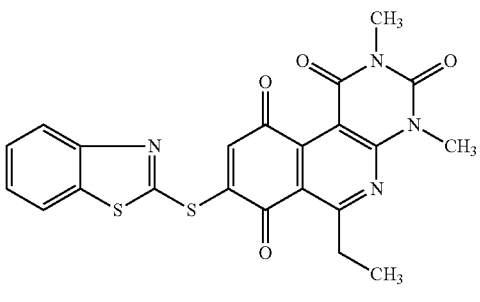

A solution of 6-ethyl-2,4-dimethylpyrimido[4,5-c]isoquinoline-1,3,7,10(2H,4H)-tetraone 1 (197.34 mg, 0.65 mmol), heptahydrated cerium(III) trichloride (0.5% mole of 1) in a mixture of CH2Cl2:EtOH=1:1 (10 ml), is added a solution of benzothiazole (61.6 mg, 0.37 mmol) dissolved in CH2Cl2:EtOH=1:1 (35 ml) by dripping from a side key burette at a rate of approximately 1 ml/30 min for 16 hours. The reaction crude is purified with 60 g of Silica gel (0.040-0.063 mm) using dichloromethane:ethyl acetate:petroleum ether=9:1:3 as the mobile phase. A yellow-colored solid of 121.2 mg, 0.26 mmol is obtained, with a 71% yield.

Example 28

Obtaining 8-(2-bromo-4-chlorothiophenyl)-6-ethyl-2,4-dimethylpyrimido[4,5-c]isoquinoline-1,3,7,10(2H,4H)-tetraone (28)

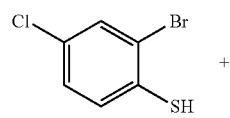

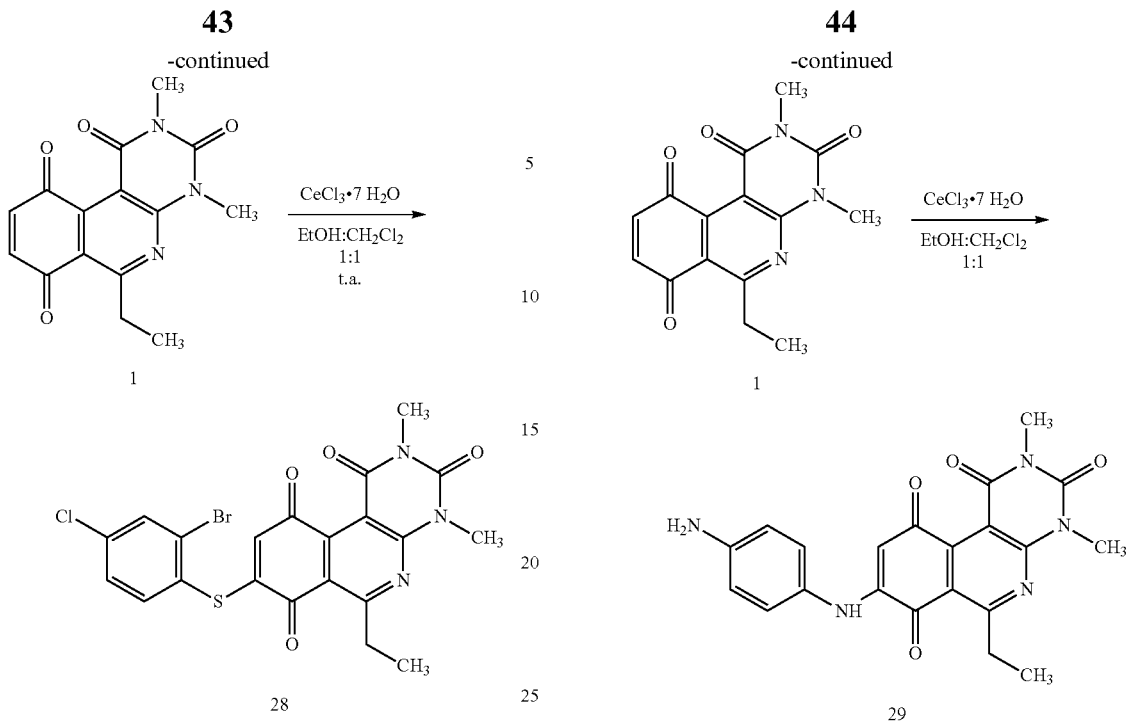

A solution of 6-ethyl-2,4-dimethylpyrimido[4,5-10c]isoquinoline-1,3,7,10(2H,4H)-tetraone 1 (431.2 mg, 1.96 mmol), heptahydrated cerium(III) trichloride (0.5% mole of 1) in a mixture of CH2Cl2:MetOH=1:1 (10 ml), is added a solution of 4-chloro-2-bromo-thiophenol (164.1 mg, 1.0 mmol) dissolved in CH2Cl2:MetOH=1:1 (30 ml) by dripping from a side key burette at a rate of approximately 1 ml/30 min for 16 hours. The reaction crude is purified with 140 g of silica gel (0.040-0.063 mm) using: ethyl acetate:dichloromethane:petroleum ether=1:4:5 as the mobile phase. An orange-colored solid of 324.7 mg, 0.6 mmol is obtained, with an 87% yield.

Melting point 198.4-200.2° C. Exact Measure=518.96552. $^1$H RMN (CDCl$_3$, 400 MHz): δ 1.38 (t, $^3$J=7.2 Hz, 3H, 6-CH$_2$CH$_3$); 3.42 (c, $^3$J=7.2 Hz, 2H, 6-CH$_2$CH$_3$); 3.45 (s, 3H, 4-NCH$_3$); 3.76 (s, 3H, 2-NCH$_3$); 6.07 (s, 1H, 9-H); 7.44 (dd, $^{3,4}$J=8.3, 1.9 Hz, 1H, 5'); 7.59 (d, $^3$J=8.3 Hz, 1H, 6'); 7.82 (d, $^4$J=1.9 Hz, 1H, 3'). $^{13}$C RMN (CDCl$_3$, 100 MHz): δ 12.10 (6-CH$_2$CH$_3$); 29.08 (4-NCH$_3$); 30.22 (2-NCH$_3$); 31.74 (6-CH$_2$CH$_3$); 105.52 (10a); 120.47 (6a); 127.35 (9); 127.96 (1'); 129.53 (5'); 131.28 (2'); 132.42 (4'); 138.18 (3'); 138.46 (6'); 147.10 (10b); 151.04 (3); 152.82 (1); 153.43 (8); 158.32 (4a); 170.85 (6); 180.50 (10); 180.99 (7).

Example 29

Obtaining 8-(4-amino-phenylamino)-6-ethyl-2,4-dimethylpyrimido[4,5-c]isoquinoline-1,3,7,10(2H,4H)-tetraone (29)

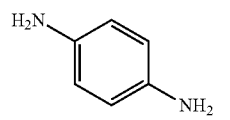

A solution of 6-ethyl-2,4-dimethylpyrimido[4,5-c]isoquinoline-1,3,7,10(2H,4H)-tetraone 1 (100.0 mg, 0.33 mmol), heptahydrated cerium(III) trichloride (0.5% mole of 1) in a mixture of CH2Cl2:EtOH=1:1 (20 ml), is added 1,4-phenylenediamine (72.2 mg, 0.66 mmol) and left to react for 16 hours. The reaction crude is purified with 60 g of silica gel (0.040-0.063 mm) using chloroform:ethyl acetate=8:1 as the mobile phase. A green solid of 69.1 mg, 0.17 mmol is obtained, with a 51% yield.

Example 30

Obtaining 6-ethyl-2,4-dimethyl-8-(phenylamino)pyrimido[4,5-c]isoquinoline-1,3,7,10(2H,4H)-tetraone (30)

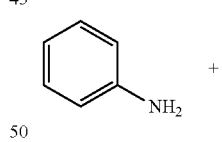

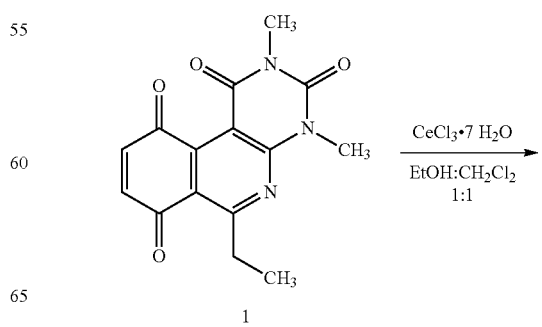

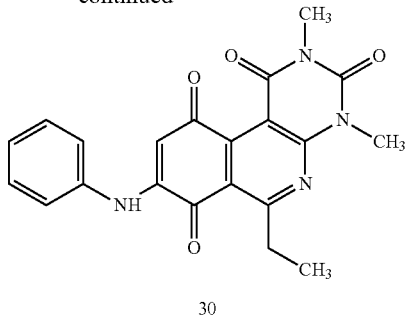

30

A solution of 6-ethyl-2,4-dimethylpyrimido[4,5-c]isoquinoline-1,3,7,10(2H,4H)-tetraone 1 (100.0 mg, 0.33 mmol), heptahydrated cerium(III) trichloride (0.5% mole of 1) in a mixture of CH2Cl2:EtOH=1:1 (20 ml), is added aniline (61.5 mg, 0.66 mmol) and allowed to react for 16 hours. The reaction crude is purified with 60 g of Silica gel (0.040-0.063 mm) using dichloromethane:ethyl acetate:petroleum ether=1:2:4 as the mobile phase. A purple-colored solid of 97.6 mg, 0.25 mmol is obtained, with a 76% yield.

Example 31

Obtaining 6-ethyl-8-((4-fluorophenyl)amino)-2,4-dimethylpyrimido[4,5-c]isoquinoline-1,3,7,10(2H,4H)-tetraone (31)

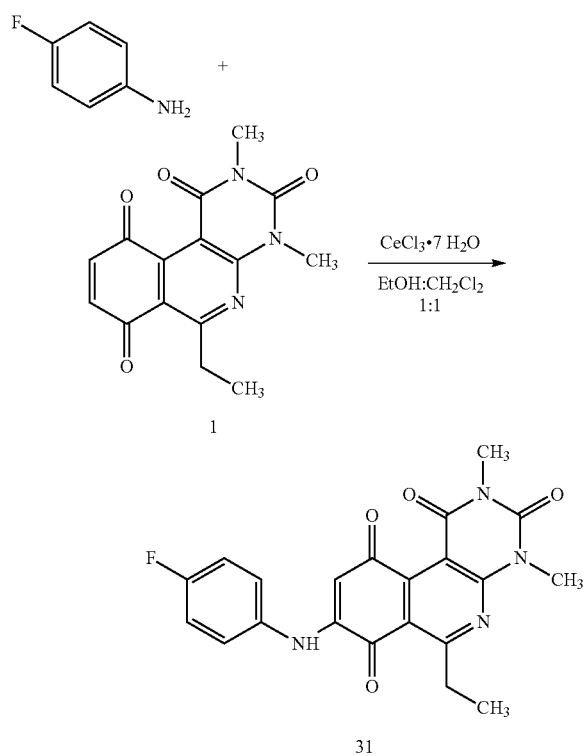

31

A solution of 6-ethyl-2,4-dimethylpyrimido[4,5-c]isoquinoline-1,3,7,10(2H,4H)-tetraone 1 (100.0 mg, 0.33 mmol), heptahydrated cerium(III) trichloride (0.5% mole of 1) in a mixture of CH2Cl2:EtOH=1:1 (20 ml), is added 4-fluoraniline (73.3 mg, 0.66 mmol) and left to react for 16 hours. The reaction crude is purified with 60 g of silica gel (0.040-0.063 mm) using chloroform:ethyl acetate:petroleum ether=10:3:3 as the mobile phase. A purple-colored solid of 94.3 mg, 0.23 mmol is obtained, with a 70% yield.

Example 32

Obtaining 8-((4-chlorophenyl)amino)-6-ethyl-2,4-dimethylpyrimido[4,5-c]isoquinoline-1,3,7,10(2H,4H)-tetraone (32)

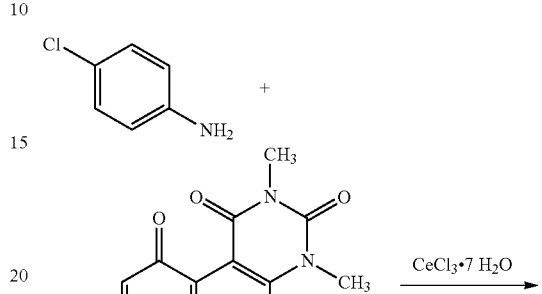

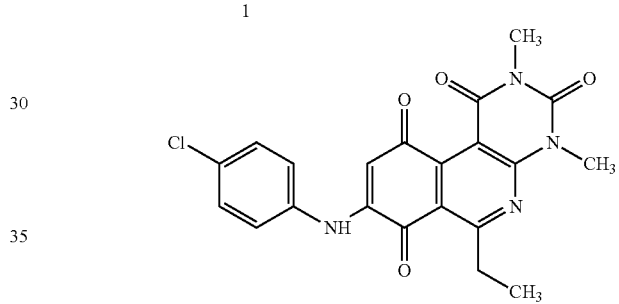

32

A solution of 6-ethyl-2,4-dimethylpyrimido[4,5-c]isoquinoline-1,3,7,10(2H,4H)-tetraone 1 (100.0 mg, 0.33 mmol), heptahydrated cerium(III) trichloride (0.5% mol of 1) in a mixture of CH2Cl2:EtOH=1:1 (20 ml), is added 4-chloroaniline (84.2 mg, 0.66 mmol) and left to react for 16 hours. The reaction crude is purified with 60 g of Silica gel (0.040-0.063 20 mm) using chloroform:ethyl acetate 2:1:2 as the mobile phase. A purple-colored solid of 72.2 mg, 0.17 mmol is obtained, with a 52% yield.

1H RMN (CDCl13, 400 MHz): δ 1.36 (t, 3J=7.3 Hz, 3H, 6-CH$_2$CH$_3$), 3.40(c, 3J=7.3 Hz, 2H, 6-CH$_2$CH$_3$), 3.47 (s, 3H, 4-NCH$_3$), 3.76 (s, 3H, 2-NCH$_3$), 6.40 (s, 1H, 9-H), 7.20 (d, 3J=8.8 Hz, 2H, 2'-H y 6'-H) 7.39 (d, 3J=8.8 Hz, 2H, 3'-H y 5'-H), 7.56 (1H, NH).

Example 33

Obtaining 8-(4-bromo-phenylamino)-6-ethyl-2,4-dimethylpyrimido[4,5-c]isoquinoline-1,3,7,10(2H,4H)-tetraone (33)

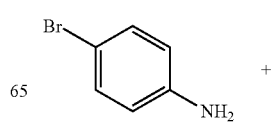

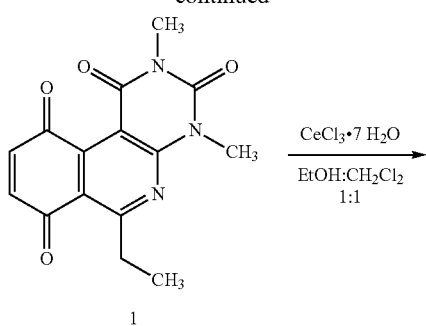

1

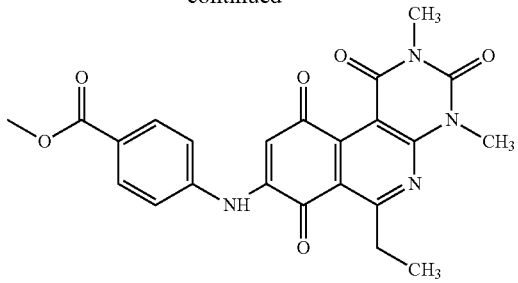

34

A solution of 6-ethyl-2,4-dimethylpyrimido[4,5-c]isoquinoline-1,3,7,10(2H,4H)-tetraone 1 (103.0 mg, 0.33 mmol), heptahydrated cerium(III) trichloride (0.5% mole of 1) in a mixture of CH2Cl2:EtOH=1:1 (20 ml), is added 4-methylsteraniline (97.7 mg, 0.66 mmol) and allowed to react for 16 hours. The reaction crude is purified with 60 g of silica gel (0.040-0.063 mm) using chloroform:ethyl acetate=20:1 as the mobile phase. A red-colored solid of 55.8 mg, 0.12 mmol is obtained, with a 36% yield.

Example 35

Obtaining 8,9-bis(thiophenyl)-6-ethyl-2,4-dimethylpyrimido[4,5-c]isoquinoline-1,3,7,10(2H,4H)-tetraone (35)

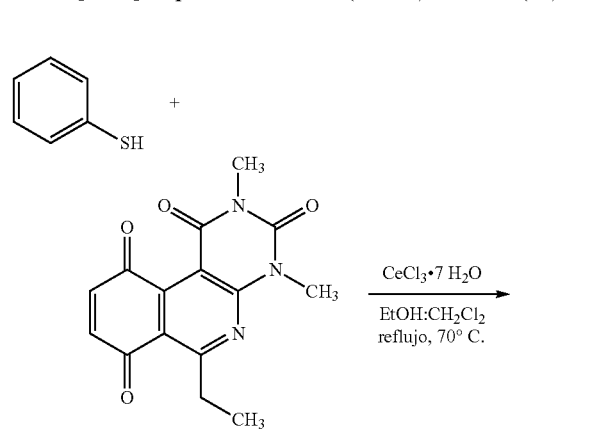

33

A solution of 6-ethyl-2,4-dimethylpyrimido[4,5-c]isoquinoline-1,3,7,10(2H,4H)-tetraone 1 (100.0 mg, 0.33 mmol), heptahydrated cerium(III) trichloride (0.5% mole of 1) in a mixture of CH2Cl2:EtOH=1:1 (20 ml), is added 4-bromoaniline (113.5 mg, 0.66 mmol) and left to react for 16 hours. The reaction crude is purified with 60 g of Silica gel (0.040-0.063 mm) using dichloromethane:ethyl acetate:petroleum ether=4:1:4 as the mobile phase. A purple-colored solid of 103.2 mg, 0.22 mmol is obtained, with a 67% yield.

Example 34

Obtaining 8-(4-methylester-phenylamino)-6-ethyl-2,4-dimethylpyrimido[4,5-c]isoquinoline-1,3,7,10(2H,4H)-tetraone (34)

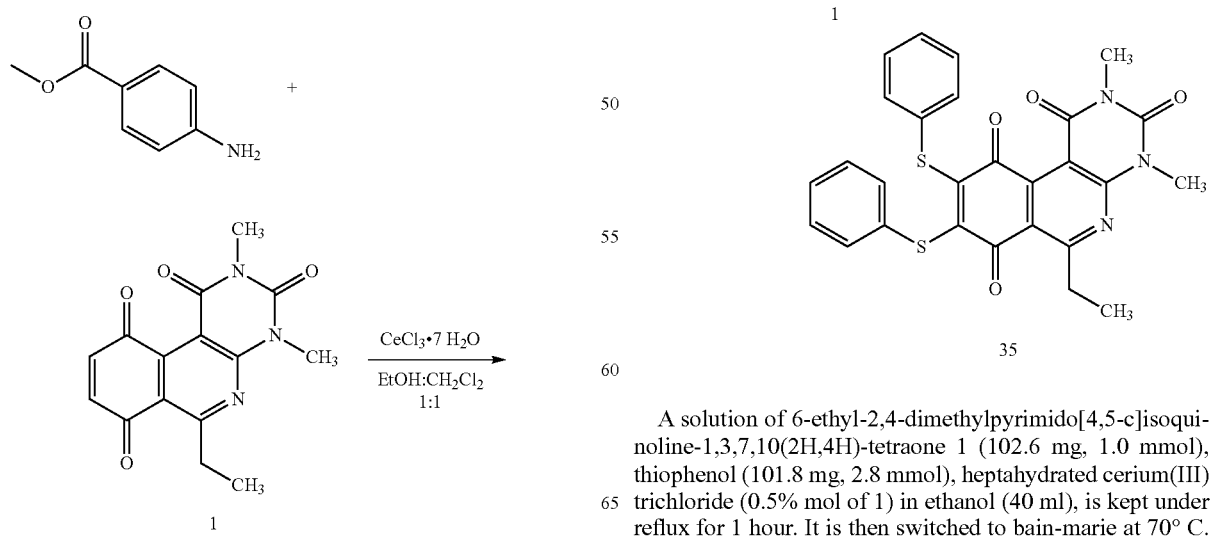

35

A solution of 6-ethyl-2,4-dimethylpyrimido[4,5-c]isoquinoline-1,3,7,10(2H,4H)-tetraone 1 (102.6 mg, 1.0 mmol), thiophenol (101.8 mg, 2.8 mmol), heptahydrated cerium(III) trichloride (0.5% mol of 1) in ethanol (40 ml), is kept under reflux for 1 hour. It is then switched to bain-marie at 70° C. for 2 hours. It is then kept agitated at room temperature for 18 h. The reaction crude is purified with 70 g of silica gel (0.040-0.063 mm) using ethyl acetate:dichloromethane:petroleum ether=1.0:4.0:5.0 as the mobile phase. A red-colored solid of 68.1 mg (0.13 mmol) is obtained, with a 39% yield.

Melting Point 188.9-191.5° C. Exact mass=515.09735. $^1$H RMN (CDCl$_3$, 400 MHz): δ 1.13 (t, $^3$J=7.3 Hz, 3H, 6-CH$_2$CH$_3$); 3.06 (c, $^3$J=7.3 Hz, 2H, 6-CH$_2$CH$_3$); 3.31 (s, 3H, 4-NCH$_3$); 3.71 (s, 3H, 2-NCH$_3$); 7.30 (m, 3H, 8,9-SC$_6$H$_5$); 7.41 (m, 5H, 8,9-SC$_6$H$_5$); 7.56 (dd, $^3$J=6.7 Hz, 2H, 2", 6"). $^{13}$C RMN (CDCl$_3$, 100 MHz): δ 12.33 (6-CH$_2$CH$_3$); 28.76 (4-NCH$_3$); 30.06 (2-NCH$_3$); 31.01 (6-CH$_2$CH$_3$); 104.80 (10b-C); 122.12 (6a-C); 127.93 (9-C); 128.93; 129.27; 129.42; 130.19; 131.23; 133.16; 133.30; 143.68; 147.74 (10a-C); 150.50 (3-C); 151.09 (1-C); 152.07 (8-C); 157.63 (4a-C); 169.91 (6-C); 176.79 (7-C); 179.33 (10-C).

Example 36

Obtaining 8,9-bis(4-chlorothiophenyl)-6-ethyl-2,4-dimethylpyrimido[4,5-c]isoquinoline-1,3,7,10(2H,4H)-tetraone (36)

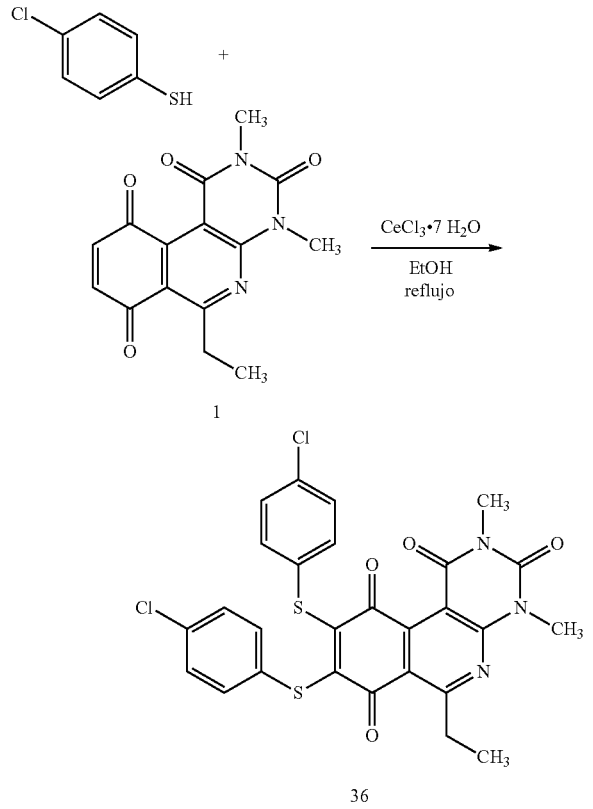

A solution of 6-ethyl-2,4-dimethylpyrimido[4,5-c]isoquinoline-1,3,7,10(2H,4H)-tetraone 1 (131.4 mg, 1.0 mmol), 4-chlorothiophenol (162.9 mg, 2.5 mmol) heptahydrated cerium(III) trichloride (0.5% mole of 1) in ethanol (40 ml), was kept under reflux for 3 hours at 70° C. It is then kept in agitation at room temperature for 18 hours. The reaction crude oil is purified with 70 g of silica gel (0.040-0.063 mm) using ethyl acetate:dichloromethane:ether of oil=2.0:2.0:6.0 as the mobile phase. A brown-colored solid of 64.2 mg, 0.11 mmol is obtained, with a 49% yield.

Melting Point 207.8-209.8° C. Exact Mass=583.01940. $^1$H RMN (CDCl$_3$, 400 MHz): δ 1.17 (t, $^3$J=7.3 Hz, 3H, 6-CH$_2$CH$_3$); 3.10(c, $^3$J=7.3 Hz, 2H, 6-CH$_2$CH$_3$); 3.33 (s, 3H, 4-NCH$_3$); 3.71 (s, 3H, 2-NCH$_3$); 7.29 (d, $^3$J=8.8 Hz, 2H, 2", 6"); 7.36 (d, $^3$J=8.7 Hz, 2H, 2',6'); 7.36 (d, $^3$J=8.7 Hz, 2H, 3', 5'); 7.49 (d, $^3$J=8.7 Hz, 2H, 3", 5"). $^{13}$C RMN (CDCl$_3$, 100 MHz): δ 12.31 (6-CH$_2$CH$_3$); 28.76 (4-NCH$_3$); 30.09 (2-NCH$_3$); 31.16 (6-CH$_2$CH$_3$); 104.76 (10b-C); 121.75 (6a-C); 128.18 (9-C); 129.48; 129.69; 131.43; 132.63; 134.35; 134.76; 135.72; 142.32; 147.77 (10a-C); 151.01 (3-C); 151.24 (1-C); 152.14 (8-C); 157.61 (4a-C); 170.15 (6-C); 176.40 (7-C); 179.45 (10-C).

Example 37

Obtaining 8-(2-bromo-4-chloro-thiophenyl)-6-ethyl-7,10-dihydroxy-2,4-dimethylpyrimido[4,5-c]isoquinolinee-1,3 (2H,4H)-dione. (37)

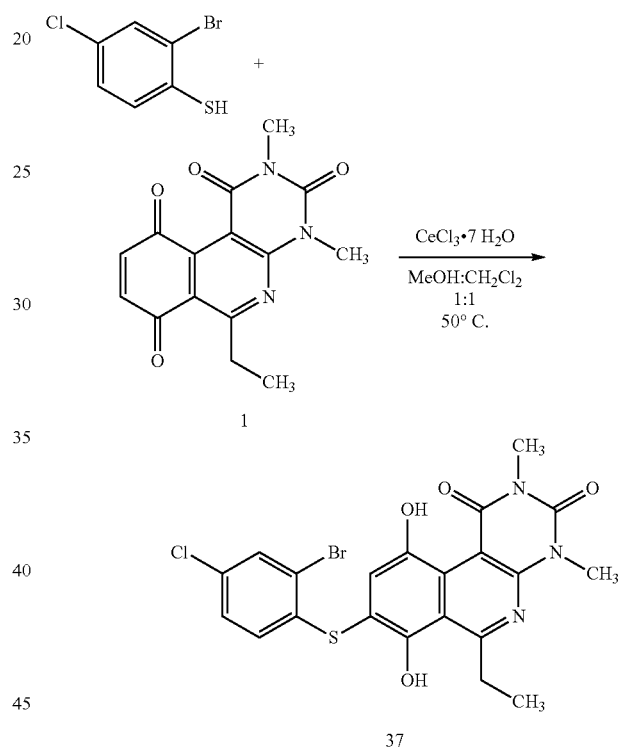

A solution of 6-ethyl-2,4-dimethylpyrimido[4,5-c]isoquinoline-1,3,7,10(2H,4H)-tetraone 1 (108.1 mg, 1.0 mmol), 4-chloro-2-bromo-thiophenol (159.1 mg, 1.97 mmol) cerium(III) trichloride heptahydrate (0.5% mol of 1) in CH2Cl2:MeOH=1:1 (40 mL), is warmed to 50° C. for 2 hours. It is then kept in agitation at room temperature for 18 h. The reaction crude is purified with 140 g of silica gel (0.040-0.063 mm) using ethyl acetate:dichloromethane:petroleum ether=1:10:9 as the mobile phase. A yellow solid of 70.3 mg (0.1 mmol) is obtained, with a 26% yield.

Melting Point 223.1-224.2° C. Exact Mass=520,98117. $^1$H RMN (CDCl$_3$, 400 MHz): δ 1.40 (t, $^3$J=7.2 Hz, 3H, 6-CH$_2$CH$_3$); 3.61 (s, 3H, 4-NCH$_3$); 3.62 (c, $^3$J=7.2 Hz, 2H, 6-CH$_2$CH$_3$); 3.89 (s, 3H, 2-NCH$_3$); 6.62 (d, $^3$J=8.5 Hz, 1H, 6'); 7.09 (dd, $^{3,4}$J=8.5H<, 2.1 Hz, 1H, 5'); 7.28 (s, 1H, 9-H); 7.48 (s, 1H, 7-OH); 7.59 (d, 3J=2.1, 1H, 3'); 11.87 (s, 1H, 10-OH). $^{13}$C RMN (CDCl$_3$, 100 MHz): δ 12.74 (6-CH$_2$CH$_3$); 29.92 (4-NCH$_3$); 30.88 (2-NCH$_3$); 34.96 (6-CH$_2$CH$_3$); 98.96 (10a); 113.01 (6a ); 116.09 (9); 122.00;

127.46; 128.30; 128.33; 128.47; 132.78; 132.86 (10b); 138.84 (3); 147.65 (1); 149.90 (8); 150.35 (4a); 150.52 (6); 165.27 (10); 173.35 (7).

Example 38

Production of 8-thiopropyl-6-ethyl-2,4-dimethyl-2,4-dimethylpyrimido[4,5-c]isoquinoline-1,3,7,10(2H,4H)-tetraone (38).

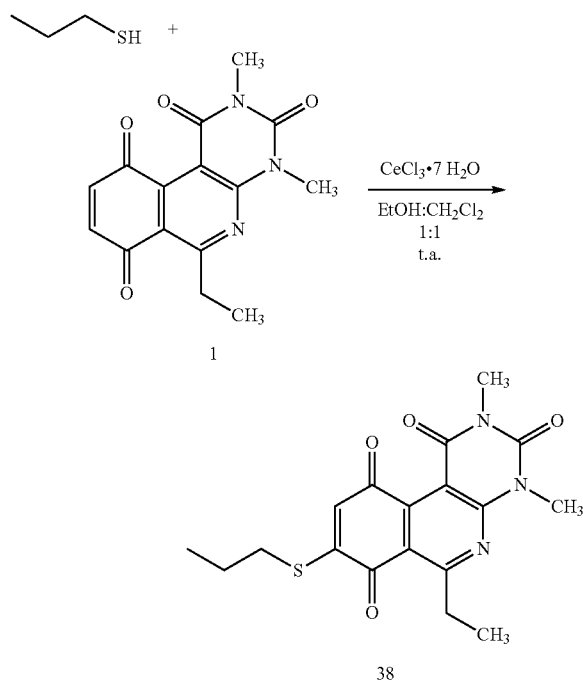

A solution of 6-ethyl-2,4-dimethylpyrimido[4,5-c]isoquinoline-1,3,7,10(2H,4H)-tetraone 1 (103.8 mg, 1.0 mmol), propanethiol (76.2 mg, 2.4 mmol), heptahydrated cerium (III) trichloride (0.5% mole of 1), is kept in agitation at room temperature for 16 hours. The reaction crude is purified with 60 g of silica gel (0.040-0.063 mm) using ethyl acetate: dichloromethane:petroleum ether=1:2:7 as the mobile phase. An orange-colored solid of 30.5 mg, 0.08 mmol is obtained, with a 24% yield.

Melting Point 163.8-164.9° C. Exact Mass=373,10963. $^1$H RMN (CDCl$_3$, 400 MHz): δ 1.11 (t, $^3$J=7.3 Hz, 3H, 8-CH$_2$CH$_2$CH$_3$); 1.35 (t, 3J=7.3 Hz, 3H, 6-CH2CH3); 1.82 (h, 2H, 8-CH2CH2); 2.81 (t, 3J=7.3 Hz, 3H, 8-CH2-CH2CH3); 3.39 (c, 3J=7.3 Hz, 2H, 6-CH2CH3); 3.48 (s, 3H, 4-NCH$_3$); 3.76 1H, 9-H). (s, 3H, 2-NCH3); 6.69 (s $^{13}$C RMN (CDCl$_3$, 100 MHz): δ 12.14 (6-CH$_2$CH$_3$); 13.66 (8-CH2CH2CH3); 20.89 (8-CH2CH2CH3); 29.08 (4-NCH$_3$); 30.17 (2-NCH$_3$); 31,72(6-CH$_2$CH$_3$); 32.76 (8-CH$_2$CH$_2$CH$_3$); 105.42 (10a); 120.84 (6a ); 126.46 (9); 147.15 (10b); 151.14 (3); 152.69 (1); 155.40 (8); 158.55 (4a); 170.74 (6); 180.79 (10); 180.79 (7).

Example 39

Obtaining 8,9-bis-thiopropyl-6-ethyl-2,4-dimethylpyrimido[4,5-c]isoquinoline-1,3,7,10(2H,4H)-tetraone (39)

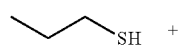

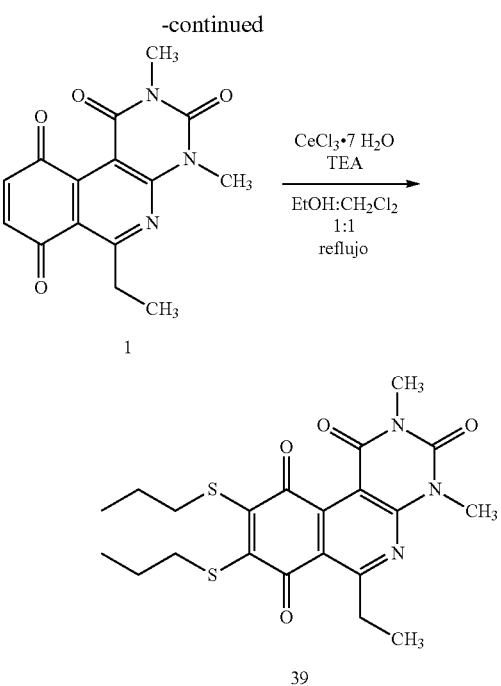

A solution of 6-ethyl-2,4-dimethylpyrimido[4,5-c]isoquinoline-1,3,7,10(2H,4H)-tetraone 1 (120.5 mg, 1.0 mmol), propanethiol (73.5 mg, 2.4 stool), heptahydrated cerium(III) trichloride (0.5% mol of 1), 72 mg trimethylamine (68% mol of propanethiol) dissolved in EtOH: CH2Cl2=1:1 (40 ml), is kept in reflux for 4 hours. The reaction crude is purified with 70 g of silica gel (0.040-0.063 mm) using ethyl acetate: dichloromethane:petroleum ether=0.5:2.5:7 as the mobile phase. A red-colored solid of 155.5 mg, 0.35 mmol is obtained, with 86% yield.

Melting point 138.9-140.2° C. Exact mass=447,12865. $^1$H RMN (CDCl$_3$, 400 MHz): δ 1.11 (t, $^3$J=7.3 Hz, 3H, 8-CH$_2$CH$_2$CH$_3$); 1.35 (t, $^3$J=7.3 Hz, 3H, 6-CH$_2$CH$_3$); 1.82 (h, 2H, 8-CH$_2$CH$_2$CH$_3$); 2.81 (t, $^3$J=7.3 Hz, 3H, 8-CH$_2$CH$_2$CH$_3$); 3.39 (c, $^3$J=7.3 Hz, 2H, 6-CH$_2$CH$_3$); 3.48 (s, 3H, 4-NCH$_3$); 3.76 (s, 3H, 2-NCH$_3$); 6.69 (s, 1H, 9-H). $^{13}$C RMN (CDCl$_3$, 100 MHz): δ 12.14 (6-CH$_2$CH$_3$); 13.66 (8-CH$_2$CH$_2$CH$_3$); 20.89 (8-CH$_2$CH$_2$CH$_3$); 29.08 (4-NCH$_3$); 30.17 (2-NCH$_3$); 31.72 (6-CH$_2$CH$_3$); 32.76 (8-CH$_2$CH$_2$CH$_3$); 105.42 (10a); 120.84 (6a ); 126.46 (9); 147.15 (10b); 151.14 (3); 152.69 (1); 155.40 (8); 158.55 (4a); 170.4 (6); 180.79 (10); 180.79 (7).

Where the compound described in example 1 is an intermediary compound, as well as the synthesis of intermediary G compounds including the following stages:

a) reacting with the following compounds:

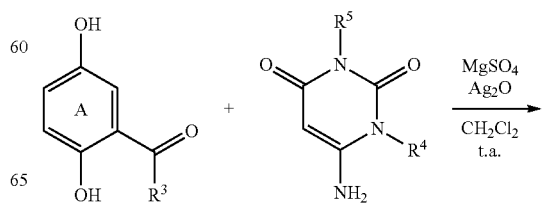

-continued

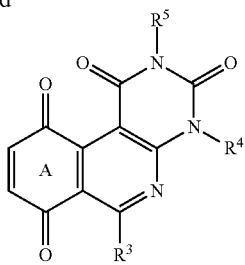

Compuesto intermediario G
Intermediary G compound where $R^3$ is —H, $C_1$-$C_{15}$ alkyl, —$NH_2$, —OH, —SH, —NH—$R^6$, —N—$^3(R^6)_2$, —O—$R^6$, —S—$R^6$; where $R^4$ y $R^5$ son H, un alkyl group $C_1$-$C_{15}$; where $R^6$ is a $C_1$-$C_{15}$ alkyl group, a substituted $C_1$-$C_{15}$ alkyl group, phenyl, substituted phenyl, aryl, substituted aryl, heterocycle, substituted heterocycle, heteroaryl, hetero-substituted aryl, where the substitutions of the $C_1$-$C_{15}$, aryl, phenyl, heterocycle and heteroaryl groups are: —CO—Z—$C_1$-$C_{15}$ alkyl, —Z—CO—$C_1$-$C_{15}$ alkyl, —H, -tert-butyl, -iso-propyl, —$C_1$-$C_{15}$ alkyl, —$CF_3$, halogen of the Cl, Br, F and I group, —$NH_2$, —$NO_2$, —NH—$R^7$, —N($R^7)_2$, —COOH, —COO—$R^7$—OCO—$R^7$, —O—$R^7$, —CN, —S—$R^7$, —S—$CF_3$ and substituted phenyl with —H, —$C_1$-$C_1$ alkyl, halogen of the Cl, Br, F and I group, —$NH_2$, —$NO_2$, —NH—$R^7$, —N($R^7)_2$, —COOH, —COO—$R^7$—OCO—$R^7$, —O—$R^7$, —CN, —S—$R^7$, —S—CF; where $R^7$ is an —H, $C_1$-$C_{15}$ alkyl, —OH group; where heterocycle is defined as a monocyclic ring, containing approximately 3 to 7 atoms in the ring, with 1 to 5 heteroatoms selected from N, O, and S, in the ring; where heteroaryl is defined as a cyclic or polycyclic aromatic ring system of 3 to 7 atoms in the ring, which has between 1 to 4 heteroatoms selected between N, O, and S; where aryl means a cyclic or polycyclic aromatic ring with 5 to 12 carbon atoms; to obtain the intermediary G compound.

The compounds obtained in Examples 1 through 39 are shown in Table I below as represented by the following structural formulae:

| No | Structure | IUPAC Name |
|----|-----------|------------|
| 1 | 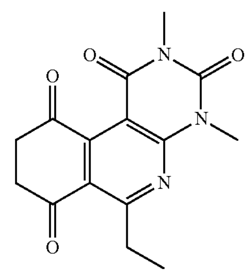 [SMILES: CCc1nc2c(c3c1C(=O)CCC3=O)c(=O)n(C)c(=O)n2C] | 6-Ethyl-2,4-dimethylpyrimido[4,5-c]isoquinoline-1,3,7,10(2H,4H)-tetraone |
| 2 | 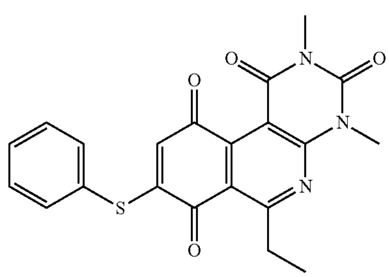 [SMILES: CCc1nc2c(c3c1C(=O)C(Sc1ccccc1)=CC3=O)c(=O)n(C)c(=O)n2C] | 6-Ethyl-2,4-dimethyl-8-(phenythio)pyrimido[4,5-c]isoquinoline-1,3,7,10(2H,4H)-tetraone |
| 3 | 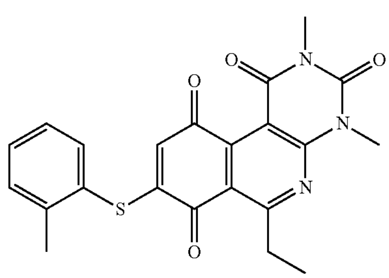 [SMILES: CCc1nc2c(c3c1C(=O)C(Sc1ccccc1C)=CC3=O)c(=O)n(C)c(=O)n2C] | 6-Ethyl-2,4-dimethyl-8-(o-tolylthio)pyrimido[4,5-c]isoquinoline-1,3,7,10(2H,4H)-tetraone |

-continued

| No | Structure | IUPAC Name |
|---|---|---|
| 4 | 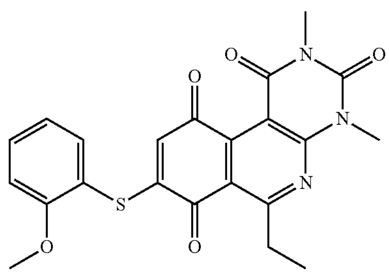 [SMILES: CCc1nc2c(c3c1C(=O)C(Sc1ccccc1OC)=CC3=O)c(=O)n(C)c(=O)n2C] | 6-Ethyl-8-((2-methoxyphenyl)thio)-2,4-dimethylpyrimido[4,5-c]isoquinoline-1,3,7,10(2H,4H)-tetraone |
| 5 | 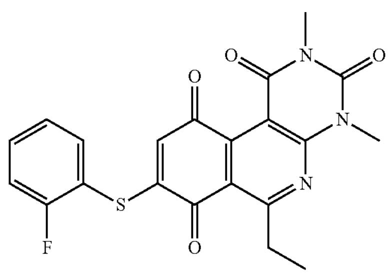 | 6-Ethyl-8-((2-fluorophenyl)thio)-2,4-dimethylpyrimido[4,5-c]isoquinoline-1,3,7,10(2H,4H)-tetraone |
| 6 | 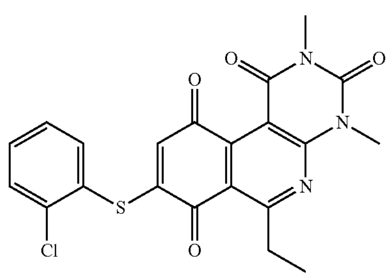 | 8-((2-chlorophenyl)thio)-6-ethyl-2,4-dimethylpyrimido[4,5-c]isoquinoline-1,3,7,10(2H,4H)-tetraone |
| 7 | 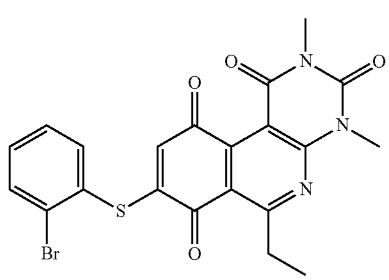 [SMILES: CCc1nc2c(c3c1C(=O)C(Sc1ccccc1Br)=CC3=O)c(=O)n(C)c(=O)n2C] | 8-((2-bromophenyl)thio)-6-ethyl-2,4-dimethylpyrimido[4,5-c]isoquinoline-1,3,7,10(2H,4H)-tetraone |
| 8 | 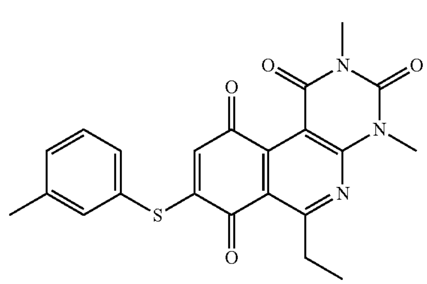 | 6-Ethyl-2,4-dimethyl-8-(m-tolylthio)pyrimido[4,5-c]isoquinoline-1,3,7,10(2H,4H)-tetraone |

-continued

| No | Structure | IUPAC Name |
|---|---|---|
| 9 | 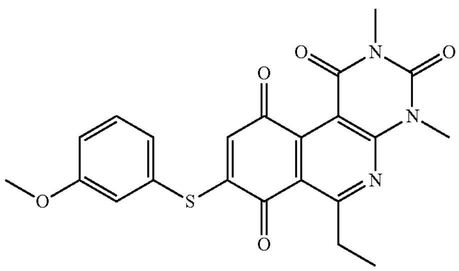 | 6-Ethyl-8-((3-methoxyphenyl)thio)-2,4-dimethylpyrimido[4,5-c]isoquinoline-1,3,7,10(2H,4H)-tetraone |
| 10 | 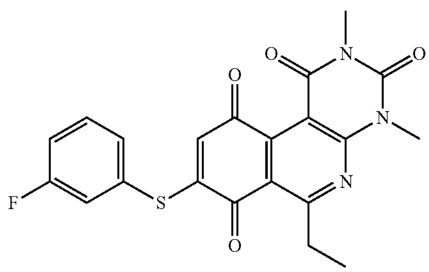 [SMILES: CCc1nc2c(c3c1C(=O)C(Sc1cccc(F)c1)=CC3=O)c(=O)n(C)c(=O)n2C] | 6-Ethyl-8-((3-fluorophenyl)thio)-2,4-dimethylpyrimido[4,5-c]isoquinoline-1,3,7,10(2H,4H)-tetraone |
| 11 | 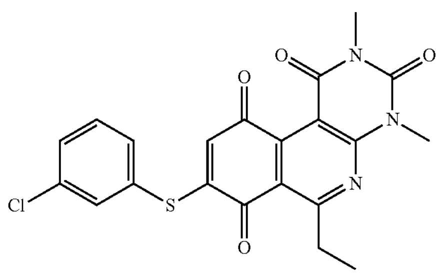 | 8-((3-chlorophenyl)thio)-6-ethyl-2,4-dimethylpyrimido[4,5-c]isoquinoline-1,3,7,10(2H,4H)-tetraone |
| 12 | 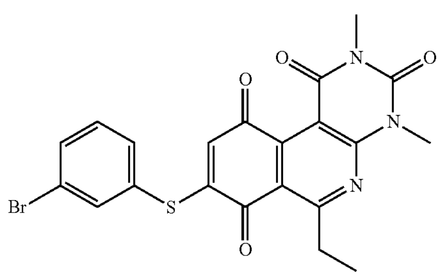 [SMILES: CCc1nc2c(c3c1C(=O)C(Sc1cccc(Cl)c1)=CC3=O)c(=O)n(C)c(=O)n2C] | 8-((3-bromophenyl)thio)-6-ethyl-2,4-dimethylpyrimido[4,5-c]isoquinoline-1,3,7,10(2H,4H)-tetraone |
| 13 | 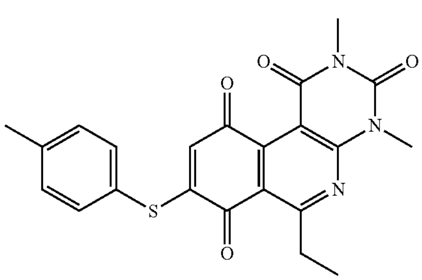 | 6-Ethyl-2,4-dimethyl-8-(p-tolylthio)pyrimido[4,5-c]isoquinoline-1,3,7,10(2H,4H)-tetraone |

-continued

| No | Structure | IUPAC Name |
|----|-----------|------------|
| 14 | 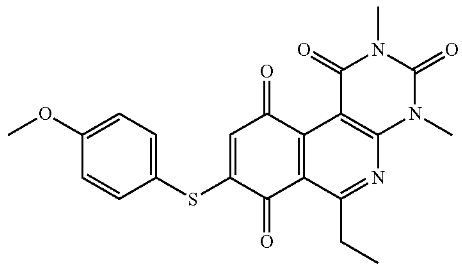 | 6-Ethyl-8-((4-methoxyphenyl)thio)-2,4-dimethylpyrimido[4,5-c]isoquinoline-1,3,7,10(2H,4H)-tetraone |
| 15 | 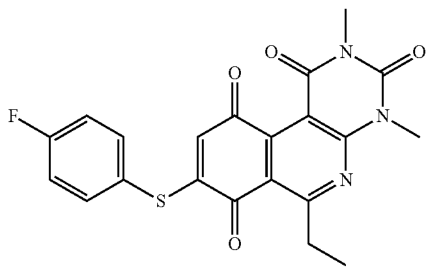 [SMILES: CCc1nc2c(c3c1C(=O)C(Sc1ccc(F)cc1)=CC3=O)c(=O)n(C)c(=O)n2C] | 6-Ethyl-8-((4-fluorophenyl)thio)-2,4-dimethylpyrimido[4,5-c]isoquinoline-1,3,7,10(2H,4H)-tetraone |
| 16 | 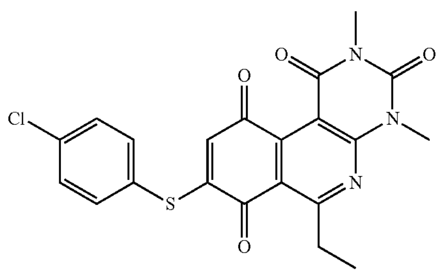 | 8-((4-chlorophenyl)thio)-6-ethyl-2,4-dimethylpyrimido[4,5-c]isoquinoline-1,3,7,10(2H,4H)-tetraone |
| 17 | 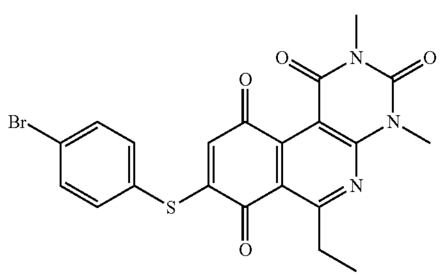 [SMILES: CCc1nc2c(c3c1C(=O)C(Sc1ccc(Cl)cc1)=CC3=O)c(=O)n(C)c(=O)n2C] | 8-((4-bromophenyl)thio)-6-ethyl-2,4-dimethylpyrimido[4,5-c]isoquinoline-1,3,7,10(2H,4H)-tetraone |
| 18 | 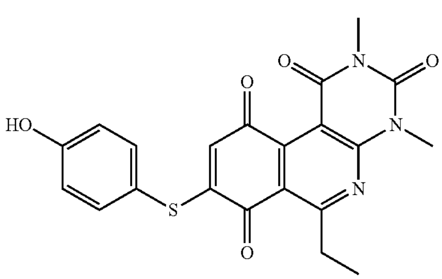 [SMILES: CCc1nc2c(c3c1C(=O)C(Sc1ccc(O)cc1)=CC3=O)c(=O)n(C)c(=O)n2C] | 6-Ethyl-8-((4-hydroxyphenyl)thio)-2,4-dimethylpyrimido[4,5-c]isoquinoline-1,3,7,10(2H,4H)-tetraone |

-continued

| No | Structure | IUPAC Name |
|---|---|---|
| 19 | 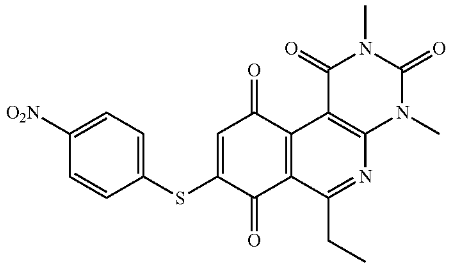 [SMILES: CCc1nc2c(c3c1C(=O)C(Sc1ccc([N+](=O)[O-])cc1)=CC3=O)c(=O)n(C)c(=O)n2C] | 6-Ethyl-2,4-dimethyl-8-((4-nitrophenyl)thio)pyrimido[4,5-c]isoquinoline-1,3,7,10(2H,4H)-tetraone |
| 20 | 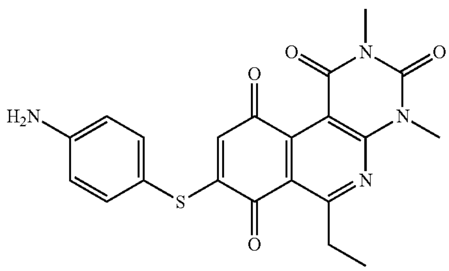 | 8-((4-aminophenyl)thio)-6-ethyl-2,4-dimethylpyrimido[4,5-c]isoquinoline-1,3,7,10(2H,4H)-tetraone |
| 21 | 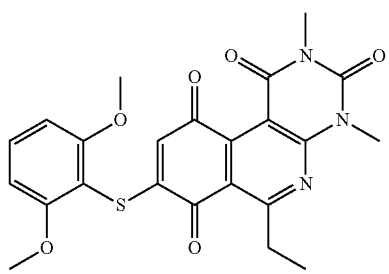 [SMILES: CCc1nc2c(c3c1C(=O)C(Sc1c(OC)cccc1OC)=CC3=O)c(=O)n(C)c(=O)n2C] | 8-((2,6-dimethoxyphenyl)thio)-6-ethyl-2,4-dimethylpyrimido[4,5-c]isoquinoline-1,3,7,10(2H,4H)-tetraone |
| 22 | 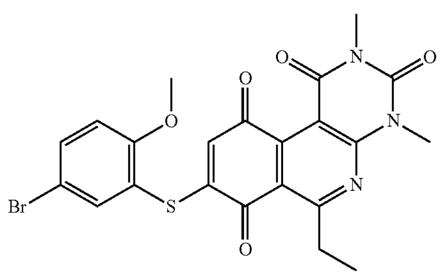 [SMILES: CCc1nc2c(c3c1C(=O)C(Sc1cc(Br)ccc1OC)=CC3=O)c(=O)n(C)c(=O)n2C] | 8-((5-bromo-2-methoxyphenyl)thio)-6-ethyl-2,4-dimethylpyrimido[4,5-c]isoquinoline-1,3,7,10(2H,4H)-tetraone |
| 23 | 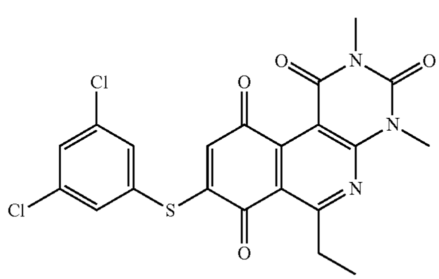 [SMILES: CCc1nc2c(c3c1C(=O)C(Sc1cc(Cl)cc(Cl)c1)=CC3=O)c(=O)n(C)c(=O)n2C] | 8-((3,5-dichlorophenyl)thio)-6-ethyl-2,4-dimethylpyrimido[4,5-c]isoquinoline-1,3,7,10(2H,4H)-tetraone |

-continued

| No | Structure | IUPAC Name |
|---|---|---|
| 24 | 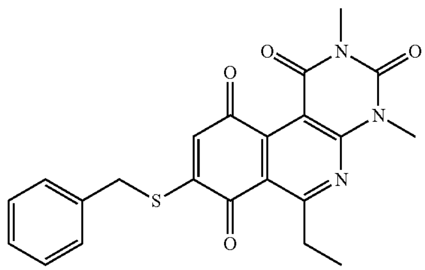 [SMILES: CCc1nc2c(c3c1C(=O)C(SCc1ccccc1)=CC3=O)c(=O)n(C)c(=O)n2C] | 8-(benzylthio)-6-ethyl-2,4-dimethylpyrimido[4,5-c]isoquinoline-1,3,7,10(2H,4H)-tetraone |
| 25 | 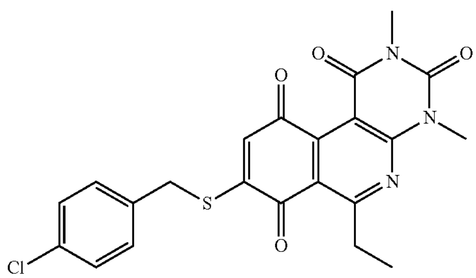 [SMILES: CCc1nc2c(c3c1C(=O)C(SCc1ccc(Cl)cc1)=CC3=O)c(=O)n(C)c(=O)n2C] | 8-((4-chlorobenzyl)thio)-6-ethyl-2,4-dimethylpyrimido[4,5-c]isoquinoline-1,3,7,10(2H,4H)-tetraone |
| 26 | 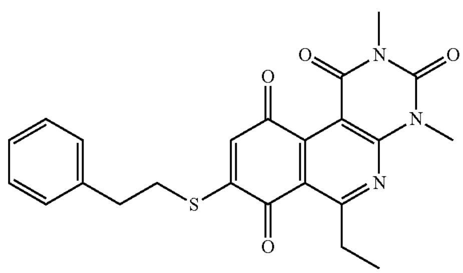 [SMILES: CCc1nc2c(c3c1C(=O)C(SCCc1ccccc1)=CC3=O)c(=O)n(C)c(=O)n2C] | 6-Ethyl-2,4-dimethyl-8-(phenylethylthio)pyrimido[4,5-c]isoquinoline-1,3,7,10(2H,4H)-tetraone |
| 27 | 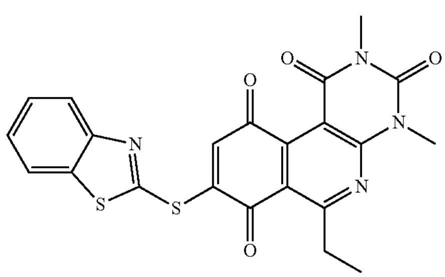 [SMILES: CCc1nc2c(c3c1C(=O)C(Sc1nc4ccccc4s1)=CC3=O)c(=O)n(C)c(=O)n2C] | 8-(benzothiazole-2-ylthio)-6-ethyl-2,4-dimethylpyrimido[4,5-c]isoquinoline-1,3,7,10(2H,4H)-tetraone |
| 28 | 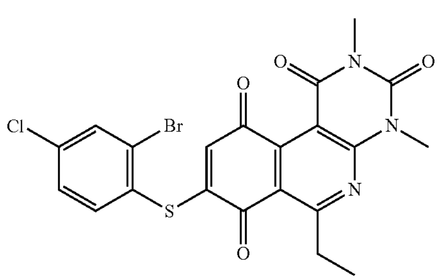 [SMILES: CCc1nc2c(c3c1C(=O)C(Sc1ccc(Cl)cc1Br)=CC3=O)c(=O)n(C)c(=O)n2C] | 8-((2-bromo-4-chlorophenyl)thio)-6-ethyl-2,4-dimethylpyrimido[4,5-c]isoquinoline-1,3,7,10(2H,4H)-tetraone |

| No | Structure | IUPAC Name |
|---|---|---|
| 29 | 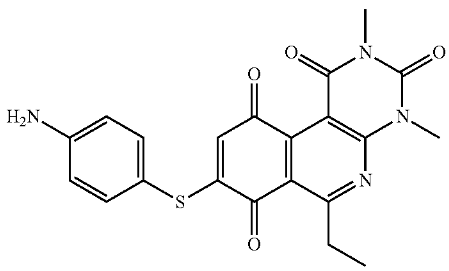 | 8-((4-aminophenyl)amino)-6-ethyl-2,4-dimethylpyrimido[4,5-c]isoquinoline-1,3,7,10(2H,4H)-tetraone |
| 30 | 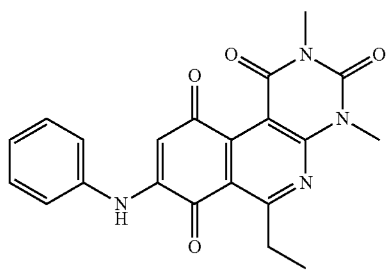 [SMILES: CCc1nc2c(c3c1C(=O)C(Nc1ccccc1)=CC3=O)c(=O)n(C)c(=O)n2C] | 6-Ethyl-2,4-dimethyl-8-(phenylamino)pyrimido[4,5-c]isoquinoline-1,3,7,10(2H,4H)-tetraone |
| 31 | 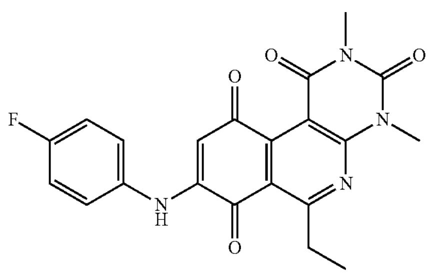 [SMILES: CCc1nc2c(c3c1C(=O)C(Nc1ccc(F)cc1)=CC3=O)c(=O)n(C)c(=O)n2C] | 6-Ethyl-8-((4-fluorophenyl)amino 2,4-dimethylpyrimido[4,5-c]isoquinoline-1,3,7,10(2H,4H) tetraone |
| 32 | 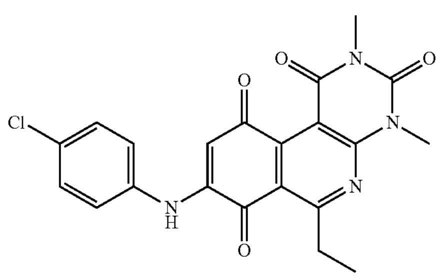 | 8-((4-chlorophenyl)amino)-6-ethyl-2,4-dimethylpyrimido[4,5-c]isoquinoline-1,3,7,10(2H,4H)-tetraone |
| 33 | 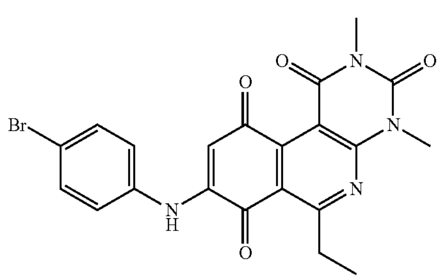 [SMILES: CCc1nc2c(c3c1C(=O)C(Nc1ccc(Cl)cc1)=CC3=O)c(=O)n(C)c(=O)n2C] | 8-((4-bromophenyl)amino)-6-ethyl-2,4-dimethylpyrimido[4,5-c]isoquinoline-1,3,7,10(2H,4H)-tetraone |

-continued

| No | Structure | IUPAC Name |
|---|---|---|
| 34 | 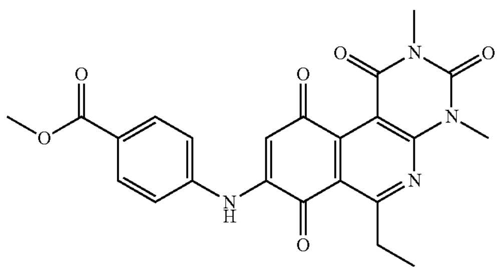 | Methyl-4-((6-ethyl-2,4-dimethyl-1,3,7,10-tetraoxo-1,2,3,4,7,10-)hexahydropyrimido[4,5c]isoquinoline-8-yl)amino)benzoate |
| 35 | 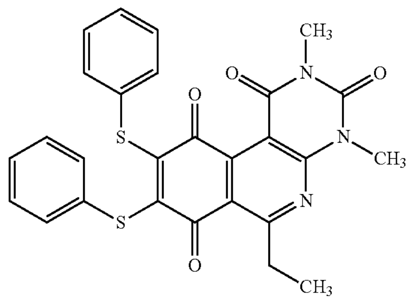 [SMILES: CCc1nc2c(c3c1C(=O)C(Sc1ccccc1)=C(Sc1ccccc1)C3=O)c(=O)n(C)c(=O)n2C] | 8,9-bis-thiophenyl-6-ethyl-2,4-dimethyl-pyrimido[4,5-c]isoquinoline-1,3,7,10(2H,4H)-tetraone |
| 36 | 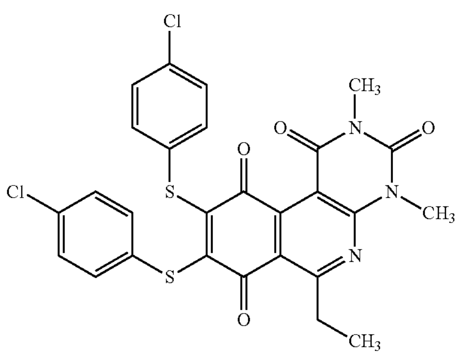 [SMILES: CCc1nc2c(c3c1C(=O)C(Sc1ccc(Cl)cc1)=C(Sc1ccc(Cl)cc1)C3=O)c(=O)n(C)c(=O)n2C] | 8,9-Bis(4-chlorothiophenyl)-6-ethyl-2,4-dimethylpyrimido[4,5-c]isoquinoline-1,3,7,10(2H,4H)-tetraone |
| 37 | 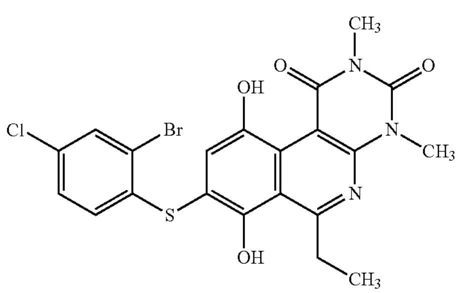 [SMILES: CCc1nc2c(c(=O)n(C)c(=O)n2C)c2c(O)cc(Sc3ccc(Cl)cc3Br)c(O)c12] | 8-(2-bromo-4-chloro-thiophenyl)-6-ethyl-7,10-dihydroxy-2,4-dimethylpyrimido[4,5-c]isoquinolinee-1,3(2H,4H)-dione |
| 38 | 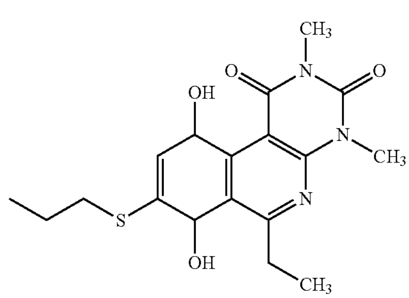 [SMILES: CCCSC1=CC(O)c2c(c(CC)nc3c2c(=O)n(C)c(=O)n3C)C1O] | 8-Thiopropyl-6-ethyl-2,4-dimethyl-pyrimido[4,5-c]isoquinoline-1,3,7,10(2H,4H)-tetraone |

-continued

| No | Structure | IUPAC Name |
|---|---|---|
| 39 | 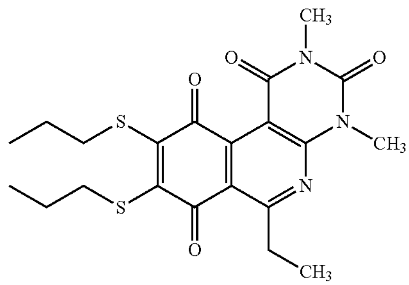 [SMILES: CCCSC1=C(SCCC)C(=O)c2c(c(CC)nc3c2c(=O)n(C)c(=O)n3C)C1=O] | 8,9-bis-tiopropyl-6-ethyl-6-2,4-dimethyl-2,4-dimethyl-pyrimido[4,5-c]isoquinoline-1,3,7,10(2H,4H)-tetraone |

Figure 1:
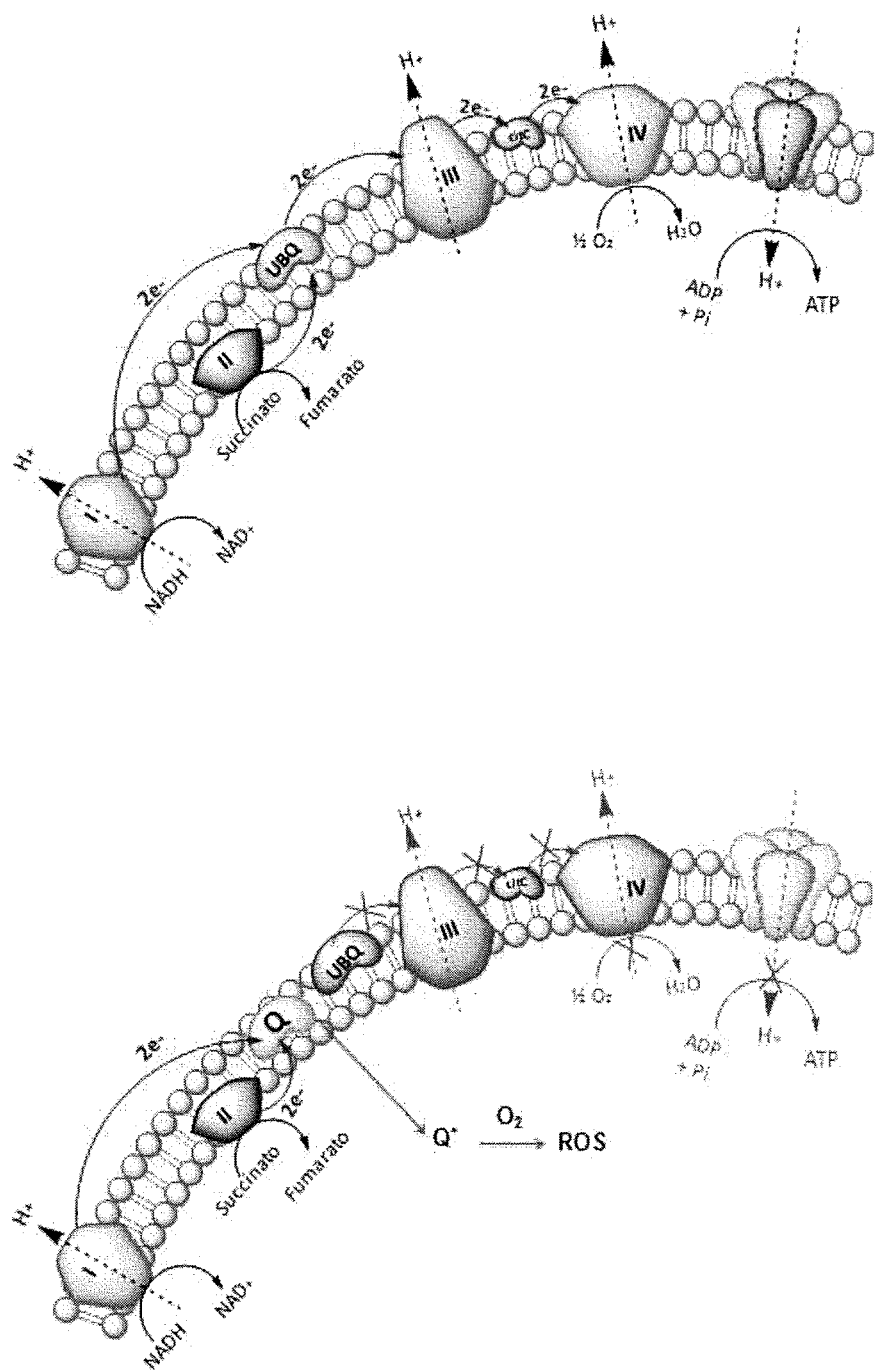
FIG. 1/3
Figure 2:
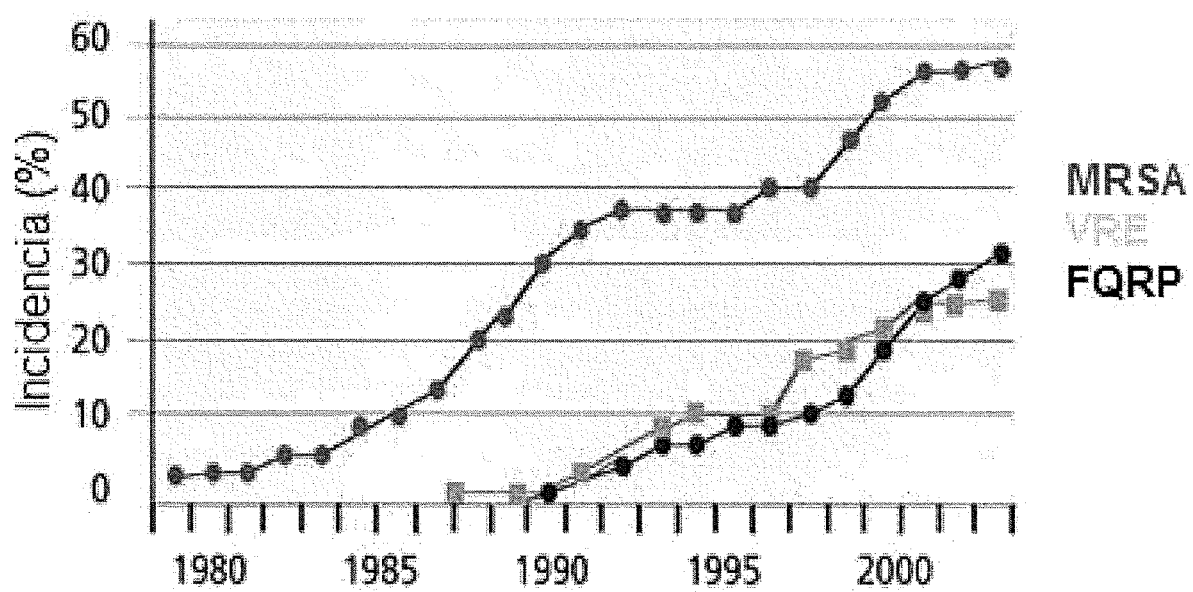

This figure depicts the electron transport chain (CTe).
A. Representation of the normal flow of electrons through the CTe complexes, where the energy released from this flow of electrons is used to translocate protons against the gradient, which is an energetically unfavorable process. The electrochemical gradient generated is used to form ATP by means of an energetically-favorable process.
B. Representation of the blockage in the flow of electrons created by the quinonic compounds of the present invention (Q) by emulating ubiquinone. This leads to a decrease in the generation of PTAs and/or the production of ROS.

FIG. 3/3

This figure shows a superior diagram demonstrating the performance of the compound in example 16 of formula I against Gram (−) bacteria of the *Escherichia Coli* ATCC©25922 type.

The diagram below shows the performance of the compound in example 16 of formula I against Gram (−) bacteria of the *Pseudomonas Aeruginosa* ATCC©27853 type.

For these purposes, the compound in formula I (Example 16) was combined with different concentrations of EDTA.

Experimental Tests

These compounds were tested for their in vitro activity (Screening Antibacterial Activity CIM (μg/mL)) and the results are shown in Table II.

TABLE II

| | CIM antibacterial activity screening (μg/mL) | | | | |
|---|---|---|---|---|---|
| Molecule | Methicillin resistant *Staphylococcus aureus* ATCC 43300 | Methicillin sensitive *Staphylococcus aureus* ATCC 29213 | *Enterococcus faecalis* ATCC 29212 | *Eschericha coli* ATCC 25922 | *Pseudomona aeruginosa* ATCC 27853 |
| 1 | ≥32 | ≥32 | >32 | >32 | >32 |
| 2 | 8 | 8 | 8 | ≥32 | ≥32 |
| 3 | 32 | 32 | ≥32 | ≥32 | ≥32 |
| 4 | 2 | 4 | 4 | ≥32 | ≥32 |
| 5 | ≥32 | ≥32 | ≥32 | ≥32 | ≥32 |
| 6 | ≥32 | ≥32 | ≥32 | ≥32 | ≥32 |
| 7 | 1 | 4 | 2 | ≥32 | ≥32 |
| 8 | 4 | 4 | 4 | ≥32 | ≥32 |
| 9 | 4 | 8 | 4 | ≥32 | ≥32 |
| 10 | 4 | 4 | 8 | ≥32 | ≥32 |
| 11 | 2 | 32 | 4 | ≥32 | ≥32 |
| 12 | 2 | 32 | 4 | ≥32 | ≥32 |
| 13 | 4 | 4 | 16 | ≥32 | ≥32 |
| 14 | 16 | 16 | 16 | ≥32 | ≥32 |
| 15 | 8 | 8 | 8 | ≥32 | ≥32 |
| 16 | 4 | 4 | 4 | ≥32 | ≥32 |
| 17 | 4 | 8 | 8 | ≥32 | ≥32 |

FIG. 2/3

This figure presents a graph showing the increased resistance rates of three bacteria of concern to public health authorities: (MRSA), (VRE) and (FQRP).

The data was obtained from the intensive care units of hospitals participating in the US National Nosocomial Infection Surveillance System.

MRSA: Methicillin-resistant *Staphylococcus aureus*
VRE: Vancomycin-resistant Enterococci
FQRP: Fluoroquinolone resistant *Pseudomonas aeruginosa*

After the Antibacterial Activity Screening, tests were conducted to verify antibacterial activity in a heterogeneous bacterial population. The results are shown in Table III below.

TABLE III

| Origin | No. of isolations | Range CIM | CIM50 | CIM90 | MG CIM |
|---|---|---|---|---|---|
| Tracheal aspiration | 10 | 4-2 | 2 | 4 | 2.40 |

TABLE III-continued

| Origin | No. of isolations | Range CIM | CIM50 | CIM90 | MG CIM |
|---|---|---|---|---|---|
| Wound | 10 | 4-2 | 2 | 2 | 2.20 |
| Blood | 11 | 32-1 | 2 | 4 | 4.81 |
| Others | 2 | 4-2 | 2 | 4 | 3.00 |
| TOTAL | 33 | 4-1 | 2 | 2 | 3.10 |
| Tracheal aspiration | 9 | 4-1 | 2 | 4 | 2.33 |
| Wound | 9 | 4-1 | 2 | 4 | 2.11 |
| Blood | 9 | 2-1 | 2 | 2 | 1.77 |
| Others | 2 | 4-2 | 2 | 4 | 3.00 |
| TOTAL | 29 | 4-1 | 2 | 4 | 2.30 |
| Urine | 10 | 4-2 | 2 | 4 | 2.67 |
| Peritoneal liquid | 10 | 4-2 | 2 | 2 | 2.20 |
| Wound | 10 | 4-2 | 2 | 4 | 2.80 |
| Blood | 10 | 4-2 | 2 | 4 | 2.60 |
| Others | 4 | 4-2 | 2 | 4 | 2.50 |
| TOTAL | 44 | 4-2 | 2 | 4 | 2.59 |

Bacteria used: A panel of prototype strains was used to screen for antibacterial activity in the compounds:
  Methicillin-resistant *Staphylococcus aureus* ATCC© 43300.
  Methicillin-sensitive *Staphylococcus aureus* ATCC© 29213.
  *Enterococcus faecalis* ATCC© 29212.
  *Escherichia coli* ATCC© 25922.
  *Pseudomonas aeruginosa* ATCC© 27853.

The compounds that were most active were tested on a panel of 89 Gram-positive cocaccea clinical isolates taken in 2014 from various Chilean hospitals. The isolates used were methicillin-resistant *Staphylococcus aureus* and vancomycin-resistant *Enterococcus* spp. that met a certain multi-resistance susceptibility profile, defined by isolates resistant to at least one representative of 2 or more families of antibacterials. The isolation sites of origin for *Staphylococcus aureus* were via tracheal aspiration, wound and blood, while the sites for *Enterococcus* spp. were urine, peritoneal fluid, blood and wound.

The strains were planted from the ceparium (where they were preserved in 50% v/v glycerol and Brain Heart Infusion culture broth, at −20° C.) in Mueller-Hinton agar (Oxoid, England).

To determine the minimum inhibitory concentration (MIC), the microdilution technique in culture medium was used according to the protocol suggested by CLSI, in short: In 96-well sterile culture plates (8 rows and 12 columns) (Ultracruz™ Polystyrene Microplates, 96 well, U bottom Santa Cruz biotechnology, inc.) 100 uL of Mueller Hinton broth were added to all wells, then 100 uL of control antibiotic or compound to be tested in the 8 rows of the first column, to continue making serial dilutions with a dilution factor of 0.5. The concentrations to be tested ranged from 32 to 0.0625 µg/mL. The wells in columns 11 and 12 were used for positive growth control and sterility control respectively.

Once the plate was prepared, 100 uL of the bacterial suspension to be tested were added, previously adjusted to 0.5 Mc Farland, in each of the wells, excluding the wells in column 12. Finally, the plates were covered and incubated at 36° C. for 18 to 24 hours. Then, the plates were observed using contrast light to determine the concentration at which bacterial growth is inhibited (indicated by the disappearance of turbidity).

All trials were conducted three times, and results were considered valid if the internal controls of each plate (growth and sterility controls) were adequate. MIC antibiotic control (ciprofloxacin, gentamicin and vancomycin) was assessed and contrasted with the permitted quality control ranges given by CLSI. If the MIC detected in the trial was within the permitted ranges, the trial was accepted as valid.

The compounds of this invention are useful for the treatment of infectious diseases, preferably multi-resistant to antibiotics in mammals, for example, humans.

The foregoing description details the specific methods and compositions that may be used to implement the present invention and sets the best way forward. However, it is clear to an art expert that other compounds with the desired pharmacological properties can be prepared in a similar way, and that the revealed compounds can also be obtained from different starting compounds via different chemical reactions. Similarly, different pharmaceutical compositions can be prepared and used with substantially the same results. Even though the above may appear in detail in the text, it should not be interpreted as limiting the general scope of the present invention. On the contrary, the scope of the present invention is governed only by the legal interpretation of the attached claims.

Figure 3:
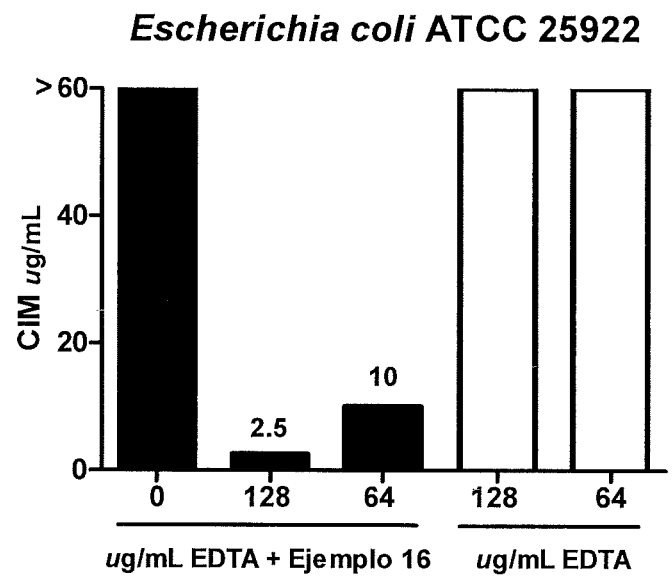
Figure 3:
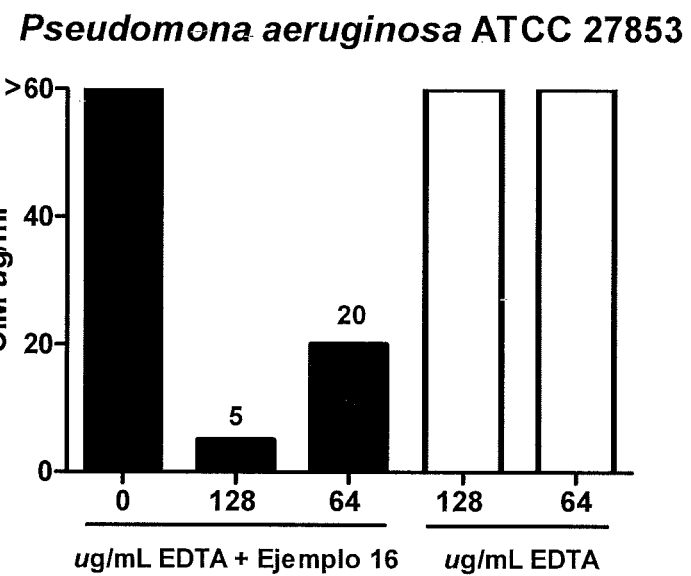

On the other hand, tests were conducted to verify the activity against Gram (−) bacteria. Two strains were tested: *Escherichia Coli* ATCC©25922 and *Pseudomonas Aeruginosa* ATCC©27853. For this purpose, the compound of formula I (Example 16) was combined with different concentrations of EDTA delivering the following results presented in FIG. 3/3.

In summary, the results obtained indicate that EDTA allows the formula I antibiotic to act on Gram (−) strains in a concentration range between 10 to 800 µg/ml, preferably in the range of 64 to 128 µg/ml.

On the other hand and in a more general context, the prior art used in the present development is summarized in the following list:
1. Munck T., La Europa del Siglo XVII. 1598-1700, Editor E. Akal. 1994: España. p. 132-137.
2. Gloria Pérez, A. D. J. O., Elena Cuenca París, Ma Rosario Limón Mendizábal, Julio Lancho, María del Carmen Ortega, Álvaro Muelas, Calidad de Vida en las Personas Adultas y Mayores ed. U.N.d.E.a. distancia. 2013, Madrid.
3. Cabello, R., Microbiología y parasitología humana. Bases etiológicas de las enfermedades infecciosas y parasitarias. 3 a ed. 2007.
4. Baldry, P., La batalla contra las bacterial, C. Cambridge University Press. 1981: España. p. 73-97.
5. Roca, A. J., Historia de los medicamentos. la ed. 2003, Bogotá, Colombia.
6. Pedro de Lorenzo Fernández, B. L. V., Alfonso Moreno González, Ignacio Lizasoain Hernández, Juan Carlos Leza Cerro, Maria Ángeles Sánchez Moro, Antonio Portolés Pérez, Farmacología: Básica y Clínica. ed. 18 ava ed. E. M. Panamericana. 2008.
7. Schon, I., Diccionario de la lengua espanola (Book). Booklist, 2002. 99(5): p. 524.
8. García, P., Resistencia Bacteriana en Chile. Revista Chilena de Infectología; 20 (Supl 1): S11-S23, 2003.
9. Ji, Y. and T. Lei, Antisense RNA regulation and application in the development of novel antibiotics to combat multidrug resistant bacteria. Sci Prog, 2013. 96(Pt 1): p. 43-60.

10. Plaza, D. M. J. M. La Infección Nosocomial. Resistencias bacterianas en Pacientes crónicos. 2011: Valencia. p. 57.
11. OMS, Informe sobre la salud en el mundo: un porvenir más seguro. Protección de la salud pública mundial en el siglo XXI. 2007: Suiza.
12. OMS. Resistencia a los antimicrobianos (RAM). http://www.who.int/mediacentre/factsheets/fs194/es/2012.
13. Heymann, D., The desk encyclopedia of microbiology, E. A. Press. 2004, Amsterdam.
14. Levy, S. B., Antimicrobial resistance: bacteria on the defence. Resistance stems from misguided efforts to try to sterilise our environment. BMJ, 1998. 317(7159): p. 612-3.
15. Collignon, P., et al., Human Deaths and Third-Generation Cephalosporin use in Poultry, Europe. Emerg Infect Dis, 2013. 19(8): p. 1339-40.
16. Angela Restrepo, J. R., Eduardo Leiderman, Marcos Restrepo, David Botero, Victoria Bedoya, Enfermedades Infecciosas, C.p.i. biolódicas, Editor. 2003: Colombia. p. 38.
17. Gustavo A. Quintero, J. A. N., Carlos H. Lerma, Infección en Cirugia, E. M. Panamericana. 2001: Colombia p. 106.
18. Dbaibo, G. S., Old and new targets of antibacterial therapy. J Med Liban, 2000. 48(4): p. 177-81.
19. Donald Voet, J. G. V., Bioquimica, E. M. Panamericana. 2006. p. 829-851.
20. Harmon, H. J. and V. G. Struble, Effects of 2-hydroxy-3-undecyl-1,4-naphthoquinone on respiration of electron transport particles and mitochondria: topographical location of the Rieske iron-sulfur protein and the quinone binding site. Biochemistry, 1983. 22(19): p. 4394-400.
21. Devlin, T. M., Bioquímica: libro de texto con aplicaciones clínicas, E. Reverté. 2004.
22. Salmon-Chemin, L., et al., 2- and 3-substituted 1,4-naphthoquinone derivatives as subversive substrates of trypanothione reductase and lipoamide dehydrogenase from Trypanosoma cruzi: synthesis and correlation between redox cycling activities and in vitro cytotoxicity. J Med Chem, 2001. 44(4): p. 548-65.
23. Dharmaraja, A. T., et al., Design, synthesis and evaluation of small molecule reactive oxygen species generators as selective Mycobacterium tuberculosis inhibitors. Chem Commun (Camb), 2012. 48(83): p. 10325-7.
24. Xiao-Ming Yin, Z. D., Reactive Oxygen Species in Cell Fate Decisions, in Essentials of Apoptosis: A Guide for Basic and Clinical Research. 2009. p. 202.
25. Lluvia Itzel Lopez L., E. L., Ramón Fernando García de la Cruz, Las naftoquinones: más que pigmentos naturales. Revista Mexicana de Ciencias Farmacéuticas, 2011. 42: p. 7-14.
26. Karkare, S., et al., The naphthoquinone diospyrin is an inhibitor of DNA gyrase with a novel mechanism of action. J Biol Chem, 2013. 288(7): p. 5149-56.
27. Lima, N. M., et al., Antileishmanial activity of lapachol analogues. Mem Inst Oswaldo Cruz, 2004. 99(7): p. 757-61.
28. Salas, C., et al., Trypanosoma cruzi: activities of lapachol and alpha- and beta-lapachone derivatives against epimastigote and trypomastigote forms. Bioorg Med Chem, 2008. 16(2): p. 668-74.
29. Ferreira, D. T., et al., Antimicrobial activity and chemical investigation of Brazilian Drosera. Mem Inst Oswaldo Cruz, 2004. 99(7): p. 753-5.
30. Cai, L., et al., Namibian chewing stick, Diospyros lycioides, contains antibacterial compounds against oral pathogens. J Agric Food Chem, 2000. 48(3): p. 909-14.
31. Riffel, A., et al., In vitro antimicrobial activity of a new series of 1,4-naphthoquinones. Braz J Med Biol Res, 2002. 35(7): p. 811-8.
32. Tandon, V. K., et al., Synthesis and biological evaluation of novel 1,4-naphthoquinone derivatives as antibacterial and antiviral agents. Bioorg Med Chem Lett, 2005. 15(14): p. 3463-6.
33. Nagata K., et al., Antimicrobial activity of novel furanonaphthoquinone analogs. Antimicrob Agents Chemother, 1998. 42(3): p. 700-2.
34. Eyong, K. O., et al., Newbouldiaquinone A: A naphthoquinone-anthraquinone ether coupled pigment, as a potential antimicrobial and antimalarial agent from Newbouldia laevis. Phytochemistry, 2006. 67(6): p. 605-9.
35. CLSI, Methods for Dilution Antimicrobial Susceptibility Tests for Bacteria that Grow Aerobically. Approved Standard, 2009. 23(2).
36. Valderrama J A, V. D., Design and synthesis of anguciclinone AB-pyrido[2,3-d]pyrimido analogues. Tetrahedron Lett 2008; 49:703-6.
37. Vásquez, D., Diseño, síntesis y evaluación antitumoral de aza-análogos de anguciclinonas y derivados de aminopirimidoisoquinolinequinones, Departamento de Química Orgánica. 2009, Pontificia Universidad Católica de Chile: Santiago, Chile. p. 216.
38. L. G. Wade, J., Organic Chemistry, P. Hall. 1991. p. 1026-1028.
39. Javier Campanini Salinas, D. V. V., Síntesis, Caracterización y Evaluación de la Actividad Antibacteriana de una serie de Arilmercaptopirimidoisoquinolinequinones, Facultad de Ciencias Químicas y Farmacéuticas. 2012, Universidad de Chile: Chile.
40. Salmerón, D. P. S., Estudio oscilopolarográfico de Vitaminas. XIV: p. 387-389.
41. McMurry, J., Organic Chemistry, T. Brooks/Cole, Editor. 2008. p. 560-577.
42. Sara Aldabe, C. B., Laura Lacreu, Pedro Aramendia, Química 2: Química en acción, 1 ed. Colihue. 2004, Buenos Aires.
43. Santiago Luis Lafuente, M. I. B. A., Belén Altava Benito, Introducción a la Química Orgánica. 1997. p. 161-166.
44. Gilman, G. a., Las Bases Farmacológicas de la Terapéutica 2001. p. 1675-1688.
45. Roberto Todeschini, V. C., Molecular Descriptors for Chemoinformatics. 2 ed. Wiley. 2009.
46. Connors, K. A., Curso de Análisis Farmacéutico., Reverté. p. 273.
47. Bergeron, F., et al., Near-UV photolysis of 2-methyl-1,4-naphthoquinone-DNA duplexes: characterization of reversible and stable interstrand cross-links between quinone and adenine moieties. Chem Res Toxicol, 2007. 20(5): p. 745-56.

The invention claimed is:

1. A pyrimido-isoquinoline-quinone compound of formula I, tautomer thereof, or pharmaceutically acceptable salt thereof

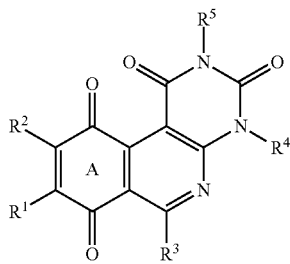

wherein:
R$^1$ is —S—R$^6$;
R$^2$ is —H;
R$^3$ is —CH$_2$—CH$_3$;
R$^4$ and R$^5$ are —CH$_3$; and
R$^6$ is phenyl optionally substituted by at least one of —CH$_3$, —O—CH$_3$, —Cl, —Br, —F, and mixtures thereof.

2. The pyrimido-isoquinoline-quinone compound according to claim 1 wherein the R$^6$ phenyl group is substituted in the ortho, meta, and/or para positions, or any combination thereof.

3. The pyrimido-isoquinoline-quinone compound according to claim 1, wherein the compound is selected from the group consisting of:
6-ethyl-2,4-dimethyl-8-(phenythio)pyrimido[4,5-c]isoquinoline-1,3,7,10(2H,4H)-tetraone;
6-ethyl-2,4-dimethyl-8-(o-tolylthio)pyrimido[4,5-c]isoquinoline-1,3,7,10(2H,4H)-tetraone;
6-ethyl-8-((2-methoxyphenyl)thio)-2,4-dimethylpyrimido[4,5-c]isoquinoline-1,3,7,10(2H,4H)-tetraone;
6-ethyl-8-((2-fluorophenyl)thio)-2,4-dimethylpyrimido[4,5-c]isoquinoline-1,3,7,10(2H,4H)-tetraone;
8-((2-chlorophenyl)thio)-6-ethyl-2,4-dimethylpyrimido[4,5-c]isoquinoline-1,3,7,10(2H,4H)-tetraone;
8-((2-bromophenyl)thio)-6-ethyl-2,4-dimethylpyrimido[4,5-c]isoquinoline-1,3,7,10(2H,4H)-tetraone;
6-ethyl-2,4-dimethyl-8-(m-tolylthio)pyrimido[4,5-c]isoquinoline-1,3,7,10(2H,4H)-tetraone;
6-ethyl-8-((3-methoxyphenyl)thio)-2,4-dimethylpyrimido[4,5-c]isoquinoline-1,3,7,10(2H,4H)-tetraone;
6-ethyl-8-((3-fluorophenyl)thio)-2,4-dimethylpyrimido[4,5-c]isoquinoline-1,3,7,10(2H,4H)-tetraone;
8-((3-chlorophenyl)thio)-6-ethyl-2,4-dimethylpyrimido[4,5-c]isoquinoline-1,3,7,10(2H,4H)-tetraone;
8-((3-bromophenyl)thio)-6-ethyl-2,4-dimethylpyrimido[4,5-c]isoquinoline-1,3,7,10(2H,4H)-tetraone;
6-ethyl-2,4-dimethyl-8-(p-tolylthio)pyrimido[4,5-c]isoquinoline-1,3,7,10(2H,4H)-tetraone;
6-ethyl-8-((4-methoxyphenyl)thio)-2,4-dimethylpyrimido[4,5-c]isoquinoline-1,3,7,10(2H,4H)-tetraone;
6-ethyl-8-((4-fluorophenyl)thio)-2,4-dimethylpyrimido[4,5-c]isoquinoline-1,3,7,10(2H,4H)-tetraone;
8-((4-chlorophenyl)thio)-6-ethyl-2,4-dimethylpyrimido[4,5-c]isoquinoline-1,3,7,10(2H,4H)-tetraone; and
8-((4-bromophenyl)thio)-6-ethyl-2,4-dimethylpyrimido[4,5-c]isoquinoline-1,3,7,10(2H,4H)-tetraone.

4. A method of treating bacterial infections, comprising administering to a patient in need thereof an effective amount of at least one pyrimido-isoquinoline-quinone compound according to claim 1.

5. The method according to claim 4, wherein the bacterial infection is selected from the group consisting of *Staphylococcus aureus* resistant to methicillin (MRSA or SARM), *Staphylococcus aureus* with intermediate resistance to vancomycin (VISA), *Staphylococcus aureus* resistant to vancomycin (VRSA), *Enterococcus* resistant to vancomycin (VRE), EF strains, emerging *Staphylococcus aureus* resistant to linezolid, and/or bacterial strains not susceptible to daptomycin.

6. The method according to claim 4, wherein the bacterial infection belongs to a Gram-negative bacterial strain.

7. A pharmaceutical composition comprising at least one pyrimido-isoquinoline-quinone compound according to claim 1, tautomer thereof, or pharmaceutically acceptable salt thereof, or a combination thereof.

8. A method of treating bacterial infections, comprising administering to a patient in need thereof an effective amount of at least one pharmaceutical composition according to claim 7.

9. The method according to claim 8, wherein the bacterial infection is selected from the group consisting of *Staphylococcus aureus* resistant to methicillin (MRSA or SARM), *Staphylococcus aureus* with intermediate resistance to vancomycin (VISA), *Staphylococcus aureus* resistant to vancomycin (VRSA), *Enterococcus* resistant to vancomycin (VRE), EF strains, emerging *Staphylococcus aureus* resistant to linezolid, and/or bacterial strains not susceptible to daptomycin.

10. The method according to claim 8, wherein the bacterial infection belongs to a Gram-negative bacterial strain.

11. A pharmaceutical composition comprising at least one pyrimido-isoquinoline-quinone compound according to claim 3, tautomer thereof, or pharmaceutically acceptable salt thereof, or a combination thereof.

12. A method of treating bacterial infections, comprising administering to a patient in need thereof an effective amount of the pharmaceutical composition according to claim 11.

13. The method according to claim 12, wherein the bacterial infection is selected from the group consisting of *Staphylococcus aureus* resistant to methicillin (MRSA or SARM), *Staphylococcus aureus* with intermediate resistance to vancomycin (VISA), *Staphylococcus aureus* resistant to vancomycin (VRSA), *Enterococcus* resistant to vancomycin (VRE), EF strains, emerging *Staphylococcus aureus* resistant to linezolid, and/or bacterial strains not susceptible to daptomycin.

14. The method according to claim 12, wherein the bacterial infection belongs to a Gram-negative bacterial strain.

* * * * *